US010092519B2

(12) United States Patent
Oshlack et al.

(10) Patent No.: US 10,092,519 B2
(45) Date of Patent: *Oct. 9, 2018

(54) PHARMACEUTICAL PRODUCTS

(71) Applicant: Purdue Pharma L.P., Stamford, CT (US)

(72) Inventors: Benjamin Oshlack, Boca Raton, FL (US); Glenn Van Buskirk, Basking Ridge, NJ (US); Mark Chasin, Monroe, NJ (US); Hua-Pin Huang, Englewood Cliffs, NJ (US); Vijay Vashi, Millstone Township, NJ (US)

(73) Assignee: Purdue Pharma L.P., Stamford, CT (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/838,458

(22) Filed: Aug. 28, 2015

(65) Prior Publication Data

US 2015/0366811 A1 Dec. 24, 2015

Related U.S. Application Data

(63) Continuation of application No. 10/827,623, filed on Apr. 19, 2004, now Pat. No. 9,149,436.

(60) Provisional application No. 60/464,323, filed on Apr. 21, 2003.

(51) Int. Cl.
| | | |
|---|---|---|
| A61K 9/20 | (2006.01) | |
| A61K 9/28 | (2006.01) | |
| A61K 9/51 | (2006.01) | |
| A61K 31/485 | (2006.01) | |
| A61K 9/48 | (2006.01) | |
| A61K 9/50 | (2006.01) | |
| A61K 45/06 | (2006.01) | |
| A61K 9/16 | (2006.01) | |

(52) U.S. Cl.
CPC ............ *A61K 9/2081* (2013.01); *A61K 9/282* (2013.01); *A61K 9/2826* (2013.01); *A61K 9/2846* (2013.01); *A61K 9/2866* (2013.01); *A61K 9/4808* (2013.01); *A61K 9/4858* (2013.01); *A61K 9/4866* (2013.01); *A61K 9/5084* (2013.01); *A61K 9/5123* (2013.01); *A61K 9/5138* (2013.01); *A61K 31/485* (2013.01); *A61K 45/06* (2013.01); *A61K 9/1617* (2013.01); *A61K 9/1635* (2013.01); *A61K 9/5026* (2013.01); *A61K 9/5047* (2013.01); *A61K 9/5073* (2013.01)

(58) Field of Classification Search
None
See application file for complete search history.

(56) References Cited

U.S. PATENT DOCUMENTS

| | | | |
|---|---|---|---|
| 586,997 A | 7/1897 | Grout | 424/473 |
| 2,770,569 A | 11/1956 | Fromherz et al. | 167/65 |
| 3,133,132 A | 5/1964 | Loeb et al. | 264/49 |
| 3,173,876 A | 3/1965 | Zobrist | 252/137 |
| 3,173,877 A | 3/1965 | Jackson et al. | 252/138 |
| 3,276,586 A | 10/1966 | Rosaen | 210/90 |
| 3,332,950 A | 7/1967 | Blumberg et al. | 260/285 |
| 3,493,657 A | 2/1970 | Lewenstein et al. | 424/260 |
| 3,541,005 A | 11/1970 | Strathmann et al. | 210/19 |
| 3,541,006 A | 11/1970 | Bixler et al. | 210/23 |
| 3,676,557 A | 7/1972 | Lachman et al. | 424/260 |
| 3,773,955 A | 11/1973 | Pachter et al. | 424/260 |
| 3,845,770 A | 11/1974 | Theeuwes et al. | 128/260 |
| 3,879,555 A | 4/1975 | Pachter et al. | 424/260 |
| 3,916,889 A | 11/1975 | Russell | 128/145.8 |
| 3,965,256 A | 6/1976 | Leslie | 424/22 |
| 3,966,940 A | 6/1976 | Pachter et al. | 424/260 |
| 4,063,064 A | 12/1977 | Saunders et al. | 219/121 |
| 4,088,864 A | 5/1978 | Theeuwes et al. | 219/121 |
| 4,160,020 A | 7/1979 | Ayer et al. | 424/15 |
| 4,176,186 A | 11/1979 | Goldberg | 424/260 |
| 4,200,098 A | 4/1980 | Ayer et al. | 128/260 |
| 4,237,140 A | 12/1980 | Dudzinski | 424/260 |
| 4,285,987 A | 8/1981 | Ayer et al. | 427/3 |
| 4,293,539 A | 10/1981 | Ludwig et al. | 429/19 |
| 4,366,310 A | 12/1982 | Leslie | 536/56 |
| 4,401,672 A | 8/1983 | Portoghese et al. | 424/260 |
| 4,443,428 A | 4/1984 | Oshlack et al. | 424/22 |
| 4,451,470 A | 5/1984 | Ganti | 424/260 |
| 4,457,933 A | 7/1984 | Gordon et al. | 424/260 |
| 4,464,378 A | 8/1984 | Hussain et al. | 424/260 |
| 4,573,995 A | 3/1986 | Chen et al. | 604/896 |
| 4,582,835 A | 4/1986 | Lewis et al. | 514/282 |

(Continued)

FOREIGN PATENT DOCUMENTS

| | | | |
|---|---|---|---|
| DE | 2222039 | 11/1972 | A61K 27/00 |
| DE | 432545 | 2/1995 | A61K 31/485 |

(Continued)

OTHER PUBLICATIONS

Foss, J.F., et al.Abstract, "Prevention of Apomorphine- or Cisplatin—induced emesis in the dog by combination of Methxlnaltrexone and Morphine",Cancer Chemother Pharmacol (1998); 42(4):287-91.

Yuan et al., "Efficacy of Orally Administered Methylnaltrexone in Decreasing Subjective Effects After Intravenous Morphine",Drug and Alcohol Degendence (1998); 52:161-165.

Gan et al., "Opioid-Sparing Effects of a Low-Dose Infusion of Naloxone in Patient-Administered Morphine Sulfate," Anesthesiology (1997), 87(5):1075-1080.

Shen et al., "Ultra-Low Doses of Naltrexone or Etorphine Increase Morphine's Antinociceptive Potencey and Attenuate Tolerance/Dependence in Mice," Brain Research (1997), 757:176-190.

(Continued)

*Primary Examiner* — Robert A Wax
*Assistant Examiner* — Randeep Singh
(74) *Attorney, Agent, or Firm* — Davidson, Davidson & Kappel, LLC

(57) ABSTRACT

Disclosed in certain embodiments is a dosage form comprising a plurality of extruded particles comprising an adverse agent or antagonist and a layer disposed about the particles.

20 Claims, 3 Drawing Sheets

(56) References Cited

U.S. PATENT DOCUMENTS

| | | | | |
|---|---|---|---|---|
| 4,587,118 | A | 5/1986 | Hsiao | 424/459 |
| 4,608,376 | A | 8/1986 | Pasternak | 514/282 |
| 4,661,492 | A | 4/1987 | Lewis et al. | 514/282 |
| 4,719,215 | A | 1/1988 | Goldberg | 514/282 |
| 4,730,048 | A | 3/1988 | Portoghese et al. | 546/45 |
| 4,760,069 | A | 7/1988 | Rzeszotarski et al. | 514/282 |
| 4,769,372 | A | 9/1988 | Kreek et al. | 514/282 |
| 4,785,000 | A | 11/1988 | Kreek et al. | 514/282 |
| 4,803,208 | A | 2/1989 | Pasternak | 514/282 |
| 4,806,341 | A | 2/1989 | Chien et al. | 424/448 |
| 4,806,543 | A | 2/1989 | Choi | 514/464 |
| 4,806,558 | A | 2/1989 | Wuest et al. | 514/381 |
| 4,828,836 | A | 5/1989 | Elger et al. | 424/419 |
| 4,834,965 | A | 5/1989 | Martani et al. | 424/488 |
| 4,834,984 | A | 5/1989 | Goldie et al. | 424/488 |
| 4,834,985 | A | 5/1989 | Elger et al. | 424/488 |
| 4,844,907 | A | 7/1989 | Elger et al. | 424/465 |
| 4,844,909 | A | 7/1989 | Goldie et al. | 424/480 |
| 4,844,910 | A | 7/1989 | Leslie et al. | 424/494 |
| 4,861,598 | A | 8/1989 | Oshlack et al. | 424/468 |
| 4,861,781 | A | 8/1989 | Goldberg | 514/282 |
| 4,867,985 | A | 9/1989 | Heafield et al. | 424/461 |
| 4,873,076 | A | 10/1989 | Fishman et al. | 412/10 |
| 4,882,335 | A | 11/1989 | Sinclair | 514/282 |
| 4,889,860 | A | 12/1989 | Rzeszotarski et al. | 514/282 |
| 4,935,428 | A | 6/1990 | Lewis | 514/282 |
| 4,940,587 | A | 7/1990 | Jenkins et al. | 424/480 |
| 4,957,681 | A | 9/1990 | Klimesch et al. | 264/211.23 |
| 4,970,075 | A | 11/1990 | Oshlak | 424/451 |
| 4,987,136 | A | 1/1991 | Kreek et al. | 514/282 |
| 4,990,341 | A | 2/1991 | Goldie et al. | 424/464 |
| 5,071,646 | A | 12/1991 | Malkowska et al. | 424/497 |
| 5,075,341 | A | 12/1991 | Mendelson et al. | 514/282 |
| 5,086,058 | A | 2/1992 | Sinclair et al. | 514/282 |
| 5,091,189 | A | 2/1992 | Heafield et al. | 424/457 |
| 5,096,715 | A | 3/1992 | Sinclair | 424/449 |
| 5,102,887 | A | 4/1992 | Goldberg | 514/282 |
| 5,130,311 | A | 7/1992 | Guillaumet et al. | 514/234.2 |
| 5,149,538 | A | 9/1992 | Granger et al. | 424/449 |
| 5,215,758 | A | 6/1993 | Krishnamurthy | 424/488 |
| 5,225,440 | A | 7/1993 | London et al. | 514/535 |
| 5,226,331 | A | 7/1993 | Thompson et al. | 73/865.9 |
| 5,236,714 | A | 8/1993 | Lee et al. | 424/449 |
| 5,256,669 | A | 10/1993 | Askanazi et al. | 514/282 |
| 5,266,331 | A | 11/1993 | Oshlak et al. | 424/464 |
| 5,273,760 | A | 12/1993 | Oshlack et al. | 424/486 |
| 5,286,493 | A | 2/1994 | Oshlak et al. | 424/468 |
| 5,290,560 | A | 3/1994 | Autant et al. | |
| 5,316,759 | A | 5/1994 | Rose et al. | 424/10 |
| 5,317,022 | A | 5/1994 | Borsodi et al. | 514/282 |
| 5,321,012 | A | 6/1994 | Mayer et al. | 514/25 |
| 5,324,351 | A | 6/1994 | Oshlak et al. | 106/153 |
| 5,336,691 | A | 8/1994 | Raffa et al. | 514/629 |
| 5,352,680 | A | 10/1994 | Portoghese et al. | 514/279 |
| 5,352,683 | A | 10/1994 | Mayer et al. | 514/289 |
| 5,356,467 | A | 10/1994 | Oshlak et al. | 106/153 |
| 5,356,900 | A | 10/1994 | Bihari et al. | 514/282 |
| 5,376,662 | A | 12/1994 | Ockert | 514/282 |
| 5,409,944 | A | 4/1995 | Black et al. | 514/359 |
| 5,411,745 | A | 5/1995 | Oshlack et al. | 424/456 |
| 5,426,112 | A | 6/1995 | Zagon et al. | 514/282 |
| 5,436,265 | A | 7/1995 | Black et al. | 514/420 |
| 5,451,408 | A | 9/1995 | Mezei et al. | |
| 5,457,208 | A | 10/1995 | Portoghese et al. | 546/35 |
| 5,460,826 | A | 10/1995 | Merrill et al. | 424/470 |
| 5,472,712 | A | 12/1995 | Oshlack et al. | 424/480 |
| 5,472,943 | A | 12/1995 | Crain et al. | 514/12 |
| 5,474,995 | A | 12/1995 | Ducharme et al. | 514/241 |
| 5,478,577 | A | 12/1995 | Sackler et al. | 424/489 |
| 5,486,362 | A | 1/1996 | Kitchell et al. | 424/426 |
| 5,500,227 | A | 3/1996 | Oshlack et al. | 424/476 |
| 5,502,058 | A | 3/1996 | Mayer et al. | 514/289 |
| 5,508,042 | A | 4/1996 | Oshlack et al. | 424/468 |
| 5,508,043 | A | 4/1996 | Krishnamurthy | 424/484 |
| 5,510,368 | A | 4/1996 | Lau et al. | 514/419 |
| 5,512,578 | A | 4/1996 | Crain et al. | 514/282 |
| 5,514,680 | A | 5/1996 | Weber et al. | 514/249 |
| 5,521,213 | A | 5/1996 | Prasit et al. | 514/443 |
| 5,534,492 | A | 7/1996 | Aston et al. | 514/608 |
| 5,536,752 | A | 7/1996 | Ducharme et al. | 514/602 |
| 5,549,912 | A | 8/1996 | Oshlack et al. | 424/468 |
| 5,550,142 | A | 8/1996 | Ducharme et al. | 514/365 |
| 5,552,422 | A | 9/1996 | Gauthier et al. | 514/368 |
| 5,556,838 | A | 9/1996 | Mayer et al. | 514/25 |
| 5,574,052 | A | 11/1996 | Rose et al. | 514/343 |
| 5,578,725 | A | 11/1996 | Portoghese et al. | 546/35 |
| 5,580,876 | A | 12/1996 | Crain et al. | 514/282 |
| 5,585,348 | A | 12/1996 | Crain et al. | 514/12 |
| 5,591,452 | A | 1/1997 | Miller et al. | 424/468 |
| 5,593,994 | A | 1/1997 | Batt et al. | 514/252 |
| 5,601,845 | A | 2/1997 | Buxton et al. | 424/495 |
| 5,604,253 | A | 2/1997 | Lau et al. | 514/415 |
| 5,604,260 | A | 2/1997 | Guay et al. | 514/605 |
| 5,616,601 | A | 4/1997 | Khanna et al. | 514/399 |
| 5,622,722 | A | 4/1997 | Knott et al. | 424/494 |
| 5,624,932 | A | 4/1997 | Qin et al. | 514/282 |
| 5,633,259 | A | 5/1997 | Qin et al. | 514/282 |
| 5,639,476 | A | 6/1997 | Oshlack et al. | 424/468 |
| 5,639,780 | A | 6/1997 | Lau et al. | 514/419 |
| 5,656,295 | A | 8/1997 | Oshlack et al. | 424/468 |
| 5,670,172 | A | 9/1997 | Buxton et al. | 424/495 |
| 5,672,360 | A | 9/1997 | Sackler et al. | 424/490 |
| 5,681,585 | A | 10/1997 | Oshlack et al. | 424/494 |
| 5,763,452 | A | 6/1998 | Miller et al. | 514/282 |
| 5,767,125 | A | 6/1998 | Crain et al. | 514/282 |
| 5,780,479 | A | 7/1998 | Kim | 514/282 |
| 5,811,126 | A | 9/1998 | Krishnamurthy | 424/498 |
| 5,834,024 | A | 11/1998 | Heinicke et al. | |
| 5,834,477 | A | 11/1998 | Mioduszewski | 514/282 |
| 5,843,480 | A | 12/1998 | Miller et al. | |
| 5,849,240 | A | 12/1998 | Miller et al. | |
| 5,856,332 | A | 1/1999 | Dante | |
| 5,858,017 | A | 1/1999 | Demopulos et al. | |
| 5,860,950 | A | 1/1999 | Demopulos et al. | |
| 5,866,164 | A | 2/1999 | Kuczynski et al. | |
| 5,879,705 | A | 3/1999 | Heafield et al. | 424/464 |
| 5,880,132 | A | 3/1999 | Hill | 514/282 |
| 5,891,471 | A | 4/1999 | Miller et al. | 424/468 |
| 5,908,848 | A | 6/1999 | Miller et al. | 514/282 |
| 5,942,241 | A | 8/1999 | Chasin et al. | 424/426 |
| 5,958,452 | A | 9/1999 | Oshlack et al. | 424/457 |
| 5,958,459 | A | 9/1999 | Chasin et al. | 424/490 |
| 5,965,161 | A | 10/1999 | Oshlack et al. | 424/457 |
| 5,965,163 | A | 10/1999 | Miller et al. | 424/468 |
| 5,968,547 | A | 10/1999 | Reder et al. | 424/449 |
| 5,968,551 | A | 10/1999 | Oshlack et al. | 424/456 |
| 5,972,954 | A | 10/1999 | Foss | 514/282 |
| 5,998,434 | A | 12/1999 | Mitch et al. | 514/210.16 |
| 6,004,970 | A | 12/1999 | O'Malley et al. | |
| 6,024,982 | A | 2/2000 | Oshlack et al. | 424/476 |
| 6,068,855 | A | 5/2000 | Leslie et al. | 424/468 |
| 6,077,532 | A | 6/2000 | Malkowska et al. | 424/457 |
| 6,077,533 | A | 6/2000 | Oshlack et al. | 424/461 |
| 6,096,756 | A | 8/2000 | Crain et al. | 514/282 |
| 6,103,258 | A | 8/2000 | Simon | 424/449 |
| 6,103,261 | A | 8/2000 | Chasin et al. | 424/459 |
| 6,120,806 | A | 9/2000 | Whitmire | |
| 6,143,322 | A | 11/2000 | Sackler et al. | 424/459 |
| 6,143,328 | A | 11/2000 | Heafield et al. | 424/489 |
| 6,162,467 | A | 12/2000 | Miller et al. | 424/468 |
| 6,194,382 | B1 | 2/2001 | Crain et al. | 514/2 |
| 6,210,714 | B1 | 4/2001 | Oshlack et al. | 424/476 |
| 6,228,863 | B1 | 5/2001 | Palermo et al. | 514/282 |
| 6,254,887 | B1 | 7/2001 | Miller et al. | 424/468 |
| 6,261,599 | B1 | 7/2001 | Oshlack et al. | 424/457 |
| 6,274,591 | B1 | 8/2001 | Foss et al. | |
| 6,277,384 | B1 | 8/2001 | Kaiko et al. | 424/400 |
| 6,294,195 | B1 | 9/2001 | Oshlack et al. | 424/457 |
| 6,306,438 | B1 | 10/2001 | Oshlack et al. | 424/468 |
| 6,326,027 | B1 | 12/2001 | Miller et al. | 424/468 |
| 6,335,033 | B2 | 1/2002 | Oshlack et al. | 424/457 |
| 6,362,194 | B1 | 3/2002 | Crain et al. | 514/285 |
| 6,375,957 | B1 | 4/2002 | Kaiko et al. | 424/400 |
| 6,387,404 | B2 | 5/2002 | Oshlack et al. | 424/480 |

(56) References Cited

U.S. PATENT DOCUMENTS

| | | | |
|---|---|---|---|
| 6,395,705 B2 | 5/2002 | Crain et al. | 514/2 |
| 6,399,096 B1 | 6/2002 | Miller et al. | 424/464 |
| 6,419,959 B1 | 7/2002 | Walter et al. | |
| 6,475,494 B2 | 11/2002 | Kaiko et al. | 424/400 |
| 6,552,031 B1 | 4/2003 | Burch et al. | |
| 6,627,635 B2 | 9/2003 | Palermo et al. | 514/282 |
| 6,696,066 B2 | 2/2004 | Kaiko et al. | 424/400 |
| 6,696,088 B2 | 2/2004 | Oshlack et al. | |
| 6,716,449 B2 | 4/2004 | Oshlack et al. | 424/449 |
| 6,765,010 B2 | 7/2004 | Crain et al. | |
| 7,144,587 B2 | 12/2006 | Oshlack et al. | |
| 7,172,767 B2 | 2/2007 | Kaiko et al. | |
| 7,332,182 B2 | 2/2008 | Sackler | |
| 2001/0006967 A1 | 7/2001 | Crain et al. | 514/253.04 |
| 2001/0018413 A1 | 8/2001 | Crain et al. | 514/2 |
| 2002/0010127 A1 | 1/2002 | Oshlack et al. | |
| 2002/0058673 A1 | 5/2002 | Kaiko et al. | |
| 2003/0004177 A1 | 1/2003 | Kao et al. | |
| 2003/0026839 A1 | 2/2003 | Oshlack et al. | |
| 2003/0068371 A1 | 4/2003 | Oshlack et al. | |
| 2003/0073714 A1 | 4/2003 | Breder et al. | |
| 2003/0124061 A1 | 7/2003 | Roberts | |
| 2003/0157168 A1 | 8/2003 | Breder et al. | |
| 2003/0190362 A1* | 10/2003 | Sackler | A61K 9/1658 424/478 |
| 2003/0191147 A1 | 10/2003 | Sherman et al. | |
| 2003/0069263 A1 | 11/2003 | Oshlack et al. | |
| 2003/0229111 A1* | 12/2003 | Oshlack | A61K 9/2009 514/282 |
| 2004/0092542 A1 | 5/2004 | Oshlack et al. | |
| 2004/0131552 A1* | 7/2004 | Boehm | A61K 9/2077 424/10.1 |
| 2004/0186121 A1 | 9/2004 | Oshlack et al. | |
| 2004/0192715 A1 | 9/2004 | Chasin et al. | |
| 2005/0020613 A1 | 1/2005 | Boehm et al. | |
| 2005/0095291 A1 | 5/2005 | Oshlack et al. | |
| 2005/0181046 A1 | 8/2005 | Oshlack et al. | |
| 2005/0191244 A1 | 9/2005 | Bartholomaus et al. | |
| 2005/0245483 A1 | 11/2005 | Brogmann et al. | |
| 2005/0245556 A1 | 11/2005 | Brogmann et al. | |
| 2005/0245557 A1 | 11/2005 | Schoenhard et al. | |
| 2006/0039970 A1 | 2/2006 | Oshlack et al. | |
| 2006/0182801 A1 | 8/2006 | Breder et al. | |
| 2006/0194826 A1 | 8/2006 | Oshlack et al. | |
| 2006/0269605 A1 | 11/2006 | Lizio et al. | |
| 2007/0014732 A1 | 1/2007 | Sackler | |
| 2007/0042045 A1 | 2/2007 | Lizio et al. | |
| 2007/0122348 A1 | 5/2007 | Kaiko et al. | |
| 2008/0020028 A1 | 1/2008 | Shevchuk et al. | |
| 2008/0069881 A1 | 3/2008 | Caruso et al. | |
| 2008/0233156 A1 | 9/2008 | Matthews et al. | |
| 2008/0233197 A1 | 9/2008 | Mathews et al. | |
| 2009/0131466 A1 | 5/2009 | Liang et al. | |
| 2009/0162451 A1 | 6/2009 | Mathews et al. | |
| 2010/0151014 A1 | 6/2010 | Liang et al. | |
| 2010/0152221 A1 | 6/2010 | Liang et al. | |

FOREIGN PATENT DOCUMENTS

| | | | |
|---|---|---|---|
| DE | 29719704 | 2/1997 | A61K 31/485 |
| DE | 19651551 | 6/1998 | A61K 31/485 |
| EP | 0193355 A3 | 9/1986 | A61K 31/615 |
| EP | 0205282 | 12/1986 | A61K 9/22 |
| EP | 0319243 A1 | 6/1989 | A61K 31/485 |
| EP | 0352361 | 1/1990 | A61K 31/485 |
| EP | 0319243 B1 | 11/1990 | A61K 31/485 |
| EP | 0 502 642 | 9/1992 | |
| EP | 0647448 | 4/1995 | A61K 31/485 |
| EP | 0880352 B1 | 2/1998 | A61K 31/485 |
| EP | 0913152 | 6/1999 | A61K 31/485 |
| EP | 0548448 B1 | 9/2000 | A61K 9/50 |
| RU | 2244541 | 1/2005 | |
| UA | 76069 | 6/2006 | |
| WO | 8303197 | 9/1983 | A61K 9/22 |
| WO | 8701282 | 3/1987 | A61K 31/485 |
| WO | 9004965 | 5/1990 | A61K 31/485 |
| WO | 9406426 | 3/1994 | A61K 31/46 |
| WO | 9503804 | 2/1995 | A61K 31/485 |
| WO | 9602251 | 2/1996 | A61K 31/485 |
| WO | 9733566 | 9/1997 | A61K 9/20 |
| WO | 98/18610 | 5/1998 | |
| WO | 9825613 | 6/1998 | A61K 31/485 |
| WO | 9835679 | 8/1998 | A61K 31/485 |
| WO | 9913799 A1 | 3/1999 | A61F 2/02 |
| WO | 9932120 | 7/1999 | A61K 31/485 |
| WO | 0001377 | 1/2000 | A61K 31/00 |
| WO | 0038649 | 7/2000 | A61K 9/00 |
| WO | 00051592 | 9/2000 | A61K 31/14 |
| WO | 00067739 | 11/2000 | A61K 31/00 |
| WO | 0132180 A2 | 5/2001 | A61K 31/485 |
| WO | 0137785 A2 | 5/2001 | |
| WO | 0152851 A1 | 7/2001 | A61K 31/485 |
| WO | 01/58447 A1 | 8/2001 | |
| WO | 0158451 A1 | 8/2001 | A61K 31/485 |
| WO | 0168080 A2 | 9/2001 | A61K 31/00 |
| WO | 00185150 | 11/2001 | A61K 31/00 |
| WO | 0185257 A2 | 11/2001 | |
| WO | 0193852 A2 | 12/2001 | A61K 31/00 |
| WO | 03/007802 | 1/2003 | |
| WO | 04052346 A1 | 6/2004 | A61K 9/62 |
| WO | WO 2004/091512 | 10/2004 | |
| WO | WO 2009/079518 | 6/2009 | |
| WO | WO 2009/079521 | 6/2009 | |
| WO | WO/2009/085778 | 7/2009 | |

OTHER PUBLICATIONS

Yuan et al., "The Safety and Efficacy of Oral Methylnaltrexone in Preventing Morphine-induced Delay in Oral-Cecal Transit Time", Clinical Trials and Therapeutics (1997), 61:467-475.

Mendelson J., et al., "Buprenorphine and Naloxone Interactions in Opiate Dependent Volunteers," Clin. Phar. Ther. (1996), 60:105-114.

Walsh et al., "Effects of Naltrexone on Response to Intravenous Cocain, Hydromorphone and their Combination in Humans," (1996).

Chih-Cheng Chien, et al., "Sigma Antagonists Potentiate Opioid Analgesia in Rats", Neuroscience Letters 190 (1995), 137-139.

Crain et al., "Ultra-Low Concentrations of Naloxone Selectively Antagonize Excitory Effects of Morphine on Sensory Neurons, Thereby Increasing Its Antinociceptive Potency and Attenuating Tolerance/Dependence During Chronic Cotreatment," Proc. Natl. Acad. Sci. USA (1995) 92:10540-10544.

Hanson, Analgesic, Antipyretic and Anti-Inflammatory Drugs in Remington's Science and Practice of Pharmacy (1995), 2:1207.

Talwin NX, Physician's Desk Reference 48$^{th}$ Ed. (1994) Montvale, NJ 2120-2121.

Foss et al., "Dose related Antagonism of the Emetic Effect of Morphine by Methylnaltrexone in Dogs",J. Clin Pharmacol (1993), 33:747-751.

Holmes et al., "Inhibiting Spinal Dynorphin A Component Enhances Intrathecal Morphine Antinocicption in Mice", Anesth. Analg. (1993), 77:1166-73.

Miakowski et al., "Inhibition of Spinal Opioid Analgesia by Supraspinal Administration of Selective Opioid Antagonists", Brain Research (1992), 30:263-274.

Weinhold et al., "Buprenorphine Alone and in Combination with Naltrexone in Non-Dependent Humans," Drug and Alcohol Dependence (1992), 30:263-274.

Cappel et al., "Enhancement of Naloxone Induced Analgesia by Pretreatment with Morphine" Pharma. Bioch. & Behav. (1989), 34:425-427.

Vaccarino et al.,"Analgesia Produced by Normal Doses of Opioid Antagonists Alone and in Combination with Morphine", Pain (1989), 36:103-109.

Gonzalez et al., "Naltrexone: A Review of its Pharmacodynamic and Pharmacokinetic Properties and Therapeutic Efficacy in the Management of Opioid Dependence," Drugs (1988), 35:192-213.

(56) References Cited

OTHER PUBLICATIONS

Sunshine, et al., "Analgesic Efficacy of Pentazocine Versus a Pentazocine-Naloxone Combination Following Oral Administration," Clin. J. Pain (1988), 4:35-40.
Wang et al., "Crossover and Parallel Study of Oral Analgesics," J. Clin. Pharmacol (1981), 21:162-168.
Translation of German patent application DE 43 25 465.
Alavrez-Fuentes, et al. "Effectiveness of Repeated Administration of a New Ora Naltrexone Controlled-Release System in Morphine Analgesia"; J. Pharm Pharmcaol (2001), 53:1201-1205.
Alvarez-Fuentes, et al., "Preclinical Study of an Oral Controlled Release Naltrexone Complex in Mice"; J. Pharm Pharmacol (2000), 52:659-663.
Archer, Sydney; "Historical Perspective on the Chemistry and Development of Naltrexone"; Naltrexone Research Monograph28 (1980) p. 3-9.
Baum et al., "The Impact of the Addition of Naloxone on thr Use and Abuse of Pentazocine"; Public Health Reports (1987) vol. 102, No. 4 p. 426-429.
Rapaka et al., "Discovery of Novel Opioid Medications"; NIDA Research Monograph 147 (1995) p. 55-83.
Bloom et al., "Clinical Studies with Naloxone/Methadone in a Ratio of 1:20"; 5th National Conference on Methadone Treatment (1973) vol. 2, p. 1342-1349.
Briscoe et al., "Methoclocinnamox: Time Course of Changes in Alfetnanil-Reinforced Rhesus Monkeys"; Psychopharmacology (2000) 148:393-399.
Abstract of Bromm, et al., "A Sensitive Method to Evaluate Effects of Analgesics in Man"; Meth and Find Exptl Clin Pharmacol 5 (8) (1983) p. 545-551.
Bullingham et al., "Clinical Pharamcokinetics of Narcotic Agonist-Antagonist Drugs"; Clinical Pharm (1983) 8: 332-343.
Calimlim, et al. "Effect of Naloxone on the Analgesic Activity of Methadone in a 1:10 Oral Combination"; Clin Pharmacol and There (1974) vol. 15; No. 6 pp. 556-564.
Caruso et al., "Methadone and Naloxone in Combination (Naldone®) for the Treatment if Heroin Addicts"; Bristol Laboratories, pp. 1336F-1341F.
Cherny, Nathan I., "Opioid Analgesics"; Drugs May 1996:51 (5) pp. 713-737.
Chiang, et al. "Clinical Evaluation of a Naltrexone Sustained-Release Preparation"; Drug and Alcohol Dependence (1985) 16, pp. 1-8.
Chiang et al., "Kinetics of a Naltrexone Sustained-Release Preparation"; Clin Pharmacol Thera (1984) vol. 36 No. 5, pp. 704-708.
Comer et al., "Depot Naltrexone: Long-lasting Antagonism of the Effects of Heroin un Humans"; Psychopharmacology (2002) 159, pp. 351-360.
Crabtree et al., "Review of Naltrexone, a long-acting Opiate Antagonist"; Clinical Pharmacy, vol. 3 (1984) pp. 273-280.
Crain et al., "Antagonists of Excitatory Opioid Receptor Functions Enhance Morphine's Analgesic Potency and Attenuate Opioid Tolerance/dependence liability"; Dept. of Neuroscience, Albert Einstein College of Medicine Pain 82 (1999)pp. 1-11.
Crain et al., "Antagonists of Excitatory Opioid Receptor Functions Enhance Morphine's Analgesic Potency and Attenuate Opioid Tolerance/dependence liability"; Dept. of Neuroscience, Albert Einstein College of Medicine Pain 84 (2000) pp. 121-131.
Fink et al., "Naloxone in Heroin Dependence"; Clin Pharm and Thera. vol. 9, No. 5;pp. 568-577.
Fishman et al., "Disposition of Naloxone-7,8-$^3$H in Normal & Narcotic Dependent Men"; J. Pharm. and Exper. Thera (1973)vol. 10 No. 2;pp. 575-580.
Glatt, William, M.D. FACP, "A New Method for Detoxifying Opoiod-Dependent Patients"; J. Substance Abuse Treatment (1999) vol. 17, No. 3,pp. 193-197.
Gold, et al. "Rapid Opioid Detoxification During General Anesthesia"; Anesthesiology (1999) vol. 91, No. 6, pp. 1639-1647.

Greenwald, et al., "Comparative Clinical Pharmacology of Short-Acting µU Opioids in Drug Abusers"; J. Pharm and Exper Thera (1996) vol. 277, No. 3, pp. 1228-1236.
Gupta, et al., "Morphine Combined with Doxapram or Naloxone"; Anesthesia (1974) vol. 29, pp. 33-39.
Richter et al., "Clinical Investigation on the Development of Dependence during Oral Therapy with Tramadol"; Arzniem-Forsch/Drug Res. 35 (No. II)(1985)pp. 1742-1744.
Rosen et al., "The effect of Lamotrigine on Naloxone-precipitated Opiate withdrawal"; Drug and Alcohol Dependence (1998) vol. 52, pp. 173-176.
Rosen et al., "A Pilot Study of Dextromethorphan in Naloxone-Precipitated Opiate Withdrawal"; European J. of Pharm. (1996) vol. 307, pp. 251-257.
Schuh et al., "Buprenorphine, Morphine and Naloxone Effects during Ascending Morphine Maintenance in Humans"; J. Pharm and Exper Thera (1996) vol. 278, 2, pp. 836-846.
Schuh et al., "Onset, Magnitude and Duration of Opioid Blockade Produced by Buprenorphine and Naltrexone in Humans"; Psychopharmacology (1999) vol. 145, pp. 162-174.
Stevens et al., Nonspecific Excitatory Effects of Morphine: Reverse-Order Precipitated Withdrawal and Dose-Dose Interactions: Psychopharmacology (1981) vol. 75, pp. 210-211.
Stine et al., "Reduction of Opiate Withdrawal-like Symptoms by Cocaine Abuse during Methadone and Buprenorphine Maintenance"; Am. J. Drug and Alcohol Abuse (1994) vol. 20, 4, pp. 445-458.
Stine et al., "Use of Drug Combinations in Treatment of Opiopd Withdrawal"; J. Clinical Psych. (1992) vol. 12, No. 3, pp. 203-209.
Stoller et al., "Effects of buprenorphine/naloxone in opioid-dependent humans" Psychopharmacology (2001) vol. 154, pp. 230-242.
Strain et al., "Acute Effects of Buprenorphine, hydromorphone and naloxone in methadone-maintained volunteers"; J. Pharm and Exper Thera (1992) vol. 261, No. 3, pp. 985-993.
Strain et al., "Effects of buprenorphine versus buprenorphine/naloxone tablets in non-dependent opioid abusers"; Psychopharmacology (2000) vol. 148, pp. 374-383.
Strain et al., "Precipitated Withdrawal by Pentazocine in Methadone-Maintained Volunteers"; J. Pharm and Exper Thera (1993) vol. 267, No. 2, pp. 624-634.
Tai, et al., "Naltrexone: An Antagonist Therapy for Heroin Addiction"; NIDA (1997) 5 pages.
Umbricht et al., "Naltrexone shortened opioid detoxification with buprenorphine"; Drug and Alcohol Dependence (1999) vol. 56 pp. 181-190.
Vaccarino et al., "Enogenous Opiates: 1999"; Peptides 21 (2000) pp. 1975-2034.
Wang et al., "Inverse Agonists and neutral antagonists at µ opioid receptor (MOR): possible role of basal receptor signaling in narcotic dependence"; J. Neurochemistry (2001) vol. 77, pp. 1590-1600.
Way et al., "Responsivity to Naloxone during Morphine Dependence"; Annals New York Academy of Sciences, pp. 252-261.
Weinberg et al., "Sublingual absorption of selected opioid analgesics"; Clin Pharm Thera (1988) vol. 44, No. 3, pp. 335-342.
Wells, et al., "In vivo Pharmacological Characterization of SoRI 9409, a Nonpeptidic Opioid µ-Agonist/δ-Antagonist that Produces Limited Antinociceptive Tolerance and Attenuates Morphione Physical Dependence"; J. Pharm and Exper Thera (2001) vol. 297, No. 2, pp. 597-605.
Wodak, Alex, "Drug Treatment for Opioid Dependence"; Australian Prescriber (2001) vol. 24, No. 1, pp. 4-6.
Wright et al., "Acute physical dependence in Humans; repeated naloxone-precipitated withdrawal after a single-dose of methadone"; Drug and Alcohol Dependence (1991) vol. 27, pp. 139-148.
Zhu et al., "Naltrexone-precipitated morphine withdrawal in infant rat is attenuated by acute administration if NOS inhibitors but not NMDA receptor antagonists"; Psychopharmacology (2000) vol. 150, pp. 325-336.
Han et al., "Muccoadhesive buccal disks for novel nalbuphine prodrug controlled delivery; effect of formulation variable on drug release and mucoadhesive performance"; International J. Pharm (1999) vol. 177, pp. 201-209.

(56) References Cited

OTHER PUBLICATIONS

Handal et al., "Naloxone"; Annals of Emergency Medicine (1983) vol. 12:7, pp. 438-445.
Harris et al., "Buprenorphine and Naloxone co-administration in opiate dependent patients stabilized on sublingual buprenorphine"; Drug and Alcohol Dependence (2000) vol. 61, pp. 85-94.
Hawkes et al., "Effect of enteric-release formulation of naloxone on intestinal transit in volunteers taking codeine"; Aliment Pharm Ther (2001) vol. 15, pp. 625-630.
Högger et al., "Comparison of tilidine/naloxone, tramadol and bromfenac in experimental pain: a double-blind randomized crossover study in healthy human volunteers"; International J. Clin Pharm and Thera (1999) vol. 37, No. 8,pp. 377-385.
Budd, Keith, "Clinical Use of Opioid Antagonists"; Bailliere's Clinical Anesthesiology (1987) vol. 1, No. 4, pp. 993-1011.
Crain et al., Ultra-low concentrations of naloxone selectively antagonize excitatory effects of morphine on sensory neurons, thereby increasing its antinociceptive potency and attenuating tolerance/dependence.
Howes et al., "The Pharmacology of TR5109, a new Narcotic Agonist/Antagonist Analgesic"; NIDA Research (1979) pp. 99-105.
Leeling et al., "Disposition and metaboliam of codorphone in the rat, dog, and man"; Drug Metabolism and Disposition (1982) vol. 10, No. 6, pp. 649-653.
Amass et al., "Efficacy of daily and alternate-day dosing regimens with the combibation buprenorphine-naloxone tablet"; Drug and Alcohol Dependence (2000) vol. 58, pp. 143-152.
Hassain et al., "Buccal and oral bioavailability of naloxone and naltrexone in rats";(1987) vol. 36, pp. 127-130.
Jasinski et al., "The human pharmacology and abuse potential of N-allylnoroxymorphone naloxone"; J. Pharm and Exper Thera (1967) vol. 157, No. 2, pp. 420-426.
Jones et al., "Nalmefene:blockade of intravenous morphine challenge effects in opioid abusinh humans"; Drug and Alcohol Dependence (2000) vol. 60, pp. 29-37.
Kanof et al., "Clinical Charateristics of Naloxone-Precipitated Withdrawal in Human Opioid-Dependent Subjects"; J Pharma and Exper Thera (19920 vol. 260, No. 1, pp. 355-363.
King et al., "Naltrexone Biotransformation and Incidence of Subjective Side Effects: A Preliminary Study"; Alcoholism: Clin and Exper Res (1997) vol. 21, No. 5, pp. 906-909.
Kogan et al., "Estimation of the Systemic Availability and Other Pharmacokinetic Parameters of Naltrexone in Man after Acute and Chronic Oral Administration"; Res. Comm. in Chem. Path. and Pharm (1977) vol. 18, No. 1, pp. 29-34.
Kosten, Thomas R., M.D.,"Buprenorphine for Benzodiazepine-Abusing Heroin Addicts"; Amer J of Phsychiatry (1994) vol. 1, p. 151.
Kosten et al., "Opioid antagonist challenges in buprenorphine maintained patients"; Drug and Alcohol Dependence (1990) vol. 25, OO. 73-78.
Kurland et al., "Naloxone and the Narcotic Abuser: A Controlled Study of Partial Blockade"; Inter. J. of the Addictions (1974) vol. 9, No. 5, pp. 663-672.
Lee et al., "Nalbuphine Coadministered with Morphine Prevents Tolerance and Dependence"; Anesth Analg (1997) vol. 84, pp. 810-815.
Lehman, et al.,"Influence of Naloxone on the Postoperative Analgesic and Respiratory effects of Buprenorphine"; Eur. J. Clin Pharm (1988) vol. 34, pp. 343-352.
Levine et al., "Potentiation of Pentazocine Analgesia by Low-dose Naloxone"; J Clin Invest (1988) vol. 82, pp. 1574-1577.
Loimer et al., "Combined Naloxone/Methadone Preparations for Opiate Substitution Therapy"; J. of Substance Abuse Treatment (1991) vol. 8, pp. 157-160.
Martin et al. "Bioavailability Investigation of a New Tilidine/Naloxone Liquid Formulation Compared to a Reference Formulation"; Arzneim-Forsch./Drug Res. (1999) vol. 49, pp. 599-607.

Martin et al., "Demonstration of Tolerance to and Physical Dependence on N-allynormorphine (Nalorphine)";J. of Pharm and Exper Thera (1965) vol. 150, No. 3. pp. 437-442.
Mendelson et al., "Buprenorphine and naloxone combinations: the effects of three dose ratios in morphine stabilized, opiate-dependent volunteers"; Psychopharmacology (1999) vol. 141, pp. 37-46.
Mendelson et al., "Buprenophine and naloxone Interactions in Methadone Maintenance Patients"; Society of Biological Psychiatry (1997) vol. 41, pp. 1095-1101.
Nutt et al., "Methadone-naloxone mixture for use in methadone maintenance programs"; Clin Pharm and Ther. vol. 15, No. 2., pp. 156-166.
Parwatikar et al., "Methadone-naloxone in combination for the Treatment of Heroin Addicts"; Clin. Pharm and Thera, vol. 14, No. 6, pp. 941-948.
Parwartikar et al., "Naloxone-Methadone Combination for the Treatment of Opiate Dependence"; Missouri Institute of Psychiatry, pp. 1350-1354.
Pitts et al., "Antinociceptive and Response Rate-Altering Effects of Kappa Opioid Agonists, Spiradoline, Enadoline and U69,593, Alone and in Combination with Opioid Antagonists in Squirrel Monkeys"; J of Pharm and Exper Thera (1994) vol. 271, No. 3, pp. 1501-1508.
Preston et al., "Buprenorphine and Naloxone alone and in combination in Opioid-dependant Humans"; Psychopharmacology (1988), vol. 94, pp. 484-490.
Preston et al., "Differential Naltrexone Antagonism of Hydromorphone and Pentazocine Effects in Human Volunteers"; J of Pharm and Ezper Thera (1993) vol. 264, No. 2 pp. 813-823.
Preston et al., "Effects of Sublingually given naloxone in Opioid—dependant human volunteers"; Drug and Alcohol Dependence (1990) vol. 25, pp. 27-34.
Bigelow et al., "Abuse Liability and Assessment of Buprenorphine-Naloxone Combinations"; Dept of Psychiatry and Behavioral Sciences, the Johns Hopkins University School of Medicine, pp. 145-149.
Wikler et al., "N-Allylnormorphine: Effects of single dose and Precipitation of Acute "Abstinence Syndromes" during addiction to morphine, methadone or heroin in man (post addicts)"; N-Allylnormorphine During Narcoctic Addiction (1953) pp. 8-20.
Zaks et al., "Naloxone Treatment of Opiate Dependence"; JAMA (1971) vol. 215, No. 13, pp. 2108-2110.
Barton, et al., "Intranasal Administration of Naloxone by Paramdeics";Prehospital Emergency Care (2002) vol. 6, No. 1, pp. 54-58.
Blachly, Paul, H., M.D., "Naloxone in Opiate Addiction"; Current Psychiatric Therapies (1976) pp. 209-213.
Bashaw et al., "Relative bioavailability of controlled-release oral morphine sulfate during naltrexone blockade"; Inter J of Clin Pharm and Thea (1995) vol. 33, No. 9, 524-529.
Jasinski, D.R., "Assessment of the Abuse Poteniality of Morphine-like Drugs (Methods Used in Man)"; Drug Addiction (1977) pp. 197-258.
Johnson et al., "Buprenorphine and Naloxone for Heroin Dependence"; Substance Use Disorders (2000) pp. 519-526.
Strain et al., "Opioid antagonist effects of dezocine in opioid-dependent humans"; Clin Pharm and Thera (1996) vol. 60, No. 2, pp. 206-217.
Preston et al., "Abuse liability and studies of opioid agonist-antagonists in humans"; Drug and Alcohol Dependence (1991) vol. 28, pp. 49-82.
Brennscheidt et al., "Pharmacokinetics of Nortilidine and Naloxone after Administration of Tilidine/Naloxone Solution or Tilidine/Naloxone Sustained Release Tablets"; Arzeim-Forsch/Drug Res. (2000) vol. 50, pp. 1015-1022.
Benfey, "Function of Myocardial a-Adrenoceptors" ; Life Sciences (1982) vol. 31, pp. 101-112.
Levine et al., "Potentiation of Pentazocine Analgesia by Low-dose Naloxone"; J of Clin Invest. (1988) vol. 82, pp. 15471577.
Yoburn et al., "Opioid Antagonist-induced Receptor Upregulation: Effects of Concurrent Agonist Administration"; Brain Research Bulletin (1994), vol. 33, pp. 237-240.

(56) References Cited

OTHER PUBLICATIONS

Bunzow et al., "Molecular Closing and Tissue Distribution of a Putative Member of the Rat Opioid Receptor Gene Family that is not a µ, γ, or κ opioid receptor type"; FEBS letters (1994) pp. 284-288.
Mollereau et al., "ORL 1, a novelmember of the opioid receptor family: Cloning, functional expression and localization"; FEBS letters 341 (1994), pp. 33-38.
Wang, et al., "cDNA cloning a=of an orphan opiate receptor gene family member and its splice variant"; FEBS letters 348 (1994) pp. 75-79.
Suzuki et al., "Morphine conditioned place preference after chronic treatment with naloxone in the rat"; Research Communications in Substance Abuse (1991) vol. 12., No. 3., pp. 119-131.
Press Release "International Patent Application to Be Published on Abuse-Resistant Pain Reliever Being Developed by Perdue Pharma"; Aug. 8, 2001.
Paronis et al., "Increased Analgesic Potency of Mu Agonists after Continuous Naloxone Infusion in Rats"; J fo Pharm Exper Thera (1991), 259 (2), pp. 582-589.
Yoburn et al., "Supersensitivity to Opioid Analgesics Following Chronic Opioid Antagonist Treatment: Relationship to Receptor Sensitivity"; Pharmacology Bio Beh (1995) vol. 51 No. 2, pp. 535-539.
Crain et al., "Acute thermal hyperalgesia elicited by low-dose morphine in normal mice is blocked by ultra-low-dose naltrexone, unmasking potent opioid analgesia"; Brain Research (2001) vol. 888, pp. 75-82.
Zhang et al., "Down-Regulation of µ-Opioid Receptors in Rat and Monkey Dorsal Root Ganglion Neurons and Spinal Cord After Peripheral Axotomy"; Neuroscience (1998) vol. 82., pp. 223-240.
Abdulla et al., "Axotomy reduces the effect of analgesic opioids yet increases the effect of nociceptin on dorsal root ganglion neurons"; J of Neuro Sci (1998) vol. 18, pp. 9685-9694.
Di Giannuario et al., "Orphanin FQ reduces morphine-induced dopamine release in the nucleus accumbens: a microdialysis study in rats"; Neurosci. Lett (1999) vol. 272 pp. 183-186.
Ciccocioppo et al., "Effect of Nociceptin/orphanin FQ on the Rewarding Properties of Morphine"; Eur. J Pharmacol (2000) vol. 404, pp. 153-159.
Physician's Desk Reference (2001) see Revia, pp. 1146-1149 and Oxycontin, pp. 2697-2701.
Johnson et al., "Relative bioavailabilty of plasma naltrexone from crushed ALO-01 (an investigational, abuse-deterrent, extended-release morphine sulphate formulation with sequestered naltrexone) to a naltrexone oral solution," J Pain, 2008, 9 (Suppl R), P35, Abstract 230.
Alpharma Pharmaceuticals, "ALO-01 (Morphine Sulphate Extended-Release with Sequestered Naltrexone Hydrochloride) Capsules for the Management of Moderate to Severe Pain when a Continuous, Around-the-Clock Opioid Analgesic is Needed for an Extended Period of Time," Meeting of the Anesthetic and Life Support Drugs Advisory Committee, Nov. 14, 2008.
Johnson et al., "Morphine release profile in a formulation containing polymer-coated extended-release morphine sulfate plus sequestered naltrexone," J Pain, 2007, S40, Abstract 757.
Accelerated Examination Support Document for Petition to Make Special under Accelerated Examination Program filed in U.S. Appl. No. 12/399,923 on Mar. 6, 2009.
Bodmeier et al., "The Influence of Buffer Species and Strength on Diltiazem HCI Release from Beads Coated with the Aqueous Cationic Polymer Dispersions, Eudragit RS, RL 30D," Pharmaceutical Research, vol. 13, No. 1 (1996), pp. 52-56.
Knop et al., "Influence of surfactants of different charge and concentration on drug release from pellets coated with an aqueous dispersion of quaternary acrylic polymers," S.T.P. Pharma Sciences 7 (6) (1997), pp. 507-512.
Felton et al., "Influence of Insoluable Excipients on Film Coating Systems," Drug Development and Industrial Pharmacy, 28 (3) (2002), pp. 225-243.
Wagner et al., "Influence of chloride ion exchange on the permeability and drug release of Eudragit RS 30 D films," Journal of Controlled Release, 82 (2002), pp. 385-397.
Pakkanen, Jukka S., "Academic Dissertation: Upregulation and Functionality of Neuronal Nicotinic Acetylcholine Receptors," Division of Pharmacology and Toxicology, Faculty of Pharmacy, University of Helsinki, (2006).
Notice of Opposition issued in connection with corresponding Pakistan Patent No. 140 330 on Jun. 9, 2010.
English Translation of the Office Action dated Feb. 1, 2008, in corresponding Ukrainian application No. 200511009.
English Translation of the Office Action dated Apr. 27, 2007, in corresponding Russian Application No. 200501586.
Counter-Statement filed in connection with corresponding Pakistan Application No. 277/2004 on Aug. 7, 2010.
European Search Report issued in connection with corresponding European application No. 10 001 414.1 dated Sep. 16, 2010.
Summons to attend oral proceedings pursuant to Rule 115(1) EPC issued on Aug. 23, 2012, in connection with European Application No. 04759980.8-1216.
Communication of Notice of Opposition dated Jan. 5, 2011, in connection with European Patent Application No. 04759980.8.
English Translation of the Opposition Brief filed by ACINO Pharma AG on Nov. 24, 2011, in connection with European Patent Application No. 04759980.8, the Opposition Brief included with the Communication of Notice of Opposition issued on Jan. 5, 2011 in connection with European Patent Application No. 04759980.8 (document A18).

\* cited by examiner

Dose-Adjusted Plasma Concentration Over Time Naltrexone for Example 1

PHARMACEUTICAL PRODUCTS

This application is a continuation of U.S. patent application Ser. No. 10/827,623, filed on Apr. 19, 2004, which claims priority to U.S. Provisional No. 60/464,323 filed on Apr. 21, 2003, the disclosures of which are hereby incorporated by reference in their entireties.

BACKGROUND OF THE INVENTION

Pharmaceutical products are sometimes the subject of abuse. For example, a particular dose of opioid agonist may be more potent when administered parenterally as compared to the same dose administered orally. Some formulations can be tampered with to provide the opioid agonist contained therein available for illicit use. Controlled release opioid agonist formulation are sometimes crushed by drug abusers to provide the opioid contained therein available for immediate release upon oral or parenteral administration.

Opioid antagonists have been combined with certain opioid agonists to deter the parenteral abuse of the opioid agonists. In the prior art, the combination of immediate release pentazocine and naloxone has been utilized in tablets available in the United States, commercially available as Talwin® Nx from Sanofi-Winthrop. Talwin® Nx contains immediate release pentazocine hydrochloride equivalent to 50 mg base and naloxone hydrochloride equivalent to 0.5 mg base. A fixed combination therapy comprising tilidine (50 mg) and naloxone (4 mg) has been available in Germany for the management of pain since 1978 (Valoron®N, Goedecke). A fixed combination of buprenorphine and naloxone was introduced in 1991 in New Zealand (Temgesic® Nx, Reckitt & Colman) for the treatment of pain.

Purdue Pharma L.P. currently markets sustained-release oxycodone in dosage forms containing 10, 20, 40 and 80 mg oxycodone hydrochloride under the tradename OxyContin.

U.S. Pat. Nos. 5,266,331; 5,508,042; 5,549,912 and 5,656,295 disclose sustained release oxycodone formulations.

U.S. Pat. No. 5,472,943 to Crain, et al. describes methods of enhancing the analgesic potency of bimodally acting opioid agonists by administering the agonist with an opioid antagonist.

U.S. Pat. Nos. 6,277,384; 6,475,494; and 6,375,957 to Kaiko et al.; and U.S. Pat. No. 6,228,863 to Colucci et al. are directed to decreasing the abuse potential associated with opioid analgesic dosage forms.

PCT Publication No. WO 01/58451 entitled "Tamper Resistant Oral Opioid Agonist Formulations," is directed to decreasing the abuse potential associated with opioid analgesic dosage forms by the inclusion of a sequestered opioid antagonist in an opioid agonist dosage form.

There continues to exist a need in the art for an oral dosage form comprising an opioid agonist which has decreased abuse potential.

All references cited herein, including the foregoing, are hereby incorporated by reference in their entireties.

OBJECTS AND SUMMARY OF THE INVENTION

It is an object of the present invention to provide an oral dosage form comprising an opioid antagonist that substantially prevents the release of the opioid antagonist.

It is an object of certain embodiments of the invention to provide an oral dosage form comprising an opioid antagonist formulation that is useful for decreasing the potential for abuse of an opioid agonist.

It is an object of certain embodiments of the invention to provide an oral dosage form comprising an opioid antagonist formulation that is useful for decreasing the potential abuse of an opioid agonist without affecting the analgesic effects of the opioid agonist or incurring the possibility of precipitating withdrawal.

It is an object of certain embodiments of the invention to provide an oral dosage form containing an effective dose of an opioid agonist and a dose of opioid antagonist which does not change or does not substantially change the analgesic efficacy of the opioid agonist when the dosage form is orally administered intact. However, if the dosage form is tampered with, the opioid antagonist is substantially released and can prevent abuse by interfering with the effect of the opioid agonist.

It is an object of certain embodiments of the invention to provide an oral dosage form containing an effective dose of an opioid agonist in controlled release form which does not liberate all of the agonist available for immediate release when the dosage form is tampered with.

It is an object of certain embodiments of the invention to provide an oral dosage form containing opioid agonist particles and sequestered antagonist particles wherein the agonist particles and the antagonist particles are similar, e.g., in appearance, texture, smell, taste, hardness, shape, size and/or a combination thereof, or are virtually indistinguishable from each other by one or more of these properties.

It is an object of certain embodiments of the invention to provide a method for preventing abuse of an oral dosage form comprising an opioid agonist by including in the dosage form an opioid antagonist which is sequestered, e.g., is not bioavailable when the dose is administered intact, but is bioavailable when the dosage form is tampered with (e.g., in an attempt to misuse the dose of opioid agonist).

It is an object of certain embodiments of the invention to provide a method of treating pain in human patients comprising administering an oral dosage form of an opioid agonist having reduced potential for misuse by the oral, parenteral, intranasal and/or sublingual route.

The above objects, among others, are achieved by the present invention, which is directed in part to a dosage form comprising a plurality of particles, e.g., extruded particles, each of the particles comprising an opioid antagonist dispersed in a matrix; and a layer disposed about each of the particles, wherein the matrix and the layer serve to sequester, (i.e., prevent the release or the substantial release of) the opioid antagonist in the dosage form upon exposure to an environmental fluid.

In certain embodiments, the matrix comprises a hydrophobic material. In certain other embodiments, the layer comprises a hydrophobic material.

In certain embodiments, the present invention is directed to a pharmaceutical oral dosage form comprising a) a particle, e.g., an extruded particle, comprising an opioid antagonist dispersed in a first hydrophobic material; and b) a layer comprising a second hydrophobic material disposed about the particle, the second hydrophobic material comprising, e.g., from about 2% to about 30% of the weight of the particles. Alternatively, the second hydrophobic material comprises from about 5% to about 25%, from about 10% to about 20%, from about 10% to about 25%, from about 15% to about 25%, from about 22% to about 28%, or from about 5% to about 15% of the weight of the particles.

In certain embodiments, the invention is directed to a pharmaceutical oral dosage form comprising a) a plurality of particles, e.g., extruded particles, comprising an opioid antagonist dispersed in a first hydrophobic material and a layer comprising a second hydrophobic material disposed about each of the particles, the second hydrophobic material comprising, e.g., from about 2% to about 30% of the weight of the particles; b) a plurality of particles comprising an opioid agonist dispersed in a third hydrophobic material; and c) a capsule containing the plurality of opioid agonist particles and the plurality of opioid antagonist particles. Alternatively, the second hydrophobic material comprises from about 5% to about 25%, from about 10% to about 20%, from about 10% to about 25%, from about 15% to about 25%, from about 22% to about 28%, or from about 5% to about 15% of the weight of the particles.

In certain embodiments, the present invention is further directed to a dosage form comprising a plurality of particles comprising a first matrix and an opioid agonist; and a plurality of particles, (e.g., extruded particles) comprising a second matrix and an opioid antagonist, and a layer disposed about each of the particles comprising the opioid antagonist, wherein the second matrix and the layer serve to sequester the opioid antagonist upon exposure to an environmental fluid.

In certain embodiments, the matrix of the opioid antagonist particles comprises a hydrophobic material. In certain other embodiments, the layer on the opioid antagonist particles comprises a hydrophobic material. In certain embodiments, both the matrix and the layer comprise a hydrophobic material.

In certain embodiments, a layer is disposed about the opioid agonist containing particles to make the opioid agonist particles similar in appearance to or virtually indistinguishable from the opioid antagonist containing particles, thereby reducing the ability for an abuser to physically separate the antagonist containing particles from the agonist containing particles. The agonist layer can be a functional layer in order to provide controlled release or to augment controlled release. Alternatively, the agonist layer can be a non-functional layer, e.g., a film coat, that provides no controlled release capabilities.

In certain embodiments, the invention is directed to an oral dosage form comprising (i) a plurality of particles comprising an opioid agonist in releasable form and (ii) a plurality of particles, e.g., extruded particles, comprising a matrix comprising a hydrophobic material, an opioid antagonist dispersed in the matrix, and a layer comprising a hydrophobic material disposed about the particles, such that the matrix and the layer prevent or substantially prevent the release of the antagonist when the dosage form is administered intact to a patient.

In certain embodiments of the invention, the ratio of the amount of antagonist released from the dosage form after tampering to the amount of the antagonist released from the intact dosage form based on the dissolution at 1 hour of the dosage form in 700 ml of Simulated Gastric Fluid, (SGF) using a USP Type II (paddle) apparatus at 50 rpm at 37 degrees C. is about 20:1 or greater; about 50:1 or greater; about 100:1 or greater; about 150:1 or greater; or about 1000:1 or greater.

In certain embodiments of the invention, the ratio of the amount of antagonist released from the dosage form after tampering to the amount of the antagonist released from the intact dosage form based on the dissolution at 2 hours, 4 hours, 12 hours, 24 hours and/or 36 hours of the dosage form in 700 ml of SGF using a USP Type II (paddle) apparatus at 50 rpm at 37 degrees C. for the first hour, followed by a switch to 900 ml of Simulated Intestinal Fluid, (SIF) thereafter, is about 20:1 or greater; about 50:1 or greater; about 100:1 or greater; about 150:1 or greater; or about 1000:1 or greater.

In certain embodiments of the invention, the weight percent of antagonist released from the intact dosage form based on the dissolution at 1 hour of the dosage form in 700 ml of SGF using a USP Type II (paddle) apparatus at 50 rpm at 37 degrees C. is less than 1.0%; less than 0.5%; less than 0.2%; or less than 0.1% by weight.

In certain embodiments of the invention, the weight percent of antagonist released from the intact dosage form based on the dissolution at 2 hours of the dosage form in 700 ml of SGF using a USP Type II (paddle) apparatus at 50 rpm at 37 degrees C. for the first hour, followed by a switch to 900 ml of SIF thereafter, is less than 2.0%; less than 1.0%; less than 0.5%; or less than 0.25%.

In certain embodiments of the invention, the weight percent of antagonist released from the intact dosage form based on the dissolution at 4 hours of the dosage form in 700 ml of SGF using a USP Type II (paddle) apparatus at 50 rpm at 37 degrees C. for the first hour, followed by a switch to 900 ml of SIF thereafter, is less than 2.2%; less than 1.5%; less than 1.0%; or less than 0.75%.

In certain embodiments of the invention, the weight percent of antagonist released from the intact dosage form based on the dissolution at 12 hours of the dosage form in 700 ml of SGF using a USP Type II (paddle) apparatus at 50 rpm at 37 degrees C. for the first hour, followed by a switch to 900 ml of SIF thereafter, is less than 3.0%; less than 1.8%; less than 1.25%; or less than 0.3%.

In certain embodiments of the invention, the weight percent of antagonist released from the intact dosage form based on the dissolution at 24 hours of the dosage form in 700 ml of SGF using a USP Type II (paddle) apparatus at 50 rpm at 37 degrees C. for the first hour, followed by a switch to 900 ml of SIF thereafter, is less than 4.8%; less than 2.5%; less than 1.8%; or less than 0.4%.

In certain embodiments of the invention, the weight percent of antagonist released from the intact dosage form based on the dissolution at 36 hours of the dosage form in 700 ml of SGF using a USP Type II (paddle) apparatus at 50 rpm at 37 degrees C. for the first hour, followed by a switch to 900 ml of SIF thereafter, is less than 7.0%; less than 6.5%; less than 3.0%; or less than 1.5%.

In certain embodiments of the invention, the intact dosage form releases 1.0% or less antagonist at 1 hour, 2.0% or less antagonist at 2 hours, 2.2% or less antagonist at 4 hours, 3.0% or less antagonist at 12 hours, 4.8% or less antagonist at 24 hours, and 7.0% or less antagonist at 36 hours, based on dissolution of the dosage form in 700 ml of SGF using a USP Type II (paddle) apparatus at 50 rpm at 37 degrees C. for the first hour, followed by a switch to 900 ml of SIF thereafter.

In certain embodiments of the invention, the intact dosage form releases 0.5% or less antagonist at 1 hour, 1.0% or less antagonist at 2 hours, 1.5% or less antagonist at 4 hours, 1.8% or less antagonist at 12 hours, 2.5% or less antagonist at 24 hours and 6.5% or less antagonist at 36 hours based on dissolution of the dosage form in 700 ml of SGF using a USP Type II (paddle) apparatus at 50 rpm at 37 degrees C. for the first hour, followed by a switch to 900 ml of SW thereafter.

In certain embodiments of the invention, the intact dosage form releases 0.2% or less antagonist at 1 hour, 0.5% or less antagonist at 2 hours, 1.0% or less antagonist at 4 hours, 1.25% or less antagonist at 12 hours, 1.8% or less antagonist at 24 hours, and 3.0% or less antagonist at 36 hours based on dissolution of the dosage form in 700 ml of SGF using a USP Type II (paddle) apparatus at 50 rpm at 37 degrees C. for the first hour, followed by a switch to 900 ml of SW thereafter.

In certain embodiments of the invention, the intact dosage form releases 0.1% or less antagonist at 1 hour, 0.25% or less antagonist at 2 hours, 0.75% or less antagonist at 4 hours, 0.3% or less antagonist at 12 hours, 0.4% or less antagonist at 24 hours, and 1.5% or less antagonist at 36 hours based on dissolution of the dosage form in 700 ml of SGF using a USP Type II (paddle) apparatus at 50 rpm at 37 degrees C. for the first hour, followed by a switch to 900 ml of SIF thereafter.

In certain embodiments of the invention, the weight percent of agonist released from the dosage form after tampering based on the dissolution at 1 hour of the dosage form in 700 ml of SGF using a USP Type II (paddle) apparatus at 50 rpm at 37 degrees C. is less than 50%, less than 40%, or less than 35%.

In certain embodiments of the invention, the ratio of the mean Cmax of antagonist provided after single dose administration of a tampered dosage form to a patient population, to the mean Cmax of the antagonist provided after single dose administration of an intact dosage form to a patient population is about 20:1 or greater; about 50:1 or greater; about 75:1 or greater; about 100:1 or greater; about 125:1 or greater; about 150:1 or greater; or about 1000:1 or greater. These values are preferably in the fasted state.

In certain embodiments of the invention, the ratio of the mean Cmax of antagonist provided after single dose administration of a tampered dosage form to a patient population, to the mean Cmax of the antagonist provided after single dose administration of an intact dosage form to a patient population is from about 20:1 to about 1000:1; from about 20:1 to about 150:1; about 20:1 to about 125:1; from about 20:1 to about 100:1; from about 20:1 to about 75:1; or from about 20:1 to about 50:1. In other embodiments, the range is from about 50:1 to about 1000:1; from about 75:1 to about 1000:1; from about 100:1 to about 1000:1; from about 125:1 to about 1000:1; or from about 150:1 to about 1000:1. These values are preferably in the fasted state.

In certain embodiments of the invention, the ratio of the mean AUC of antagonist provided after single dose administration of a tampered dosage form to a patient population, to the mean AUC of the antagonist provided after single dose administration of an intact dosage form to a patient population is about 5:1 or greater; about 25:1 or greater; about 75:1 or greater; about 100:1 or greater; about 150:1 or greater; about 200:1 or greater or about 250:1 or greater. These values are preferably in the fasted state.

In certain embodiments of the invention, the ratio of the mean AUC of antagonist provided after single dose administration of a tampered dosage form to a patient population, to the mean AUC of the antagonist provided after single dose administration of an intact dosage form to a patient population is from about 5:1 to about 250:1; from about 5:1 to about 200:1; from about 5:1 to about 150:1; from about 5:1 to about 100:1; from about 5:1 to about 75:1; or from about 5:1 to about 25:1. In other embodiments, the range is from about 25:1 to about 250:1; from about 75:1 to about 250:1; from about 100:1 to about 250:1; from about 150:1 to about 1000:1; or from about 200:1 to about 250:1. These values are preferably in the fasted state.

In certain embodiments, the invention is further directed to methods of preventing abuse of an opioid agonist utilizing the dosage forms disclosed herein, wherein if the dosage form is subjected to tampering and administered orally, intranasally, parenterally and/or sublingually, the effects of the opioid agonist are substantially or completely blocked by release of the opioid antagonist.

In certain embodiments, the invention is further directed to methods of treating pain by administering, e.g., orally, any of the embodiments of the invention disclosed herein comprising an analgesic to a patient in need thereof.

In embodiments wherein the plurality of particles comprising the opioid agonist and the plurality of particles comprising the opioid antagonist are similar to, or virtually indistinguishable from each other, the similarity or virtual indistinguishability of the particles can be due to (i) functional or non-functional layers, (ii) similar methods of preparation which do not have to be layered, (iii) different methods of preparation which result in similar or virtually indistinguishable final products, (iv) different methods of preparation which result in different final products which are then subjected to an additional processing step (e.g., layering) to provide the similarity or virtual indistinguishability, (v) or any other method which results in the desired properties (e.g., appearance, texture, smell, taste, hardness, shape, size, etc.).

In certain preferred embodiments, the mean diameter of the particles is from about 0.1 to about 12 mm; from about 0.1 to about 2.5 mm; from about 0.2 to about 6 mm; from about 0.5 to about 3 mm; from about 0.5 mm to about 2 mm; or from about 1 mm to about 2 mm.

The amount of opioid antagonist released, if any, upon administration of the intact dosage form is in an amount such that the dosage form remains analgesically effective.

In certain embodiments of the present invention, the ratio of the opioid agonist to the sequestered opioid antagonist is from about 1:1 to about 50:1 by weight; preferably from about 1:1 to about 20:1 by weight; or from about 15:1 to about 30:1 by weight. The weight ratio of the opioid agonist to opioid antagonist refers to the weight of the active ingredients. For example, the weight of the opioid antagonist excludes the weight of the layer and matrix which together serve to sequester the opioid antagonist. In certain preferred embodiments, the weight ratio of agonist to sequestered antagonist is from about 1:1 to about 10:1 by weight.

The oral dosage forms of the present invention containing an opioid agonist in combination with a substantially non-releasable form of an opioid antagonist include, but are not limited to, tablets and capsules. The oral dosage forms of the present invention may include any desired pharmaceutical excipients known to those skilled in the art. The oral dosage forms may provide for an immediate release of the opioid agonist and/or a controlled release of the opioid agonist.

The abuse-resistant dosage forms of the present invention are useful in connection with controlled release dosage forms which comprise a dose of opioid agonist intended to be released over an extended period of time. Drug abusers may take such controlled-release products and crush, grind, extract or otherwise damage the product with the intent of releasing the full contents of the dosage form for immediate absorption. Since tampering of the dosage form of the invention results in the opioid antagonist also becoming available for absorption, the present invention provides a means for frustrating such abuse.

The invention is also directed to a method of treating pain with a dosage form disclosed herein. The method can comprise providing an oral dosage form containing an opioid agonist in a releasable form and a sequestered antagonist as disclosed herein and orally administering the intact oral dosage form to a mammal (e.g., a human) in need of such treatment.

In certain embodiments, the invention is further directed to methods of preparing the oral dosage forms disclosed herein. In certain embodiments, the invention comprises a method of preparing an oral dosage form comprising preparing by extrusion, a plurality of particles comprising an opioid antagonist dispersed in a matrix comprising a hydrophobic material; and disposing a layer comprising a hydrophobic material about the extruded particles, wherein the matrix and layer serve to sequester the antagonist when the dosage form is administered intact. The method can further comprise combining the sequestered antagonist with a releasable form (e.g., controlled release) of an opioid agonist in a manner that maintains the integrity of the sequestered antagonist. In all embodiments of the invention, the hydrophobic material of the matrix may or may not be the same as the hydrophobic material of the layer.

Although the preferred embodiments of the invention comprise an opioid antagonist in a form that completely prevents the release of the opioid antagonist, the invention also includes an antagonist in a substantially non-releasable form. The terms "substantially not released" and "substantially non-releasable" refer to the antagonist that might be released in a small amount, as long as the amount released does not affect, or does not significantly affect, analgesic efficacy when the dosage form is orally administered to humans as intended.

In the sequestered antagonist particles there are several possibilities according to the present invention. Firstly, the matrix is capable of sequestering the antagonist somewhat without the layer and the layer enhances the sequestration. Secondly, the layer is capable of sequestering the antagonist somewhat without the matrix, and the matrix enhances the sequestration. Thirdly, the matrix is incapable of sequestering the antagonist without the layer, the layer is incapable of sequestering the antagonist without the matrix, and the matrix and the layer together are capable of sequestering the antagonist (e.g., the matrix and the layer each are capable of providing a controlled release of the antagonist individually, but the matrix and the layer together in the same dosage form sequester the antagonist). In the first and second possibilities, the matrix and/or layer enhance sequestration by being capable of providing a controlled release of the antagonist individually.

In certain preferred embodiments of the invention, the substantially non-releasable form of the antagonist is resistant to laxatives (e.g., mineral oil) used to manage delayed colonic transit and is resistant to achlorhydric states.

In preferred embodiments of the present invention, the substantially non-releasable form of the opioid antagonist is vulnerable to mechanical, thermal and/or chemical tampering, e.g., tampering by means of crushing, shearing, grinding, chewing and/or dissolution in a solvent in combination with heating (e.g., greater than about 45° C.) of the oral dosage form. When tampered with, the integrity of the substantially non-releasable form of the opioid antagonist is compromised, and the opioid antagonist will be made available for immediate release, and thereby at least partially and preferably substantially blocking the effect of the opioid agonist. Thus, when the oral dosage form comprising the opioid agonist and opioid antagonist is chewed, crushed, ground or dissolved and heated in a solvent, and administered orally, intranasally, parenterally and/or sublingually, the analgesic and/or euphoric effect of the opioid is reduced or eliminated.

The present invention is further directed to a method of decreasing the potential for abuse of an opioid agonist in an oral dosage form. The method comprises providing the opioid agonist in an oral dosage form as described herein.

The term "analgesic effectiveness" is defined for purposes of the present invention as a satisfactory reduction in or elimination of pain, along with a tolerable level of side effects, as determined by the human patient.

The phrase "not substantially blocking the analgesic effect of an opioid agonist" for purposes of the present invention means that the opioid antagonist does not block the effects of the opioid agonist in sufficient degree as to render the dosage form therapeutically less effective for providing analgesia.

The term "tampering" means any manipulation by mechanical, thermal and/or chemical means that changes the physical properties of an intact dosage form in order to liberate at least a portion of the opioid agonist for more rapid or immediate release, or to make the opioid agonist available for inappropriate administration (e.g., parenteral administration). Tampering with the intact dosage form can be, e.g., by means of crushing, shearing, grinding, chewing, dissolution in a solvent, heating (e.g., greater than about 45° C.), or any combination thereof that achieves this purpose.

In certain embodiments, the tampering of the dosage form can be crushing to a powder with a mortar and pestle. In other embodiments the tampering can be by a screw cap pill crusher or by using two stainless steel tablespoons.

In certain embodiments utilizing a mortar and pestle, the crushing can be performed to simulate chewing. For example, three strokes of the pestle can simulate mild chewing, six strokes of the pestle can simulate moderate chewing, and twelve strokes of the pestle can simulate thorough chewing. In certain embodiments, the mortar and pestle can be utilized to crush the dosage form to a powder, with, e.g., 24, 50, 500 or 600 strokes of the pestle.

In certain embodiments utilizing a screw cap pill crusher, the dosage form is placed in the crusher and the screw cap is rotated to crush the dosage form. The cap is then loosened, the crusher is tapped on a hard surface and the crushing is repeated two more times.

In certain embodiments utilizing stainless steel tablespoons, the dosage form is placed on one spoon, a second spoon is placed over the first spoon and the dosage form is crushed between the spoons using hand pressure.

The term "the layer is substantially devoid of antagonist" means that the layer does not contain opioid antagonist except for possibly small amounts which may migrate from the extruded component.

The term "at least partially blocking the opioid effect," is defined for purposes of the present invention to mean that the opioid antagonist at least significantly blocks the euphoric effect of the opioid agonist.

The term "controlled release" as it applies to the opioid agonist is defined for purposes of the present invention as the release of the drug from the formulation at a rate which will provide a longer duration of action than a single dose of the normal (i.e., immediate release) formulation. For example, a typical immediate release oral formulation may release the drug, e.g., over a 1 hour interval, as compared to a controlled release oral formulation which may release the drug, e.g., over a 4 to 24 hour interval.

For purposes of the present invention, the term "opioid agonist" is interchangeable with the term "opioid" or "opioid analgesic" and includes one agonist or combinations of more than one opioid agonist, and also include the use of the base of the opioid, mixed agonist-antagonists, partial agonists, pharmaceutically acceptable salts thereof, stereoisomers thereof, ethers thereof, esters thereof, and mixtures of any of the foregoing.

For purposes of the present invention, the term "opioid antagonist" shall include one antagonist and combinations of more than one antagonist, and also include the use of the base, pharmaceutically acceptable salts thereof, stereoisomers thereof, ethers thereof, esters thereof, and mixtures of any of the foregoing.

The invention disclosed herein is meant to encompass the use of all pharmaceutically acceptable salts thereof of the disclosed opioid agonists and antagonists. The pharmaceutically acceptable salts include, but are not limited to, metal salts such as sodium salt, potassium salt, secium salt and the like; alkaline earth metals such as calcium salt, magnesium salt and the like; organic amine salts such as triethylamine salt, pyridine salt, picoline salt, ethanolamine salt, triethanolamine salt, dicyclohexylamine salt, N,N'-dibenzylethylenediamine salt and the like; inorganic acid salts such as hydrochloride, hydrobromide, sulfate, phosphate and the like; organic acid salts such as formate, acetate, trifluoroacetate, maleate, tartrate and the like; sulfonates such as methanesulfonate, benzenesulfonate, p-toluenesulfonate, and the like; amino acid salts such as arginate, asparginate, glutamate and the like.

Some of the opioid agonists and antagonists used according to the present invention may contain one or more asymmetric centers and may give rise to enantiomers, diastereomers, or other stereoisomeric forms. The present invention is also meant to encompass the use of all such possible forms as well as their racemic and resolved forms and mixtures thereof. When the compounds described herein contain olefinic double bonds or other centers of geometric asymmetry, it is intended to include both E and Z geometric isomers. All tautomers are intended to be encompassed by the present invention as well.

The term "layer" means a material disposed about a particle (which can include itself and one or more optional intermediate layers such e.g., a seal coat) which can be applied, e.g., as a coating. Layering of substrates can be performed by procedures known in the art, e.g., spray coating, dipping or enrobing.

The term "disposed about" means that the material disposed about the particle covers at least a portion of the particle, with or without an intermediate layer or layers between the substance and the particle. In certain embodiments, the material completely covers the particle.

As used herein, the term "stereoisomers" is a general term for all isomers of individual molecules that differ only in the orientation of their atoms is space. It includes enantiomers and isomers of compounds with more than one chiral center that are not mirror images of one another (diastereomers).

The term "chiral center" refers to a carbon atom to which four different groups are attached.

The term "enantiomer" or "enantiomeric" refers to a molecule that is nonsuperimposable on its mirror image and hence optically active wherein the enantiomer rotates the plane of polarized light in one direction and its mirror image rotates the plane of polarized light in the opposite direction.

The term "racemic" refers to a mixture of equal parts of enantiomers and which is optically inactive.

The term "resolution" refers to the separation or concentration or depletion of one of the two enantiomeric forms of a molecule.

The term "X % of the weight of the particles" or "X % weight gain" with respect to the hydrophobic material disposed about the particles of the present invention, means that the hydrophobic material is measured as a % weight of the particle, rather than a % weight of the total layered particle. For example, 100 mg of unlayered particles, subsequently layered to a 10% weight gain, will have 10 mg of hydrophobic material in the layer.

The term "diameter" means the cross-sectional diameter of the particles, which is largely dependent on the diameter of the orifice used in the extrusion process.

The term "length" means the length of the extruded particles, which is largely dependent on the cutting interval of the extruded strand.

The term "pharmaceutical product" means a dosage form suitable for administration or a component of a dosage form.

DETAILED DESCRIPTION

Figure 1:
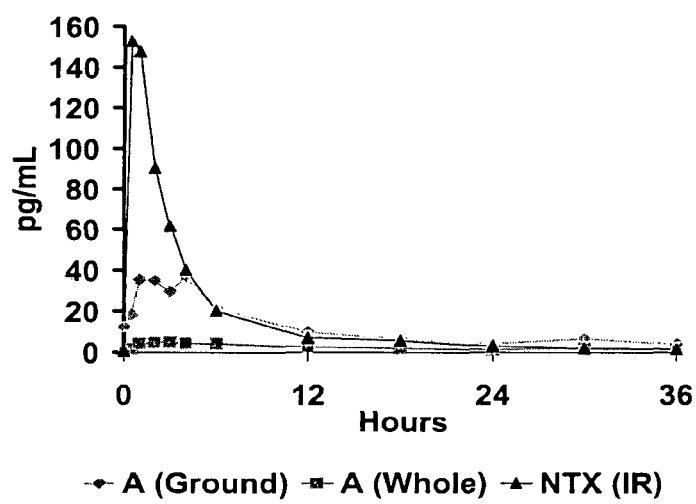
FIG. 1 is a graphical representation of the plasma concentration v. time for the intact naltrexone HCl MEMs (whole), the crushed naltrexone HCl MEMs (ground) and the immediate release naltrexone HCl tablet (IR NTX) dosage form of Example 1.

The present invention is based on the observation that sequestered opioid antagonist particles can be improved by coating extruded opioid antagonist particles with a coating which further reduces the "leak" of the antagonist from the intact form upon exposure to an environmental fluid. By virtue of the present invention, when the sequestered antagonist is combined with an opioid agonist, preferably only a negligible amount of antagonist (i.e., an amount which does not affect the analgesia provided by the agonist) is released under the prescribed conditions of use. Most preferably no amount or no measurable amount of antagonist is released under the prescribed conditions of use.

In certain embodiments, the present invention includes an oral dosage form comprising a plurality of particles comprising an orally therapeutically effective amount of an opioid agonist in combination with a plurality of extruded, sequestered particles comprising an opioid antagonist in an amount to at least substantially block the effects of the opioid agonist if the dosage form is tampered with. Preferably, the plurality of pharmaceutically acceptable particles comprising the opioid antagonist and the plurality of pharmaceutically acceptable particles comprising the opioid agonist are visually similar, and most preferably they are visually indistinguishable.

In certain embodiments, the ratio of the opioid agonist to the opioid antagonist is such that when the oral dosage form is tampered with to compromise the integrity of the particles comprising the opioid antagonist, an amount of the antagonist would be released that would substantially reduce or eliminate the euphoric effect of the opioid agonist when administered to a human subject orally, parenterally, intranasally and/or sublingually.

For example, in certain preferred embodiments of the invention, the euphoric effect of the opioid agonist would be substantially reduced or eliminated by the opioid antagonist when the dosage form is misused parenterally and/or sublingually. In certain embodiments, when the dosage form is chewed, crushed, or dissolved and heated in a solvent, and administered orally, intranasally, parenterally and/or sublingually, the analgesic or euphoric effect of the opioid is substantially reduced or eliminated due to the release of the opioid antagonist. In certain embodiments, the effect of the opioid drug is at least partially blocked by the opioid antagonist. In certain other embodiments, the effect of the opioid drug is substantially blocked by the opioid antagonist. In certain other embodiments, the effect of the opioid drug is completely blocked by the opioid antagonist.

Since the intact oral dosage form of the present invention, when administered properly as intended, does not substantially release the opioid antagonist, the amount of the antagonist may be varied more widely than if the opioid antagonist is available to be released into the GI system upon oral administration.

The opioid antagonist in a sequestered form comprises a plurality of extruded particles comprising an opioid antagonist dispersed in a matrix, with a layer disposed about each of the particles, wherein the matrix and the layer render the antagonist substantially non-releasable. In one embodiment, the layer comprises a pharmaceutically acceptable hydrophobic material. In another embodiment the matrix comprises a pharmaceutical acceptable hydrophobic material. In another embodiment, both the matrix and the layer comprise a pharmaceutical acceptable hydrophobic material. The hydrophobic material of the matrix may be the same as, or different from, the hydrophobic material of the layer. The hydrophobic material is preferably in an amount such that the antagonist is not released or substantially not released from the coated matrix, and thus is unavailable or not substantially available to be absorbed during transit of the oral dosage form through the GI system.

In certain preferred embodiments of the present invention, the opioid antagonist is dispersed in a matrix by melt-extrusion, wherein the matrix comprises one or more pharmaceutically acceptable hydrophobic materials.

In certain embodiments of the invention, the opioid agonist containing particles are controlled release extruded matrix multiparticulates. It has been found in certain embodiments that when controlled release extruded matrix multiparticulates are tampered with in an attempt to make the opioid agonist available for immediate release, only a portion of the agonist is liberated for immediate release. In certain embodiments, the weight percent of agonist released from the extruded dosage form after tampering based on dissolution at 1 hour of the dosage form in 700 ml of SGF using a USP Type II (paddle) apparatus at 50 rpm at 37 degrees C. is less than 50%; less than 40%; or less than 35%.

Since only a portion of the opioid antagonist can be liberated for immediate release from matrix multiparticulates upon tampering, the antagonist can be included in a higher load in order to ensure that an amount necessary for the intended purpose of the invention is liberated upon tampering. For example, if an embodiment of the invention liberates 50% of the antagonist upon tampering, the dosage form can be formulated with a 4 mg load of antagonist if a 2 mg antagonist release is required to be liberated upon tampering. As the oral dosage forms of the present invention provide no release or substantially no-release of the antagonist upon administration of an intact dosage form, the high load of antagonist will not result in a release from the intact dosage form of an amount of antagonist that would interfere with the analgesic efficacy of the agonist.

Materials for use in the extruded matrices of the present invention include, for example and without limitation, hydrophilic and/or hydrophobic materials, such as gums, cellulose ethers, acrylic resins, protein derived materials; digestible, long chain ($C_8$-$C_{50}$, especially $C_{12}$-$C_{40}$), substituted or unsubstituted hydrocarbons, such as fatty acids, fatty alcohols, glyceryl esters of fatty acids, mineral and vegetable oils and waxes (natural and synthetic), and stearyl alcohol; and polyalkylene glycols. The matrices can contain between 1% and 80% (by weight) of at least one hydrophilic or preferably at least one hydrophobic material.

When the extruded matrix comprises a hydrophobic material, the hydrophobic material is any hydrophobic material useful for this purpose, but is preferably selected from the group consisting of alkylcelluloses, acrylic and methacrylic acid polymers and copolymers, shellac, zein, hydrogenated castor oil, hydrogenated vegetable oil, or mixtures thereof. In certain preferred embodiments of the present invention, the hydrophobic material is a pharmaceutically acceptable acrylic polymer, including but not limited to any of acrylic acid and methacrylic acid copolymers, methyl methacrylate, methyl methacrylate copolymers, ethoxyethyl methacrylates, cyanoethyl methacrylate, aminoalkyl methacrylate copolymer, poly(acrylic acid), poly(methacrylic acid), methacrylic acid alkylamine copolymer, poly(methyl methacrylate), poly(methacrylic acid)(anhydride), polymethacrylate, polyacrylamide, poly(methacrylic acid anhydride), and glycidyl methacrylate copolymers.

Acrylic polymers useful in the present invention include, but are not limited to, acrylic resins comprising copolymers synthesized from acrylic and methacrylic acid esters (e.g., the copolymer of acrylic acid lower alkyl ester and methacrylic acid lower alkyl ester) containing about 0.02 to 0.03 mole of a tri (lower alkyl) ammonium group per mole of the acrylic and methacrylic monomers used. An example of a suitable acrylic resin is a polymer manufactured by Rohm Pharma GmbH and sold under the Eudragit® RS trademark. Eudragit® RS30D is preferred. Eudragit® RS is a water insoluble copolymer of ethyl acrylate (EA), methyl methacrylate (MM) and trimethylammoniumethyl methacrylate chloride (TAM) in which the molar ratio of TAM to the remaining components (EA and MM) is 1:40. Acrylic resins such as Eudragit® RS may be used in the form of an aqueous suspension.

In other embodiments, the hydrophobic material is selected from materials such as one or more hydroxyalkylcelluloses such as hydroxypropylmethylcellulose.

In certain embodiments, the hydrophobic materials useful in the invention have a melting point from about 30° to about 200° C., or from about 45° to about 90° C.

In certain embodiments, the hydrophobic material comprises natural or synthetic waxes, fatty alcohols (such as lauryl, myristyl, stearyl, cetyl or cetostearyl alcohol), fatty acids, including but not limited to fatty acid esters, fatty acid glycerides (mono-, di-, and tri-glycerides), hydrogenated fats, hydrocarbons, normal waxes, stearic aid, stearyl alcohol and hydrophobic and hydrophilic materials having hydrocarbon backbones. Suitable waxes include, for example, beeswax, glycowax, castor wax and carnauba wax. For purposes of the present invention, a wax-like substance is defined as any material which is normally solid at room temperature and has a melting point of from about 30° to about 100° C.

In certain embodiments, the hydrophobic material comprises a cellulose polymer selected from the group consisting of ethylcellulose, cellulose acetate, cellulose propionate (lower, medium or higher molecular weight), cellulose acetate propionate, cellulose acetate butyrate, cellulose acetate phthalate and cellulose triacetate. An example of ethylcellulose is one that has an ethoxy content of 44 to 55%. Ethylcellulose may be used in the form of an alcoholic solution. In certain other embodiments, the hydrophobic material comprises polylactic acid, polyglycolic acid or a co-polymer of polylactic and polyglycolic acid.

In certain embodiments, the hydrophobic material comprises a cellulose polymer selected from the group consisting of cellulose ether, cellulose ester, cellulose ester ether, and cellulose. In certain embodiments, the cellulosic polymers have a degree of substitution, D.S., on the anhydroglucose unit, from greater than zero and up to 3 inclusive. By degree of substitution is meant the average number of hydroxyl groups present on the anhydroglucose unit comprising the cellulose polymer that are replaced by a substituting group. Representative materials include a polymer selected from the group consisting of cellulose acylate, cellulose diacylate, cellulose triacylate, cellulose acetate, cellulose diacetate, cellulose triacetate, mono, di, and tricellulose alkanylates, mono, di, and tricellulose aroylates, and mono, di, and tricellulose alkenylates. Exemplary polymers include cellulose acetate having a D.S. up to 1 and an acetyl content up to 21%; cellulose acetate having an acetyl content up to 32 to 39.8%; cellulose acetate having a D.S. of 1 to 2 and an acetyl content of 21 to 35%; and cellulose acetate having a D.S. of 2 to 3 and an acetyl content of 35 to 44.8%.

Specific cellulosic polymers include cellulose propionate having a D.S. of 1.8, a propyl content of 39.2 to 45% and a hydroxyl content of 2.8 to 5.4%; cellulose acetate butyrate having a D.S. of 1.8, an acetyl content of 13 to 15% and a butyryl content of 34 to 39%; cellulose acetate butyrate having an acetyl content of 2 to 29%, a butyryl content of 17 to 53% and a hydroxyl content of 0.5 to 4.7%; cellulose triacylate having a D.S. of 2.9 to 3 such as cellulose triacetate, cellulose trivalerate, cellulose trilaurate, cellulose tripalmitate, cellulose trisuccinate, and cellulose trioctanoate; cellulose diacylates having a D.S. of 2.2 to 2.6 such as cellulose disuccinate, cellulose dipalmitate, cellulose dioctanoate, cellulose dipentanoate, and coesters of cellulose such as cellulose acetate butyrate, cellulose acetate octanoate butyrate and cellulose acetate propionate.

Additional cellulose polymers include acetaldehyde dimethyl cellulose acetate, cellulose acetate ethylcarbamate, cellulose acetate methylcarbamate, and cellulose acetate dimethylaminocellulose acetate.

In certain embodiments, the pharmaceutically acceptable hydrophobic material includes a biodegradable polymer comprising a copolymer of lactic and glycolic acid ("PLGA"), polylactide, polyglycolide, polyanhydride, polyorthoester, polycaprolactone, polyphosphazene, polysaccharide, proteinaceous polymer, polyester, polydioxanone, polygluconate, polylactic-acid-polyethylene oxide copolymers, poly(hydroxybutyrate), polyphosphoesther or a mixture or blend of any of the foregoing.

In certain embodiments, the biodegradable polymer comprises a PLGA, having molecular weight of about 2,000 to about 500,000 daltons. The ratio of lactic acid to glycolic acid is from about 100:0 to about 25:75, with the ratio of lactic acid to glycolic acid of about 65:35 being preferred.

PLGA may be prepared by the procedure set forth in U.S. Pat. No. 4,293,539 (Ludwig et al.), the disclosure of which is hereby incorporated by reference in its entirety. In brief, Ludwig prepares the copolymer by condensation of lactic acid and glycolic acid in the presence of a readily removable polymerization catalyst (e.g., a strong acid ion-exchange resin such as Dowex HCR-W2-H). The amount of catalyst is not critical to the polymerization, but typically is from about 0.01 to about 20 parts by weight relative to the total weight of combined lactic acid and glycolic acid. The polymerization reaction may be conducted without solvents at a temperature from about 100° C. to about 250° C. for about 48 to about 96 hours, preferably under a reduced pressure to facilitate removal of water and by-products. PLGA is then recovered by filtering the molten reaction mixture in an organic solvent such as dichloromethane or acetone and then filtering to remove the catalyst.

In certain preferred embodiments, a combination of two or more hydrophobic materials are included in the extruded matrix. If two or more hydrophobic materials are included, at least one hydrophobic material is preferably selected from natural and synthetic waxes, fatty acids, fatty alcohols, and mixtures of the same. Examples include, but are not limited to, beeswax, carnauba wax, stearic acid and stearyl alcohol.

When the hydrophobic material is a hydrocarbon, the hydrocarbon preferably has a melting point of between 25° and 90° C. Of the long chain hydrocarbon materials, fatty (aliphatic) alcohols are preferred. The matrix may contain up to 60% (by weight) of at least one digestible, long chain hydrocarbon.

In certain preferred embodiments, the extruded matrix contains up to 60% (by weight) of at least one polyalkylene glycol.

One suitable extruded matrix comprises at least one water soluble hydroxyalkyl cellulose, at least one $C_{12}$-$C_{36}$, preferably $C_{14}$-$C_{22}$, aliphatic alcohol and, optionally, at least one polyalkylene glycol. The hydroxyalkyl cellulose is preferably a hydroxy ($C_1$ to $C_6$) alkyl cellulose, such as hydroxypropylcellulose, hydroxypropylmethylcellulose or hydroxyethylcellulose. The amount of the hydroxyalkyl cellulose in the oral dosage form will be determined, inter alia, by the precise rate of release of the active agent required. The aliphatic alcohol may be, for example, lauryl alcohol, myristyl alcohol or stearyl alcohol. In particularly preferred embodiments, however, the aliphatic alcohol is cetyl alcohol or cetostearyl alcohol. The amount of the aliphatic alcohol in the oral dosage form will be determined, inter alia, by the precise rate of release of the active agent required. It will also vary depending on whether a polyalkylene glycol is present in the oral dosage form. In the absence of polyalkylene glycol, the oral dosage form will preferably contain between about 20% and about 50% (by wt) of the aliphatic alcohol. When at least one polyalkylene glycol is present in the oral dosage form, the combined weight of the aliphatic alcohol and the polyalkylene glycol preferably constitutes between 20% and 50% (by wt) of the total dosage form.

In one embodiment, the ratio of the hydroxyalkyl cellulose or acrylic resin to the aliphatic alcohol/polyalkylene glycol determines, to a considerable extent, the release rate of the active agent from the formulation. A ratio of the hydroxyalkyl cellulose to the aliphatic alcohol/polyalkylene glycol of between 1:2 and 1:4 is preferred, with a ratio of between 1:3 and 1:4 being particularly preferred.

The polyalkylene glycol may be, for example, polypropylene glycol or polyethylene glycol. The average molecular weight of the polyalkylene glycol is preferably between about 1,000 and about 15,000, and particularly between about 1,500 and about 12,000.

Another suitable extruded matrix comprises an alkylcellulose (especially ethyl cellulose), a $C_{12}$ to $C_{36}$ aliphatic alcohol and, optionally, a polyalkylene glycol.

Another suitable extruded matrix comprises an acrylic polymer (especially Eudragit® RSPO), a $C_{12}$ to $C_{36}$ aliphatic alcohol and, optionally, a polyalkylene glycol.

In certain preferred embodiments, the matrix includes a combination of at least two pharmaceutically acceptable hydrophobic materials.

As disclosed above, the plurality of extruded particles comprising the pharmaceutically acceptable matrix comprising the opioid antagonist are layered with one or more hydrophobic materials which, in addition to the matrix material, can provide for the sequestration of the opioid antagonist. The hydrophobic material of the coating may be selected from any of those mentioned above. In certain preferred embodiments, the hydrophobic material is a cellulosic material or polymer, an acrylic polymer, or combination thereof. The terms "first hydrophobic material", "second hydrophobic material" and "third hydrophobic material" are each meant to encompass one ore more hydrophobic materials in at least a partial dispersion or in laminar arraignment. The first, second and third hydrophobic materials can be the same or different. In certain embodiments, the first and second hydrophobic materials can be the same; the first and third hydrophobic materials can be the same; the second and third hydrophobic materials can be the same; or the first, second and third hydrophobic materials can be the same.

In embodiments with more than one hydrophobic material in the layer, the hydrophobic materials can be interdispersed or partially interdispersed. Alternatively, the hydrophobic materials can be in laminar arrangement. For example, a layer in an amount of 25% of the weight of the particles can have a 15% ethylcellulose layer by weight of the particles and a 10% acrylic polymer layer by weight of the particles disposed about the ethylcellulose layer.

The coating composition may be applied by spraying it onto the plurality of extruded particles using any suitable spray equipment known in the art. For example, a Wurster fluidized-bed system may be used in which an air jet, injected from underneath, fluidizes the coated material and effects drying while the coating is sprayed on. The thickness of the coating will depend on the characteristics of the particular coating composition being used.

Hydrophobic materials suited for layering the extruded particles of the present invention include cellulosic materials and polymers, including alkylcelluloses. One preferred alkylcellulosic polymer is ethylcellulose, although other cellulose and/or alkylcellulose polymers may be readily employed, singly or in combination, as all or part of a hydrophobic coating according to the invention.

One commercially-available aqueous dispersion of ethylcellulose is Aquacoat® (FMC Corp., Philadelphia, Pa., U.S.A.), which is prepared by dissolving the ethylcellulose in a water-immiscible organic solvent and then emulsifying the same in water in the presence of a surfactant and a stabilizer. After homogenization to generate submicron droplets, the organic solvent is evaporated under vacuum to form a pseudolatex.

Another aqueous dispersion of ethylcellulose is commercially available as Surelease® (Colorcon, Inc., West Point, Pa., U.S.A.). This product is prepared by incorporating plasticizer into the dispersion during the manufacturing process. A hot melt of a polymer, plasticizer (dibutyl sebacate), and stabilizer (oleic acid) is prepared as a homogeneous mixture, which is then diluted with an alkaline solution to obtain an aqueous dispersion that can be applied directly onto the plurality of particles.

In other preferred embodiments of the present invention, the hydrophobic material of the layer is a pharmaceutically acceptable acrylic polymer, including but not limited to acrylic acid and methacrylic acid copolymers, methyl methacrylate copolymers, ethoxyethyl methacrylates, cyanoethyl methacrylate, poly(acrylic acid), poly(methacrylic acid), methacrylic acid alkylamide copolymer, poly(methyl methacrylate), polymethacrylate, poly(methyl methacrylate) copolymer, polyacrylamide, aminoalkyl methacrylate copolymer, poly(methacrylic acid anhydride), glycidyl methacrylate copolymers, and combinations thereof.

In certain preferred embodiments, the acrylic polymer is comprised of one or more ammonio methacrylate copolymers. Ammonio methacrylate copolymers are well known in the art, and are described in NF XVII as fully polymerized copolymers of acrylic and methacrylic acid esters with a low content of quaternary ammonium groups.

In certain preferred embodiments, it may be necessary to incorporate two or more ammonio methacrylate copolymers having differing physical properties, such as different molar ratios of the quaternary ammonium groups to the neutral (meth)acrylic esters.

In certain embodiments, the acrylic layer comprises a mixture of two acrylic resin lacquers commercially available from Rohm Pharma (Darmstadt, Germany) under the Tradenames Eudragit® RL30D and Eudragit® RS30D, respectively. Eudragit® RL30D and Eudragit® RS30D are copolymers of acrylic and methacrylic esters with a low content of quaternary ammonium groups, the molar ratio of ammonium groups to the remaining neutral (meth)acrylic esters being 1:20 in Eudragit® RL30D and 1:40 in Eudragit® RS30D. The mean molecular weight is about 150,000. The code designations RL (high permeability) and RS (low permeability) refer to the permeability properties of these agents. In certain embodiments, the Eudragit® RS in the present invention is selected from the group consisting of Eudragit® RSPM, Eudragit® RSPO, Eudragit® RS100, Eudragit® RS12.5, and mixtures thereof. The wording "Eudragit® RSPM" represents general unground powders of Eudragit® RS, the wording "Eudragit® RSPO" represents groundfine powders of Eudragit® RS, and the wording "Eudragit® RS 100" represents granules of Eudragit® RS, while the wording "Eudragit® RS12.5" represents Eudragit® RS solution products in which Eudragit® RS is dissolved in an organic solvent. In certain embodiments, the Eudragit® RL for use in the present invention is selected from the group consisting of Eudragit® RLPM, Eudragit® RLPO, Eudragit® RL100, Eudragit® RL12.5, and mixtures thereof. The wordings "PM," "PO," "100," and "12.5" are defined as above with respect to Eudragit® RS. The mixture of the Eudragit® RS series and the Eudragit® RL series at any ratio is also used as the ammonio methacrylate copolymer of the present invention.

The Eudragit® RL/RS dispersions of the present invention may be mixed together in any desired ratio in order to ultimately obtain a sequestered formulation having a desirable dissolution profile. For example, desirable formulations may be obtained, for instance, from a coating derived from 100% Eudragit® RL, 50% Eudragit® RL and 50% Eudragit® RS, and 10% Eudragit® RL:Eudragit® 90% RS. Of course, one skilled in the art will recognize that other acrylic polymers may also be used, such as, for example, Eudragit® L.

The layer may be applied in the form of an organic or aqueous solution or dispersion. The layer may be applied to obtain a weight gain from about 2 to about 25% of the plurality of pharmaceutically acceptable particles comprising the opioid antagonist in order to obtain a desired sequestration. Coatings derived from aqueous dispersions are described, in detail e.g., in U.S. Pat. Nos. 5,273,760 and 5,286,493. Other examples of coatings which may be used in accordance with the present invention include U.S. Pat. Nos. 5,324,351; 5,356,467, and 5,472,712.

In certain embodiments, wherein the plurality of extruded particles comprising the opioid antagonist are layered with an aqueous dispersion of a hydrophobic material, the aqueous dispersion of hydrophobic material preferably includes an effective amount of plasticizer.

In embodiments of the present invention where the layer is prepared from an aqueous dispersion of a hydrophobic material, the inclusion of an effective amount of a plasticizer in the aqueous dispersion will further improve the physical properties of the layer. For example, as ethylcellulose has a relatively high glass transition temperature and does not form flexible films under normal coating conditions, it is preferable to incorporate a plasticizer into an ethylcellulose coating solution. Generally, the amount of plasticizer included in a solution is based on the concentration of the film-former, e.g., most often from about 1 to about 50 percent by weight of the film-former.

Examples of suitable plasticizers for ethylcellulose include water insoluble plasticizers such as dibutyl sebacate, diethyl phthalate, triethyl citrate, tributyl citrate, and triacetin, although other water-insoluble plasticizers (such as acetylated monoglycerides, phthalate esters, castor oil, etc.) may be used. Triethyl citrate is an especially preferred plasticizer for aqueous dispersions of ethyl cellulose.

Examples of potentially suitable plasticizers for the acrylic polymers of the present invention include, but are not limited to, citric acid esters such as triethyl citrate NF XVI, tributyl citrate, dibutyl phthalate, and propylene glycol. Other plasticizers which have proved to be suitable for enhancing the elasticity of the films formed from acrylic films such as Eudragit® RL/RS lacquer solutions include polyethylene glycols, diethyl phthalate, castor oil, and triacetin. Triethyl citrate is an especially preferred plasticizer for aqueous dispersions of acrylic polymers.

Plasticized hydrophobic material may be applied onto the plurality of pharmaceutically acceptable particles comprising the opioid antagonist by spraying, using any suitable spray equipment known in the art. In a preferred method, a Wurster fluidized-bed system is used in which an air jet, injected from underneath, fluidizes the core material and effects drying while the coating is sprayed on.

The coating solutions of the present invention may further comprise in addition to the hydrophobic material, plasticizer, and solvent system (e.g., water), a colorant to provide elegance and product distinction. Suitable coloring agents include alcohol or propylene glycol based color dispersions, milled aluminum lakes and opacifiers such as titanium dioxide and iron oxide pigments. The coloring agents can be added to a dispersion of hydrophobic material during the coating process. Alternatively, any other suitable method of providing color to the formulations of the present invention may be used. For example, a color coat such as Opadry® may be applied to the pharmaceutically acceptable coated particles.

In certain embodiments, a small amount of talc may be used in order to reduce the tendency of the aqueous dispersion to stick during processing, and/or to act as a polishing agent.

The plurality of pharmaceutically acceptable particles can comprise the opioid agonist dispersed in a controlled release matrix that slowly releases the opioid agonist in a controlled manner over a period of time, e.g., when ingested and exposed to gastric fluid, and then to intestinal fluid. The matrix of the particles preferably provides for the controlled release of agonist over a period of from about 8 to about 24 hours, preferably from about 12 to about 24 hours. The controlled release matrix for use in the particles comprising the opioid agonist may include those materials describe above with respect to the hydrophilic and/or hydrophobic materials (such as, gums, cellulose ethers, acrylic resins, protein derived materials; digestible, long chain ($C_8$-$C_{50}$, especially $C_{12}$-$C_{40}$), substituted or unsubstituted hydrocarbons, such as fatty acids, fatty alcohols, glyceryl esters of fatty acids, mineral and vegetable oils and waxes (natural and synthetic), and stearyl alcohol; and polyalkylene glycols).

In certain embodiments, the particles comprising the opioid agonist may comprise an immediate release matrix with a controlled release layer disposed on it's surface. The controlled release layer may include one or more of the hydrophobic materials described above.

In certain embodiments, the plurality of pharmaceutically acceptable particles comprising the opioid agonist are optionally layered with one or more materials suitable for: (i) the regulation of the opioid agonist release; (ii) for the protection of the formulation or (iii) to provide a coating virtually indistinguishable from that of the coated particles comprising the antagonist; or a combination of (i), (ii) or (iii). For example, in one embodiment, a coating is provided to permit either pH-dependent or pH-independent release, e.g., when exposed to GI fluid. A pH-dependent coating serves to release the opioid in desired areas of the GI tract, e.g., the stomach or small intestine, such that an absorption profile is provided which is capable of providing at least about eight hours and preferably about twelve hours to up to about twenty-four hours of analgesia to a patient. When a pH-independent layer is desired, the layer is designed to achieve release of the opioid regardless of pH changes in the environmental fluid, e.g., the GI tract. It is also possible to formulate compositions which release a portion of the dose in one desired area of the GI tract, e.g., the stomach, and release the remainder of the dose in another area of the GI tract, e.g., the small intestine.

In certain embodiments, the plurality of pharmaceutically acceptable particles containing the opioid agonist or opioid antagonist are cured. Preferably the particles are cured until an endpoint is reached at which the plurality of pharmaceutically acceptable particles provide a stable dissolution (or no dissolution). The curing endpoint may be determined by comparing the dissolution profile (curve) of the dosage form immediately after curing to the dissolution profile (curve) of the dosage form after exposure to accelerated storage conditions of, e.g., at least one month at a temperature of 40° C. and a relative humidity of 75%. Cured formulations are described in detail, e.g., in U.S. Pat. Nos. 5,273,760; 5,286,493; 5,500,227; 5,580,578; 5,639,476; 5,681,585; and 6,024,982. Other examples of controlled-release formulations and coatings which may be used in accordance with the present invention include those described in U.S. Pat. Nos. 5,324,351; 5,356,467; and 5,472,712.

In certain embodiments, the plurality of pharmaceutically acceptable particles comprising the opioid agonist and/or the pharmaceutically acceptable particles comprising the opioid antagonist are film coated with a material that does not substantially affect the release of the opioid agonist and/or opioid antagonist from the pharmaceutically acceptable particles. In certain embodiments, a film coat, such as Opadry®, is applied to the plurality of pharmaceutically acceptable particles. The film coat is provided, if at all, preferably in order to substantially reduce agglomeration of the particles or to help make the agonist and antagonist containing particles difficult to distinguish from each other. Preferably, the film coating of the present invention should be capable of producing a strong, continuous film that is smooth and elegant, capable of supporting pigments and other coating additives, non-toxic, inert, and tack-free.

In addition to the above ingredients, either or both of the particles comprising the opioid agonist and the particles comprising the antagonist may also contain suitable quantities of other materials, e.g., diluents, lubricants, binders, granulating aids, spheronizing agents, colorants, flavorants and glidants that are conventional in the pharmaceutical art. The quantities of these additional materials will be sufficient to provide the desired effect to the desired formulation.

Examples of lubricants include but are not limited to magnesium stearate, sodium stearate, stearic acid, calcium stearate, magnesium oleate, oleic acid, potassium oleate, caprylic acid, sodium stearyl fumarate, and magnesium palmitate.

Suitable binders, such as low viscosity, water soluble polymers, will be well known to those skilled in the pharmaceutical art. However, water soluble hydroxy lower alkyl cellulose, such as hydroxy propyl cellulose, is preferred.

Colorants may include titanium dioxide and/or dyes suitable for food such as those known as F. D. & C dyes, and natural coloring agents such as grape skin extract, beet red powder, beta carotene, annato, carmine, turmeric, paprika, and combinations of any of the foregoing.

Flavors incorporated in the composition may be chosen from synthetic flavor oils and flavoring aromatics and/or natural oils, extracts from plants leaves, flowers, fruits, and combinations of any of the foregoing.

Specific examples of pharmaceutically acceptable carriers, diluents, granulating aids, glidants and other excipients that may be used to formulate oral dosage forms are described in the *Handbook of Pharmaceutical Excipients*, American Pharmaceutical Association (1986).

A number of processes may be used to prepare the dosage forms of the present invention so long as the techniques used do not damage the integrity of the sequestered antagonist (e.g., when combining the antagonist particles with the agonist particles). Damaging the integrity of the sequestered antagonist particles may result in an amount of opioid antagonist being released upon administration of an intact dosage form which compromises the efficacy of the agonist.

A preferred process for preparing particles of the present invention is via melt-extrusion or melt-granulation techniques. Generally, melt-granulation techniques involve melting or softening a normally solid hydrophobic material, e.g., a wax, and incorporating a powdered drug therein. In certain embodiments, additional hydrophobic substance, e.g., ethylcellulose or a water-insoluble acrylic polymer, may be added into the melted or softened hydrophobic material.

The additional hydrophobic material may comprise one or more wax-like thermoplastic substances. In certain embodiments, the individual wax-like substances in the formulation should be substantially non-degradable and insoluble in GI fluids during the initial release phases. Useful wax-like substances may be those with a water-solubility that is lower than about 1:5,000 (w/w).

In certain embodiments, the preparation of a suitable melt-extruded matrix according to the present invention can include the steps of blending the opioid agonist or opioid antagonist, together with at least one or more hydrophobic materials to obtain a homogeneous mixture. The homogeneous mixture is then heated to a temperature sufficient to at least soften the mixture sufficiently to extrude the same. The resulting homogeneous mixture is then extruded, e.g., to form elongated strands. The extrudate is preferably cooled and cut into multiparticulates (e.g., a plurality of particles) by any means known in the art. The extrudate preferably has a mean diameter of from about 0.1 to about 12 mm, about 0.1 to about 2.5 mm, about 0.2 to about 6 mm, 0.5 to about 3 mm, about 0.5 mm to about 2 mm, or about 1 mm to about 2 mm.

Suitable hydrophobic materials useful in preparing the melt-extruded matrix include, but are not limited to, acrylic polymers, cellulosic polymers and aliphatic alcohols as described above.

An optional process for preparing the melt extrusions of the present invention involves directly metering into an extruder a hydrophobic material, a therapeutically active agent, and an optional binder; blending and heating the ingredients to form a homogenous mixture; extruding the homogenous mixture to thereby form elongated strands; cooling the strands containing the homogeneous mixture; cutting the strands into particles having a size from about 0.1 mm to about 12 mm. In this aspect of the invention, a relatively continuous manufacturing procedure is realized.

The diameter of the extruder aperture or exit port can be adjusted to vary the thickness of the extruded strands. Furthermore, the exit port of the extruder need not be round; it can be oblong, rectangular, etc. The exiting strands can be reduced to particles using a hot wire cutter, guillotine, etc.

The melt extruded matrices can be, for example, in the form of granules, spheroids or pellets depending upon the extruder exit port. For purposes of the present invention, the terms "melt-extruded matrices," and "melt-extruded matrix system(s)," "melt-extruded multiparticulates" and "melt-extruded particles" all refer to a plurality of units, preferably of similar size and/or shape and containing one or more active agents and one or more excipients, preferably including a hydrophobic material as described herein. In this regard, the melt-extruded matrices will be in a size range of from about 0.1 to about 12 mm; from about 0.1 to about 2.5 mm; from about 0.2 to about 6 mm; from about 0.5 to about 3 mm; from about 0.5 mm to about 2 mm; or from about 1 mm to about 2 mm in diameter and/or length. In addition, it is to be understood that the melt-extruded matrices can be any geometrical shape within this size range. In certain embodiments, the extrudate may be cut into desired lengths and divided into unit doses of the opioid antagonist or opioid agonist without the need of a spheronization step.

In other embodiments of the invention, the melt extruded material is prepared without the inclusion of the opioid agonist and/or opioid antagonist, which are added thereafter to the extrudate. Such formulations typically will have the drugs blended together with the extruded matrix material, and then the mixture would be formed into multiparticulates by means known in the art. Such formulations may be advantageous, for example, when the opioid agonist or opioid antagonist included in the formulation is sensitive to temperatures needed for softening the one or more hydrophobic materials.

In certain embodiments a process for manufacturing the plurality of pharmaceutically acceptable particles is the extrusion/spheronization process. For this process, the opioid agonist or opioid antagonist is wet-massed with a binder, extruded through a perforated plate or die, and placed on a rotating disk. The extrudate preferably breaks into pieces which are rounded into spheres, spheroids, or rounded rods on the rotating plate. A preferred process and composition for this method involves using water to wet-mass a blend comprising, e.g., about 20% to 75% of a cellulose derivative blended with, e.g., about 80% to 25% of the opioid agonist or opioid antagonist.

In certain embodiments, a process for manufacturing a plurality of pharmaceutically acceptable particles involves using an organic solvent to aid mixing of the opioid antagonist or agonist with the matrix material. This technique can be used when it is desired to utilize a matrix material with an otherwise unsuitably high melting point that, if the material were employed in a molten state, would cause decomposition of the drug or of the matrix material, or would result in an unacceptable melt viscosity, thereby preventing mixing of the drug (e.g., opioid agonist or opioid antagonist) with the matrix material. The drug and matrix material may be combined with a modest amount of solvent to form a paste, and then forced through a screen to form granules from which the solvent is then removed. Alternatively, the drug and matrix material may be combined with enough solvent to completely dissolve the matrix material, and the resulting solution (which may contain solid drug particles) spray dried to form the plurality of pharmaceutically acceptable particles. This technique is preferred when the matrix material is a high molecular weight synthetic polymer such as a cellulose ether or cellulose ester. Solvents typically employed for the process include acetone, ethanol, isopropanol, ethyl acetate, and mixtures thereof.

As stated above, the plurality of extruded particles that comprise the opioid antagonist have a layer, which preferably comprises a hydrophobic material, disposed about each of the particles. Preferably, the layered particles comprising the opioid antagonist significantly reduce or prevent the release of the opioid antagonist, while the pharmaceutically acceptable particles comprising the opioid agonist preferably provide controlled release of the opioid agonist for a time period of from about 8 to about 24 hours or more, most preferably for a time period of from about 12 to about 24 hours.

In preferred embodiments, the layer disposed about the antagonist-containing matrix is impermeable or substantially impermeable to the antagonist and is insoluble or substantially insoluble in the GI system. Preferably, when the intact dosage form of the present invention is orally administered to humans, the opioid antagonist is not substantially released and is, therefore, not available for absorption into the body. Thus, the opioid antagonist, although present in the dosage form, does not substantially block the analgesic effectiveness of the opioid agonist. However, if the oral dosage form of the present invention is tampered with, the opioid antagonist contained therein would be released to at least partially block the effect of the opioid agonist. This aspect of the invention may decrease the potential for abuse or diversion of the opioid agonist in the oral dosage form. For example, if a person attempts to abuse the drug contained in the oral dosage form of the present invention by, e.g., chewing, crushing, grinding or dissolving it in a solvent with heat (e.g., greater than about 45° C. to about 50° C.), both the layer and matrix will be damaged and will no longer serve to sequester the opioid antagonist. Upon administration of a tampered dosage form, the opioid antagonist will be released and preferably substantially block the euphoric effect of the opioid agonist.

The plurality of pharmaceutically acceptable particles (i.e., the layered opioid antagonist extruded particles and the opioid agonist particles) of the present invention are further incorporated into an oral dosage form, optionally with conventional excipients known in the art.

In one preferred embodiment, oral dosage forms are prepared to include an effective amount of the opioid agonist-containing particles and opioid antagonist-containing particles within a capsule. For example, a plurality of the pharmaceutically acceptable particles may be placed in a gelatin capsule in an amount sufficient to provide an effective sustained release dose when ingested. The capsule may be sealed, or may be unsealed to allow a sprinkling of the particles.

In another embodiment, a suitable amount of the layered antagonist-containing particles are combined with the opioid agonist-containing particles and compressed into an oral tablet, without substantially disrupting the integrity of the plurality of pharmaceutically acceptable particles.

In another embodiment, a suitable amount of the layered antagonist-containing particles are combined with an opioid formulation (e.g., a sustained release granulation) and compressed into a tablet, wherein the antagonist-containing particles are embedded in an agonist matrix, without disrupting the integrity of the plurality of pharmaceutically acceptable particles.

Techniques and compositions for making tablets (compressed and molded), capsules (hard and soft gelatin) and pills are also described in *Remington's Pharmaceutical Sciences*, (Arthur Osol, editor), 1553-1593 (1980).

In certain embodiments, the oral dosage forms can also include an amount of an immediate release opioid agonist for prompt therapeutic effect. In certain embodiments, an immediate release opioid agonist may be incorporated, e.g., as separate pellets within a gelatin capsule, or may be coated on the surface of the agonist-containing particles after preparation of the dosage forms.

The controlled release formulations of the present invention preferably slowly release the opioid agonist, e.g., when ingested and exposed in turn to gastric fluids, and then to intestinal fluids. The controlled release profile of the formulations of the invention can be altered, for example, by varying the amount of retardant, i.e., hydrophobic material, by varying the amount of plasticizer relative to hydrophobic material, by the inclusion of additional ingredients or excipients, by altering the method of manufacture, etc.

In preferred embodiments, opioid agonists useful in the present invention include, but are not limited to alfentanil, allylprodine, alphaprodine, anileridine, benzylmorphine, bezitramide, buprenorphine, butorphanol, clonitazene, codeine, desomorphine, dextromoramide, dezocine, diampromide, diamorphone, dihydrocodeine, dihydromorphine, dimenoxadol, dimepheptanol, dimethylthiambutene, dioxaphetyl butyrate, dipipanone, eptazocine, ethoheptazine, ethylmethylthiambutene, ethylmorphine, etonitazene, etorphine, dihydroetorphine, fentanyl and derivatives, heroin, hydrocodone, hydromorphone, hydroxypethidine, isomethadone, ketobemidone, levorphanol, levophenacylmorphan, lofentanil, meperidine, meptazinol, metazocine, methadone, metopon, morphine, myrophine, narceine, nicomorphine, norlevorphanol, normethadone, nalorphine, nalbuphene, normorphine, norpipanone, opium, oxycodone, oxymorphone, papaveretum, pentazocine, phenadoxone, phenomorphan, phenazocine, phenoperidine, piminodine, piritramide, propheptazine, promedol, properidine, propoxyphene, sufentanil, tilidine, tramadol, pharmaceutically acceptable salts thereof, and mixtures of any of the foregoing. In certain embodiments, the amount of the opioid agonist in the dosage form may be about 75 ng to 750 mg.

In preferred embodiments, the opioid antagonist of the present invention is selected from naltrexone, naloxone, nalmefene, cyclazacine, levallorphan, pharmaceutically acceptable salts thereof, and mixtures of any of the foregoing. In certain preferred embodiments, the opioid antagonist is naltrexone or a pharmaceutically acceptable salt thereof (e.g., naltrexone HCl). In certain embodiments, the amount of the opioid antagonist, present in a substantially non-releasable form, may be from about 0.5 mg to about 50 mg, from about 1 mg to about 25 mg, from about 2 mg to about 20 mg, from about 5 mg to about 15 mg, from about 2 mg to about 10 mg, or from about 4 mg to about 10 mg or from about 6 mg to about 8 mg.

Naloxone is an opioid antagonist which is almost void of agonist effects. Subcutaneous doses of up to 12 mg of naloxone produce no discernable subjective effects, and 24 mg naloxone causes only slight drowsiness. Small doses (0.4-0.8 mg) of naloxone given intramuscularly or intravenously in man prevent or promptly reverse the effects of morphine-like opioid agonist. One mg of naloxone intravenously has been reported to completely block the effect of 25 mg of heroin. The effects of naloxone are seen almost immediately after intravenous administration. The drug is absorbed after oral administration, but has been reported to be metabolized into an inactive form rapidly in its first passage through the liver such that it has been reported to have significantly lower potency than when parenterally administered. Oral dosage of more than 1 g has been reported to be almost completely metabolized in less than 24 hours. It has also been reported that 25% of naloxone administered sublingually is absorbed. Weinberg, et al., Sublingual Absorption of selected Opioid Analgesics, *Clin Pharmacol Ther*. (1988); 44:335-340.

Other opioid antagonists, for example, cyclazocine and naltrexone, both of which have cyclopropylmethyl substitutions on the nitrogen, retain much of their efficacy by the oral route and their durations of action are much longer, approaching 24 hours after oral doses.

In a preferred embodiment of the invention, the opioid agonist comprises oxycodone, hydrocodone, hydromorphone, morphine, oxymorphone, codeine or a pharmaceutically acceptable salt thereof and the opioid antagonist comprises naltrexone or a pharmaceutically acceptable salt thereof and is present in an amount from about 2 mg to about 15 mg, in an amount from about 5 mg to about 10 mg, or from about 6 mg to about 8 mg.

In embodiments in which the opioid agonist comprises hydrocodone or a pharmaceutically acceptable salt thereof, the sustained release oral dosage forms may include analgesic doses from about 8 mg to about 50 mg of hydrocodone or salt thereof per dosage unit. In sustained release oral dosage forms where hydromorphone or a pharmaceutically acceptable salt thereof is the therapeutically active opioid, it is included in an amount from about 2 mg to about 64 mg hydromorphone or salt thereof. In another embodiment, the opioid agonist comprises morphine or a pharmaceutically acceptable salt thereof, and the controlled release oral dosage form of the present invention includes from about 2.5 mg to about 800 mg morphine or salt thereof. In yet another embodiment, the opioid agonist comprises oxycodone or a pharmaceutically acceptable salt thereof and the controlled release oral dosage form includes from about 2.5 mg to about 800 mg oxycodone or salt thereof. In certain preferred embodiments, the sustained release oral dosage form includes about 5 mg, 10 mg, 20 mg, 40 mg, 60 mg, 80 mg, 160 mg or 320 mg oxycodone hydrochloride. Controlled release oxycodone formulations are known in the art. In certain embodiments, the opioid agonist comprises tramadol or a pharmaceutically acceptable salt thereof and the controlled release oral dosage forms may include from about 25 mg to 800 mg tramadol per dosage unit. The dosage form may contain more than one opioid agonist to provide an equivalent therapeutic effect as compared to a therapeutic effect achieved by a single agonist product. Alternatively, the dosage form may contain molar equivalent amounts of other salts of the opioid agonists useful in the present invention.

In certain embodiments a stabilizer is included in the dosage form to prevent the degradation of the opioid antagonist. In certain embodiments, stabilizers of use in the dosage form include for example and without limitation, organic acids, carboxylic acids, acid salts of amino acids (e.g., cysteine, L-cysteine, cysteine hydrochloride, glycine hydrochloride or cystine dihydrochloride), sodium metabisulphite, ascorbic acid and its derivatives, malic acid, isoascorbic acid, citric acid, tartaric acid, palmitic acid, sodium carbonate, sodium hydrogen carbonate, calcium carbonate, calcium hydrogen phosphate, sulphur dioxide, sodium sulphite, sodium bisulphate, tocopherol, as well as its water- and fat-soluble derivatives, such as e.g., tocofersolan or tocopherol acetate, sulphites, bisulphites and hydrogen sulphites or alkali metal, alkaline earth metal and other metals, PHB esters, gallates, butylated hydroxyanisol (BHA) or butylated hydroxytoluene (BHT), and 2,6-di-t-butyl-.alpha.-dimethyl-amino-p-cresol, t-butylhydroquinone, di-t-amylhydroquinone, di-t-butylhydroquinone, butylhydroxytoluene, butylhydroxyanisole, pyrocatechol, pyrogallol, propyl/gallate, and nordihydroguaiaretic acid, as well as lower fatty acids, fruit acids, phosphoric acids, sorbic and benzoic acids as well as their salts, esters, derivatives and isomeric compounds, ascorbyl palmitate, lecithins, mono- and polyhydroxylated benzene derivatives, ethylenediamine-tetraacetic acid and its salts, citraconic acid, conidendrine, diethyl carbonate, methylenedioxyphenols, kephalines, β,β'-dithiopropionic acid, biphenyl and other phenyl derivatives, pharmaceutically acceptable salts thereof, and mixtures thereof.

The oral dosage form of the present invention may further include, in addition to an opioid agonist and antagonist, one or more drugs that may or may not act synergistically therewith. Thus, in certain embodiments, a combination of two opioid agonists may be included in the dosage form, in addition to the opioid antagonist. For example, the dosage form may include two opioid agonists having different properties, such as half-life, solubility, potency, and a combination of any of the foregoing. In yet further embodiments, one or more opioid agonist is included and a further non-opioid drug is also included, in addition to the opioid antagonist. Such non-opioid drugs would preferably provide additional analgesia, and include, for example, aspirin, acetaminophen; non-steroidal anti-inflammatory drugs ("NSAID"), e.g., ibuprofen, ketoprofen, etc.; N-methyl-D-aspartate (NMDA) receptor antagonists, e.g., a morphinan such as dextromethorphan or dextrorphan, or ketamine; cycooxygenase-II inhibitors ("COX-II inhibitors"); and/or glycine receptor antagonists. The additional agent may be included in the same particles as the first agonist, or in different particles.

In certain preferred embodiments of the present invention, the invention allows for the use of lower doses of the opioid analgesic by virtue of the inclusion of an additional non-opioid agonist, such as an NSAID or a COX-2 inhibitor. By using lower amounts of either or both drugs, the side effects associated with effective pain management in humans may be reduced.

Suitable non-steroidal anti-inflammatory agents, include ibuprofen, diclofenac, naproxen, benoxaprofen, flurbiprofen, fenoprofen, flubufen, ketoprofen, indoprofen, piroprofen, carprofen, oxaprozin, pramoprofen, muroprofen, trioxaprofen, suprofen, aminoprofen, tiaprofenic acid, fluprofen, bucloxic acid, indomethacin, sulindac, tolmetin, zomepirac, tiopinac, zidometacin, acemetacin, fentiazac, clidanac, oxpinac, mefenamic acid, meclofenamic acid, flufenamic acid, niflumic acid, tolfenamic acid, diflurisal, flufenisal, piroxicam, sudoxicam or isoxicam, pharmaceutically acceptable salts thereof, mixtures thereof, and the like. Useful dosages of these drugs are well known to those skilled in the art.

N-methyl-D-aspartate (NMDA) receptor antagonists are well known in the art, and encompass, for example, morphinans such as dextromethorphan or dextrorphan, ketamine, d-methadone or pharmaceutically acceptable salts thereof. For purposes of the present invention, the term "NMDA antagonist" is also deemed to encompass drugs that block a major intracellular consequence of NMDA-receptor activation, e.g. a ganglioside such as $GM_1$ or $GT_{1b}$, a phenothiazine such as trifluoperazine or a naphthalenesulfonamide such as N-(6-aminothexyl)-5-chloro-1-naphthalenesulfonamide. These drugs are purported to inhibit the development of tolerance to and/or dependence on addictive drugs, e.g., narcotic analgesics such as morphine, codeine, etc. in U.S. Pat. Nos. 5,321,012 and 5,556,838 (both to Mayer, et al.), and to treat chronic pain in U.S. Pat. No. 5,502,058 (Mayer, et al).

The treatment of chronic pain via the use of glycine receptor antagonists and the identification of such drugs is described in U.S. Pat. No. 5,514,680 (Weber, et al.).

COX-2 inhibitors have been reported in the art and many chemical structures are known to produce inhibition of cyclooxygenase-2. COX-2 inhibitors are described, for example, in U.S. Pat. Nos. 5,616,601; 5,604,260; 5,593,994; 5,550,142; 5,536,752; 5,521,213; 5,475,995; 5,639,780; 5,604,253; 5,552,422; 5,510,368; 5,436,265; 5,409,944; and 5,130,311. Certain preferred COX-2 inhibitors include celecoxib (SC-58635), DUP-697, flosulide (CGP-28238), meloxicam, 6-methoxy-2 naphthylacetic acid (6-MNA), MK-966 (also known as Vioxx), nabumetone (prodrug for 6-MNA), nimesulide, NS-398, SC-5766, SC-58215, T-614; pharmaceutically acceptable salts thereof, and combinations thereof. Dosage levels of COX-2 inhibitor on the order of from about 0.005 mg to about 140 mg per kilogram of body weight per day are therapeutically effective in combination with an opioid analgesic. Alternatively, about 0.25 mg to about 7 g per patient per day of a COX-2 inhibitor is administered in combination with an opioid analgesic. Combinations of opioid agonists and COX-2 inhibitors is disclosed in WO 99/13799.

In yet further embodiments, a non-opioid drug can be included which provides a desired effect other than analgesia, e.g., antitussive, expectorant, anti-emetic, decongestant, antihistamine drugs, local anesthetics, and the like.

The present invention is also directed to the dosage forms disclosed herein utilizing different active agent/antagonist combinations (i.e. non-opioid) in order to deter the abuse of the active agent. For example, when a benzodiazepine is used as the active agent in the dosage form of the present invention, a sequestered benzodiazepine antagonist can be formulated in the dosage form. When a barbiturate is used as an active agent in the dosage form of the present invention, a sequestered barbiturate antagonist can be formulated in the dosage form. When an amphetamine is used as an active agent in the dosage form of the present invention, a sequestered amphetamine antagonist can be formulated in the dosage form.

The term "benzodiazepines" refers to benzodiazepines and drugs that are derivatives of benzodiazepine that are able to depress the central nervous system. Benzodiazepines include, but are not limited to, alprazolam, bromazepam, chlordiazepoxied, clorazepate, diazepam, estazolam, flurazepam, halazepam, ketazolam, lorazepam, nitrazepam, oxazepam, prazepam, quazepam, temazepam, triazolam, methylphenidate and mixtures thereof.

Benzodiazepine antagonists that can be used in the present invention include, but are not limited to, flumazenil.

Barbiturates refer to sedative-hypnotic drugs derived from barbituric acid (2,4,6,-trioxohexahydropyrimidine). Barbiturates include, but are not limited to, amobarbital, aprobarbotal, butabarbital, butalbital, methohexital, mephobarbital, metharbital, pentobarbital, phenobarbital, secobarbital and mixtures thereof.

Barbiturate antagonists that can be used in the present invention include, but are not limited to, amphetamines, as described herein.

Stimulants refer to drugs that stimulate the central nervous system. Stimulants include, but are not limited to, amphetamines, such as amphetamine, dextroamphetamine resin complex, dextroamphetamine, methamphetamine, methylphenidate and mixtures thereof.

Stimulant antagonists that can be used in the present invention include, but are not limited to, benzodiazepines, as described herein.

The present invention is also directed to the dosage forms disclosed herein utilizing adverse agents other than antagonists in order to deter the abuse of the active agent. The term "adverse agent" refers to any agent which can creates an unpleasant effect administered in a non-sequestered form. Examples of adverse agents, other than antagonists, include emetics, irritants and bittering agents.

Emetics include, but are not limited to, ipecac and apomorphine.

Irritants include, but are not limited to, capsaicin, capsaicin analogs, and mixtures thereof. Capsaicin analogs include resiniferatoxin, tinyatoxin, heptanoylisobutylamide, heptanoyl guaiacylamide, other isobutylamides or guaiacylamides, dihydrocapsaicin, homovanillyl octylester, nonanoyl vanillylamide, and mixtures thereof.

Bittering agents include, but are not limited to, flavor oils; flavoring aromatics; oleoresins; extracts derived from plants, leaves, flowers; fruit flavors; sucrose derivatives; chlorosucrose derivatives; quinine sulphate; denatonium benzoate; and combinations thereof The present invention will now be more fully described with reference to the accompanying examples. It should be understood, however, that the following description is illustrative only and should not be taken in any way as a restriction of the invention.

Example 1

Naltrexone HCl 2 mg Capsules

This is a comparator example of the opioid antagonist naltrexone HCl which has been formulated as melt extruded multiparticulates (hereinafter "MEMs") to produce a sequestered product. Based on the polymers and excipients selected, the MEM pellets release very little naltrexone when the pellets are analyzed intact, but release a significant amount of naltrexone when tampered (crushed). This example is included as a reference to show how the coatings in the examples that follow example 1, can enhance these sequestered properties. The naltrexone HCl formulation of Example 1 is listed in the table below.

TABLE 1A

Formula

| Ingredient | Amt/unit (mg) | Amt/batch (kg) |
|---|---|---|
| Naltrexone HCl | 2.0 | 0.10 |
| Eudragit RSPO | 88.0 | 4.40 |
| Stearyl Alcohol | 15.0 | 0.75 |
| Stearic Acid | 15.0 | 0.75 |
| Butylated Hydroxytoluene (BHT) | 1.0 | 0.05 |
| Size # 2 Hard Gelatin Capsules | 61.0 | 3.05 |
| Total | 182.0 | 9.10 |

The naltrexone HCl formulation of Example 1 was prepared using the following process:

Process

1. Milling: Pass the stearyl alcohol flakes through an oscillating mill equipped with a 16 mesh screen to achieve a powder that is easily blendable.
2. Blending: Mix Naltrexone HCl, Eudragit RSPO, milled Stearyl Alcohol, Stearic Acid and BHT in a twin shell blender.
3. Extruding: Continuously feed the blended material from Step 2 into a twin screw extruder and collect extruded (Leistritz ZSE-27) at a rate ranging from 1.7 kg/hr to 2.6 kg/hr. Extrude the blend at a barrel temperature range of 75° C. and 100° C. into strands approximately 1 mm in diameter. Collect the extruded strands on a conveyor.
4. Cooling: Allow the strands to cool on the conveyor.
5. Pelletizing: Cut the cooled strands into pellets approximately 1 mm in length using a Pelletizer.
6. Screening: Screen the pellets through a vibratory separator using a 16 TBC mesh and a 26 TBC mesh screen. Collect the material retained on the 26 TBC mesh screen as desired product.
7. Encapsulating: Fill the screened pellets into hard gelatin capsules at a target weight of 121 mg.

In Vitro Dissolution

Formulations prepared in accordance with Example 1 gave the following results listed in Table 1B when subject to the following in vitro dissolution testing method.

Method:
1. Apparatus-USP Type II (Paddle), 75 rpm at 37° C.
2. Sampling Time: 1, 2, 4, 8, 12, 24, 36 hours
3. Media: 700 ml of SGF (simulated gastric fluid) for one hour with a switch to 900 ml of SIF (simulated intestinal fluid) thereafter
4. Analytical Method: High Performance Liquid Chromatography Results:

TABLE 1B

| | Time (hours) | | | | | | |
|---|---|---|---|---|---|---|---|
| | 1 | 2 | 4 | 8 | 12 | 24 | 36 |
| Mean % Dissolved | 1.3 | 2.6 | 2.9 | 3.6 | 4.0 | 5.2 | 6.2 |

Simulated Tampering Process and Dissolution

Formulations prepared in accordance with Example 1 were subject to a simulated tampering process and then subject to the following in-vitro dissolution testing method. The dissolution results for 1 hour are listed in Table 1C. In the tampering process, naltrexone pellets were ground with a mortar and pestle (600 strokes) to a powder for this dissolution study.

Dissolution Method: Same as above

Results:

TABLE 1C

| | Time (hour) 1 |
|---|---|
| Mean % Dissolved | 33.5 |

Crush:Intact Ratio

The crush-to-intact ratio is the ratio of the % dissolution of the crushed pellets at 1 hour to the % dissolution of the intact pellets at 36 hours.

Crush-to-intact ratio results: 33.5%/6.2%=5.4:1

In Vivo Human Pharmacokinetic/Bioavailability-Study

Capsules (MEMs) manufactured using the above process and formula were used in a clinical study to determine the pharmacokinetics/bioavailability compared to Immediate-Release Naltrexone tablets. Human subjects were administered either the intact naltrexone HCl MEMs (whole), the crushed naltrexone HCl MEMs (ground) or an immediate release naltrexone HCl tablet (IR NTX) dosage form. The results are demonstrated in the graphical representation in FIG. 1. The dose adjusted (to the 1 mg IR NTX tablet) extent of exposure (AUCt) of the intact (whole) and crushed (ground) compared to the immediate-release naltrexone (IR NTX) and the dose adjusted Cmax of the IR NTX, crushed (ground) and intact (whole) are listed in Table 1D below.

TABLE 1D

| Formulation | Parameter | IR NTX | Crushed MEMs (Ground) | Intact (Whole) MEMs |
|---|---|---|---|---|
| A | Mean AUCt (pg/mL · h) | 564.4 | 373.4 | 84.7 |
| | Mean Cmax (pg/mL) | 142.1 | 43.1 | 5.3 |

Dose-adjusted plasma concentrations show that there is a minimal release of naltrexone from the MEMs dosage form when taken intact. The naltrexone level is increased when the MEMs are taken crushed (ground). Based on the mean Cmax, crushed MEMs/intact MEMs capsule ration is about 8. Similarly, the mean AUCt, crushed MEMs/intact MEMs capsule ratio is about 4.4. This indicates that the total and peak exposure ratios are significantly increased following crushing.

Example 2

Ethylcellulose Coated Naltrexone HCl 2 mg Pellets

In Example 2, naltrexone MEMs were prepared similar to Example 1 and then the MEMs were coated with ethylcellulose (Surelease) to various levels (5%, 10%, 15%, and 20% weight gains). The uncoated naltrexone HCl formulation of Example 2 is listed in Table 2A below:

TABLE 2A

Pellet Formula

| Ingredient | Amt/unit (mg) | Amt/batch (kg) |
|---|---|---|
| Naltrexone HCl | 2.0 | 0.10 |
| Eudragit RSPO | 88.0 | 4.40 |
| Stearyl Alcohol | 15.0 | 0.75 |
| Stearic Acid | 15.0 | 0.75 |
| Butylated Hydroxytoluene (BHT) | 1.0 | 0.05 |
| Total | 121.0 | 6.05 |

The uncoated naltrexone HCl formulation of Example 2 was prepared using the following process:

Process

1. Milling: Pass the stearyl alcohol flakes through an oscillating mill equipped with a 16 mesh screen to achieve a powder that is easily blendable.
2. Blending: Mix Naltrexone HCl, Eudragit RSPO, milled Stearyl Alcohol, Stearic Acid and BHT in a twin shell blender.
3. Extruding: Continuously feed the blended material from Step 2 into a twin screw extruder (Leistritz ZSE-27) at a rate ranging from 2.9 kg/hr to 4.8 kg/hr. Extrude the blend at a barrel temperature range of 95° C. and 105° C. into strands approximately 1 mm in diameter. Collect the extruded strands on a conveyor.
4. Cooling: Allow the strands to cool on the conveyor.
5. Pelletizing: Cut the cooled strands into pellets approximately 1 mm in length using a Pelletizer.
6. Screening: Screen the pellets through a vibratory separator using a 16 TBC mesh and a 26 TBC mesh screen. Collected the material retained on the 26 TBC mesh screen as desired product.

In Vitro Dissolution

Uncoated formulations prepared in accordance with Example 2 gave the following results listed in Table 2B when subject to the following in vitro dissolution testing method.

Method:
1. Apparatus-USP Type II (Paddle), 50 rpm at 37° C.
2. Sampling Time: 1, 2, 4, 8, 12, 18, 24, 36 hours
3. Media: 700 ml of SGF for one hour with a switch to 900 ml of SIF thereafter
4. Analytical Method: High Performance Liquid Chromatography Results:

TABLE 2B

| | Time (hours) | | | | | | | |
|---|---|---|---|---|---|---|---|---|
| | 1 | 2 | 4 | 8 | 12 | 18 | 24 | 36 |
| Mean % Dissolved | 2.1 | 2.6 | 2.9 | 3.2 | 3.8 | 4.2 | 4.7 | 5.3 |

Simulated Tampering Process and Dissolution

Formulations prepared in accordance with Example 2 were subject to a simulated tampering process and then subject to the following dissolution testing method. The dissolution results for 45 minutes are listed in Table 2C. In the tampering process, the uncoated Naltrexone Pellets were ground with a mortar and pestle (24 strokes) to a powder for this dissolution study.

Dissolution Method:
1. Apparatus-USP Type II (Paddle), 50 rpm at 37° C.
2. Sampling Time: 45 minutes
3. Media: 700 ml of SGF
4. Analytical Method: High Performance Liquid Chromatography Results:

TABLE 2C

| | Time (minute) 45 |
|---|---|
| Mean % Dissolved | 31 |

Crush:Intact Ratio

The crush-to-intact ratio is the ratio of the % dissolution of the crushed pellets at 45 minutes to the % dissolution of the intact pellets at 36 hours.

Crush-to-intact ratio results: 31%/5.3%=5.8:1

Naltrexone HCl pellets prepared in accordance with Example 2 and listed in Table 2A were further coated with a hydrophobic coating. The pellets were coated to weight gains of 5%, 10%, 15% and 20% with a hydrophobic coating (Surelease); and 20% with a hydrophobic coating (Surelease) and a color coating (Opadry). An example of the formulation having a 20% weight gain coating and color coating is listed in the following table.

TABLE 2D

20% weight gain with color coating

| Ingredient | Amt/unit (mg) | Amt/batch (kg) |
|---|---|---|
| Naltrexone HCl 2 mg Pellets | 121.0 | 0.50 |
| Surelease (solids) | 24.2 | 0.10 |
| Opadry Pink | 6.05 | 0.025 |
| Total | 151.25 | 0.625 |

The coated naltrexone HCl formulations of Example 2 were prepared using the following process:

Process
1. Functional Coating Dispersion: Dilute Surelease suspension to a 15% w/w solids by mixing with water.
2. Color Coating Dispersion: Mix Opadry with water to get a 10% w/w dispersion.
3. Functional Coating: Spray the Surelease dispersion onto the naltrexone pellets prepared above at 700 g scale using a fluid bed processor (GPCG-1) using the following parameter guidelines:
   Air Speed: 7.0 to 9.0 m/s
   Inlet Air Temperature: 40-50° C.
   Dispersion Spray Rate: 8-11 g/min
   Samples were taken when the theoretical amount of dispersion was sprayed for 5%, 10%, 15% and 20% weight gain.
4. Color Coating: Upon completion of the functional coating, spray Opadry dispersion onto the coated pellets using the following parameter guidelines:

Air Speed: 7.0 m/s
Inlet Air Temperature: 50° C.
Dispersion Spray Rate: 8.5 g/min
5. Screening: Screen the pellets through a 14 US mesh screen and a 20 US mesh screen. Collect the material retained on the 20 US mesh screen as desired product.
6. Curing: Place the screened pellets and samples in an oven at 45° C. for 24 hours.

The pellets coated to a 5%, 10% and 15% weight gain were prepared in accordance with the above 20% formula and procedure using 6.05, 12.1 and 18.15 mg of Surelease per unit, respectively.

In Vitro Dissolution

The coated formulations prepared in accordance with Example 2 gave the following results listed in Table 2E when subject to the following in vitro dissolution testing method.

Method:
1. Apparatus-USP Type II (Paddle), 50 rpm at 37° C.
2. Sampling Time: 1, 2, 4, 8, 12, 18, 24, 36 hours
3. Media: 700 ml of SGF for one hour with a switch to 900 ml of SIF thereafter
4. Analytical Method: High Performance Liquid Chromatography Results:

TABLE 2E

| | | Time (hours) | | | | | | | |
|---|---|---|---|---|---|---|---|---|---|
| | | 1 | 2 | 4 | 8 | 12 | 18 | 24 | 36 |
| Mean % Dissolved | Uncoated | 2.1 | 2.6 | 2.9 | 3.2 | 3.8 | 4.2 | 4.7 | 5.3 |
| | 5% | 0.0 | 0.6 | 0.9 | 1.4 | 1.8 | 2.2 | 2.4 | 3.2 |
| | 10% | 0.0 | 0.7 | 0.6 | 1.0 | 1.2 | 1.6 | 1.8 | 2.3 |
| | 15% | 0.0 | 0.0 | 0.5 | 0.8 | 1.1 | 1.4 | 1.6 | 2.1 |
| | 20% | 0.0 | 0.0 | 0.0 | 0.7 | 0.9 | 1.3 | 1.5 | 2.0 |
| | 20% w/Opadry | 0.0 | 0.0 | 0.7 | 1.0 | 1.2 | 1.5 | 1.6 | 2.0 |

As can be see from the dissolution results, the dissolution of the naltrexone pellets generally decreased with increased polymer coating levels.

Simulated Tampering Process and Dissolution

The formulations prepared in accordance with Example 2 were subject to a simulated tampering process and then subject to the following dissolution testing method. The dissolution results for 45 minutes are listed in Table 2F. In the tampering process the uncoated and coated naltrexone pellets were each separately ground with a mortar and pestle (24 strokes) to a powder for this dissolution study.

Dissolution Method:
1. Apparatus-USP Type II (Paddle), 50 rpm at 37° C.
2. Sampling Time: 45 minutes
3. Media: 700 ml of SGF
4. Analytical Method: High Performance Liquid Chromatography

TABLE 2F

| | | Time (minute) |
|---|---|---|
| | | 45 |
| Mean % Dissolved | Uncoated | 31 |
| | 5% | 19 |
| | 10% | 21 |
| | 15% | 21 |
| | 20% | 21 |
| | 20% w/Opadry | 20 |

Results:

Crush:Intact Ratio

The crush-to-intact ratio is the ratio of the % dissolution of the crushed pellets at 45 minutes to the % dissolution of the intact pellets at 36 hours. The results are listed in Table 2G below.

Crushed-to-Intact Ratio Results:

TABLE 2G

| Crush:Intact Ratio | |
|---|---|
| Uncoated | 5.8 |
| 5% | 5.9 |
| 10% | 9.1 |
| 15% | 10.0 |
| 20% | 10.5 |
| 20% w/Opadry | 10.0 |

As can be see from the dissolution results, as the coating level increases, the Crush:Intact Ratio increases.

Results of Example 2, Compared to Example 1

Thus, by overcoating the MEMs in Example 2 which is the same formulation of the uncoated MEMs of Example 1, release of drug at 36 hours dropped from over 5% to approximately 2%. As a consequence, the "leak" of antagonist from the uncoated MEMs of Example 1 is also reduced significantly by using a functional coat. The crush to intact ratio can increase from approximately 5:1 to 10:1.

Example 3

Ethylcellulose Coated Naltrexone HCl 8 mg Pellets

In Example 3, pellets containing 8 mg of naltrexone were prepared and then coated with ethylcellulose (Surelease) to various levels (5%, 10%, 15%, and 20%, 25% and 30% weight gains). The uncoated naltrexone HCl formulation of Example 3 is listed in the table below.

TABLE 3A

| Pellet Formula | | |
|---|---|---|
| Ingredient | Amt/unit (mg) | Amt/batch (kg) |
| Naltrexone HCl | 8.0 | 0.397 |
| Eudragit RSPO | 84.0 | 4.165 |
| Stearyl Alcohol | 14.0 | 0.694 |
| Stearic Acid | 14.0 | 0.694 |
| Butylated Hydroxytoluene (BHT) | 1.0 | 0.05 |
| Total | 121.0 | 6.00 |

Uncoated naltrexone HCl formulations of Example 3 was prepared using the following process:

Process

1. Milling: Pass the stearyl alcohol flakes through an oscillating mill equipped with a 16 mesh screen to achieve a powder that is easily blendable.
2. Blending: Mix Naltrexone HCl, Eudragit RSPO, milled Stearyl Alcohol, Stearic Acid and BHT in a twin shell blender.
3. Extruding: Continuously feed the blended material from Step 2 into a twin screw extruder (Leitritz ZSE-27) at a rate of 3.9 kg/hr. Extrude the blend at a barrel temperature range of 95° C. and 100° C. into strands approximately 1 mm in diameter. Collect the extruded strands on a conveyor.
4. Cooling: Allow the strands to cool on the conveyor.
5. Pelletizing: Cut the cooled strands into pellets approximately 1 mm in length using a Pelletizer.
6. Screening: Screen the pellets through a vibratory separator using a 16 TBC mesh and a 26 TBC mesh screen. Collect the material retained on the 26 TBC mesh screens as desired product.

In Vitro Dissolution

The uncoated formulation prepared in accordance with Example 3 gave the following results listed in Table 3B when subject to the following in vitro dissolution testing method.

Method:
1. Apparatus-USP Type II (Paddle), 50 rpm at 37° C.
2. Sampling Time: 1, 6, 12, 24, 36 hours
3. Media: 700 ml of SGF for one hour with a switch to 900 ml of SIF thereafter
4. Analytical Method: High Performance Liquid Chromatography Results:

TABLE 3B

| | Time (hours) | | | | |
|---|---|---|---|---|---|
| | 1 | 6 | 12 | 24 | 36 |
| Mean % Dissolved | 4.2 | 8.6 | 11.4 | 15.5 | 18.7 |

Simulated Tampering Process and Dissolution

The formulations prepared in accordance with Example 3 were subject to a simulated tampering process and then subject to the following dissolution testing method. The results for 45 minutes are listed in Table 3C. In the tampering process, the uncoated naltrexone pellets were ground with a mortar and pestle (24 strokes) to a powder for this dissolution study.

Dissolution Method:
1. Apparatus-USP Type II (Paddle), 50 rpm at 37° C.
2. Sampling Time: 45 minutes
3. Media: 700 ml of SGF
4. Analytical Method: High Performance Liquid Chromatography Results:

TABLE 3C

| | Time (minute) |
|---|---|
| | 45 |
| Mean % Dissolved | 57 |

Crush:Intact Ratio

The crush-to-intact ratio is the ratio of the % dissolution of the crushed pellets at 45 minutes to the % dissolution of the intact pellets at 36 hours.
Crush-to-intact ratio results: 57%/18.7%=3.0

The naltrexone HCl pellets prepared in accordance with Example 3 and listed in Table 3A were further coated with a hydrophobic coating. The pellets were coated to weight gains of 5%, 10%, 15%, 20% and 25% with a hydrophobic coating (Surelease); and 30% with a hydrophobic coating (Surelease) and a color coating (Opadry). An example of the formulation having a 30% weight gain hydrophobic coating and a color coating is listed in the following table.

TABLE 3D

| Coated Pellet Formula for 30% Weight Gain | | |
|---|---|---|
| Ingredient | Amt/unit (mg) | Amt/batch (kg) |
| Naltrexone HCl 8 mg Pellets | 121.0 | 0.50 |
| Surelease (solids) | 36.3 | 0.15 |
| Opadry Pink | 6.1 | 0.025 |
| Total | 163.4 | 0.675 |

The coated naltrexone HCl formulations of Example 3 were prepared using the following process:

Process

1. Functional Coating Dispersion: Dilute Surelease suspension to 15% w/w solids by mixing with water.
2. Color Coating Dispersion: Mix Opadry with water to get a 10% w/w dispersion.
3. Functional Coating: Spray the Surelease dispersion onto the Naltrexone pellets prepared above at 700 g scale using a fluid bed processor (GPCG-1) with the following parameter guidelines:
   Air Speed: 8.6 to 9.6 m/s
   Inlet Air Temperature: 40-50° C.
   Dispersion Spray Rate: 9-14.8 g/min
   Samples were taken at when the theoretical amount of dispersion was sprayed for 5%, 10%, 15%, 20%, 25%, 30% weight gain (approximately 6.05, 12.1, 18.15, 24.2 and 30.25 mg Surelease per unit, respectively.
4. Color Coating: Upon completion of the functional coating, spray Opadry dispersion onto the coated pellets using the following parameter guidelines:
   Air Speed: 8.6-9.0 m/s
   Inlet Air Temperature: 47° C.
   Dispersion Spray Rate: 9.0 g/min
5. Screening: Screen the pellets through a 14 US mesh screen and a 20 US mesh screen. Collect the material retained on the 20 US mesh screen as desired product.
6. Curing: Place the screened pellets and samples in an oven at 45° C. for 24 hours.

In Vitro Dissolution

The formulations coated with hydrophobic coating (Surelease) and color coating (Opadry) prepared in accordance with Example 3 gave the following results listed in Table 3E when subject to the following in vitro dissolution testing method.

Method:
1. Apparatus-USP Type II (Paddle), 50 rpm at 37° C.
2. Sampling Time: 1, 6, 12, 24, 36 hours
3. Media: 700 ml of SGF for one hour with a switch to 900 ml of SIF thereafter
4. Analytical Method: High Performance Liquid Chromatography Results:

TABLE 3E

|  |  | Time (hours) | | | | |
| --- | --- | --- | --- | --- | --- | --- |
|  |  | 1 | 6 | 12 | 24 | 36 |
| Mean % Dissolved | Uncoated | 4.2 | 8.6 | 11.4 | 15.5 | 18.7 |
|  | 5% | 0.3 | 1.9 | 3.1 | 4.7 | 5.9 |
|  | 10% | 0.2 | 0.7 | 1.1 | 1.9 | 2.6 |
|  | 15% | 0.2 | 0.5 | 0.8 | 1.4 | 1.9 |
|  | 20% | 0.2 | 0.4 | 0.6 | 1.1 | 1.5 |
|  | 25% | 0.1 | 0.4 | 0.6 | 1.1 | 1.5 |
|  | 30% w/Opadry | 0.1 | 0.4 | 0.7 | 1.0 | 1.4 |

As can be seen from the dissolution results, the dissolution of the naltrexone pellets generally decreased with increased polymer coating levels.

Simulated Tampering Process and Dissolution

The formulations prepared in accordance with Example 3 were subject to a simulated tampering process and then subject to the following dissolution testing method. The dissolution results for 45 minutes are listed in Table 3F. In the tampering process the uncoated and coated naltrexone pellets were each separately ground with a mortar and pestle (24 strokes) to a powder for this dissolution study.

Dissolution Method:
1. Apparatus-USP Type II (Paddle), 50 rpm at 37° C.
2. Sampling Time: 45 minutes
3. Media: 700 ml of SGF
4. Analytical Method: High Performance Liquid Chromatography Results:

TABLE 3F

|  |  | Time (minute) |
| --- | --- | --- |
|  |  | 45 |
| Mean % Dissolved | Uncoated | 57 |
|  | 5% | 60 |
|  | 10% | 56 |
|  | 15% | 49 |
|  | 20% | 48 |
|  | 25% | 56 |
|  | 30% w/Opadry | 52 |

Crush:Intact Ratio

The crush-to-intact ratio is the ratio of the % dissolution of the crushed pellets at 45 minutes to the % dissolution of the intact pellets at 36 hours. The results are listed in Table 3G below.

Crush-to-intact ratio results:

TABLE 3G

| Crush:Intact Ratio | |
| --- | --- |
| Uncoated | 3.0 |
| 5% | 10.2 |
| 10% | 21.5 |
| 15% | 25.8 |
| 20% | 32.0 |
| 25% | 37.3 |
| 30% w/Opadry | 37.1 |

As can be seen from the dissolution results above, as the coating level increases, the amount of naltrexone released from the intact pellets decreases significantly (from over 18% to less than 2% at 36 hours), yet when crushed, approximately 50% of the antagonist is released, and the Crush:Intact Ratio increases significantly.

After coating, the 8 mg intact pellets demonstrated a significant decrease in the release of naltrexone as compared to the uncoated intact pellets. However, the release from the crushed coated 8 mg pellets is higher compared to the crushed uncoated 2 mg pellets.

Example 4

Methacrylic Copolymer Coated Naltrexone HCl 8 mg Pellets

In Example 4, pellets containing 8 mg of naltrexone were prepared as in Example 3, but coated with a methacrylic copolymer (Eudragit RS 30D) to various levels (5%, 10%, 15%, and 20%, and 25% weight gains). The uncoated naltrexone HCl formulation of Example 4 is listed in Table 4A below:

TABLE 4A

| Pellet Formula | | |
| --- | --- | --- |
| Ingredient | Amt/unit (mg) | Amt/batch (kg) |
| Naltrexone HCl | 8.0 | 0.397 |
| Eudragit RSPO | 84.0 | 4.165 |
| Stearyl Alcohol | 14.0 | 0.694 |
| Stearic Acid | 14.0 | 0.694 |
| Butylated Hydroxytoluene (BHT) | 1.0 | 0.05 |
| Total | 121.0 | 6.00 |

The uncoated naltrexone HCl formulation of Example 4 was prepared using the following process:

Process

1. Milling: Pass the stearyl alcohol flakes through an oscillating mill equipped with a 16 mesh screen to achieve a powder that is easily blendable.
2. Blending: Mix Naltrexone HCl, Eudragit RSPO, milled Stearyl Alcohol, Stearic Acid and BHT in a twin shell blender.
3. Extruding: Continuously feed the blended material from Step 2 into a twin screw extruder (Leistritz ZSE-27) at a rate of 3.9 kg/hr. Extrude the blend at a barrel temperature range of 95° C. and 100° C. into strands approximately 1 mm in diameter. Collect the extruded strands on a conveyor.
4. Cooling: Allow the strands to cool on the conveyor.
5. Pelletizing: Cut the cooled strands into pellets approximately 1 mm in length using a Pelletizer.

6. Screening: Screen the pellets through a vibratory separator using a 16 TBC mesh and a 26 TBC mesh screen. Collect the material retained on the 26 TBC mesh screen as desired product.

In Vitro Dissolution

Uncoated formulations prepared in accordance with Example 4 gave the following results listed in Table 4B when subject to the following in vitro dissolution testing method.

Method:
1. Apparatus-USP Type II (Paddle), 50 rpm at 37° C.
2. Sampling Time: 1, 6, 12, 24, 36 hours
3. Media: 700 ml of SGF for one hour with a switch to 900 ml of SIF thereafter
4. Analytical Method: High Performance Liquid Chromatography Results:

TABLE 4B

| | Time (hours) | | | | |
| --- | --- | --- | --- | --- | --- |
| | 1 | 6 | 12 | 24 | 36 |
| Mean % Dissolved | 4.2 | 8.6 | 11.4 | 15.5 | 18.7 |

Simulated Tampering Process and Dissolution

The formulations prepared in accordance with Example 4 were subject to a simulated tampering process and then subject to the following dissolution testing method. The dissolution results for 45 minutes are listed in Table 4C. In the tampering process the uncoated Naltrexone Pellets were ground with a mortar and pestle (24 strokes) to a powder for this dissolution study.

Dissolution Method:
1. Apparatus-USP Type II (Paddle), 50 rpm at 37° C.
2. Sampling Time: 45 minutes
3. Media: 700 ml of SGF
4. Analytical Method: High Performance Liquid Chromatography Results:

TABLE 4C

| | Time (minute) |
| --- | --- |
| | 45 |
| Mean % Dissolved | 57 |

Crush:Intact Ratio

The crush-to-intact ratio is the ratio of the dissolution of the crushed pellets at 45 minutes to the dissolution of the intact pellets at 36 hours.
Crush-to-intact ratio results: 57%/18.7%=3.0

The naltrexone HCl pellets prepared in accordance with Example 4 and listed in Table 4A were further coated with a hydrophobic coating. The pellets were coated to weight gains of 5%, 10%, 15% and 20% with a hydrophobic coating (based on the Eudragit); and 25% with a hydrophobic coating (based on the Eudragit) and a color coating (Opadry). An example of the formulation having a 25% weight gain hydrophobic coating and color coating is listed in the following table.

TABLE 4D

Coated Pellet Formula for 25% Weight Gain

| Ingredient | Amt/unit (mg) | Amt/batch (kg) |
| --- | --- | --- |
| Naltrexone HCl 8 mg Pellets | 121.0 | 0.50 |
| Eudragit RS30D (solids) | 30.25 | 0.125 |
| TriEthyl Citrate | 6.05 | 0.025 |
| Cab-O-Sil | 1.5 | 0.0062 |
| Opadry Pink | 6.0 | 0.025 |
| Total | 164.8 | 0.68 |

The coated naltrexone HCl formulations of Example 4 were prepared using the following process:

Process

1. Functional Coating Dispersion: Mix Eudragit RS 30D with triethyl citrate to plasticize for 15 minutes. Disperse Cab-O-Sil in enough water to achieve a total of 20% w/w solids dispersion. Add the Cab-O-Sil dispersion to the Eudragit mixture.
2. Color Coating Dispersion: Mix Opadry with water to get a 10% w/w dispersion.
3. Functional Coating: Spray the Eudragit dispersion onto the Naltrexone pellets prepared above at 700 g scale using a fluid bed processor (GPCG-1) with the following parameter guidelines:
   Air Speed: 8.5 to 9.5 m/s
   Inlet Air Temperature: 35° C.
   Dispersion Spray Rate: 14 g/min
   Samples were taken at when the theoretical amount of dispersion was sprayed for 5%, 10%, 15%, 20%, and 25% weight gain.
4. Color Coating: Upon completion of the functional coating, spray Opadry dispersion onto the coated pellets using the following parameter guidelines:
   Air Speed: 8.5 m/s
   Inlet Air Temperature: 35-45° C.
   Dispersion Spray Rate: 8.5 g/min
5. Screening: Screen the pellets through a 14 US mesh screen and a 20 US mesh screen. Collect the material retained on the 20 US mesh screen as desired product.
6. Curing: Place the screened pellets and samples in an oven at 45° C. for 24 hours.

The pellets coated to a 5%, 10%, 15% and 20% weight gain were prepared in accordance with the above 20% formula and procedure using 6.05, 12.1, 18.15 and 24.2 mg of Eudragit RS30D (solids) per unit, respectively.

In Vitro Dissolution

The formulations coated with hydrophobic coating prepared in accordance with Example 4 gave the following results listed in Table 4E when subject to the following in vitro dissolution testing method.

Method:
1. Apparatus-USP Type II (Paddle), 50 rpm at 37° C.
2. Sampling Time: 1, 6, 12, 24, 36 hours
3. Media: 700 ml of SGF for one hour with a switch to 900 ml of SIF thereafter
4. Analytical Method: High Performance Liquid Chromatography Results:

TABLE 4E

|  |  | Time (hours) | | | | |
| --- | --- | --- | --- | --- | --- | --- |
|  |  | 1 | 6 | 12 | 24 | 36 |
| Mean % | Uncoated | 4.2 | 8.6 | 11.4 | 15.5 | 18.7 |
| Dissolved | 5% | 0.3 | 1.4 | 2.5 | 4.6 | 6.6 |
|  | 10% | 0.1 | 0.5 | 0.7 | 1.0 | 1.4 |
|  | 15% | 0.1 | 0.4 | 0.6 | 0.8 | 1.0 |
|  | 20% | 0.1 | 0.3 | 0.4 | 0.5 | 0.6 |
|  | 25% w/Opadry | 0.0 | 0.1 | 0.2 | 0.2 | 0.3 |

As can be seen from the dissolution results, the dissolution of the naltrexone pellets generally decreased with increased polymer coating levels.

Simulated Tampering Process and Dissolution

The formulations prepared in accordance with Example 4 were subject to a simulated tampering process and then subject to the following dissolution testing method. The dissolution results for 45 minutes are listed in Table 4F. In the tampering process the uncoated and coated Naltrexone Pellets were each separately ground with a mortar and pestle (24 strokes) to a powder for this dissolution study.

Dissolution Method:
1. Apparatus-USP Type II (Paddle), 50 rpm at 37° C.
2. Sampling Time: 45 minutes
3. Media: 700 ml of SGF
4. Analytical Method: High Performance Liquid Chromatography Results:

TABLE 4F

|  |  | Time (minute) 45 |
| --- | --- | --- |
| Mean % | Uncoated | 57 |
| Dissolved | 5% | 55 |
|  | 10% | 55 |
|  | 15% | 61 |
|  | 20% | 49 |
|  | 25% w/Opadry | 47 |

Crush:Intact Ratio

The crush-to-intact ratio is the ratio of the % dissolution of the crushed pellets at 45 minutes to the % dissolution of the intact pellets at 36 hours. The results are listed in Table 4G below.

Results:

TABLE 4G

| Crush:Intact Ratio | |
| --- | --- |
| Uncoated | 3.0 |
| 5% | 8.3 |
| 10% | 39.3 |
| 15% | 61.0 |
| 20% | 81.7 |
| 25% w/Opadry | 156.7 |

As can be seen from the dissolution results above, as the coating level increases, the amount of naltrexone released from the intact pellets decreases significantly (from over 18% to approximately 1% or less at 36 hours), yet when crushed, approximately 50% of the antagonist is still released and the Crush:Intact Ratio increases.

This product shows that adding a coating results in a significant decrease in the release of naltrexone from intact pellets, while retaining the ability to release substantial amounts of antagonist from crushed pellets.

Example 5

In Example 5, the formulation of Example 4 was repeated on the pilot scale under GMP conditions and used for in-vivo evaluation.

Pellets containing 8 mg of naltrexone were prepared as in Example 4 and coated with a hydrophobic coating to a 15% weight gain (based on Eudragit RS 30D). These pellets were then filled into size #2 capsules. The uncoated naltrexone HCl formulation of Example 5 is listed in the table below.

TABLE 5A

| Ingredient | Amt/unit (mg) | Amt/batch (kg) |
| --- | --- | --- |
| Naltrexone HCl | 8.0 | 2.40 |
| Eudragit RSPO | 84.0 | 25.20 |
| Stearyl Alcohol | 14.0 | 4.20 |
| Stearic Acid | 14.0 | 4.20 |
| Butylated Hydroxytoluene (BHT) | 1.0 | 0.30 |
| Total | 121.0 | 36.30 |

The uncoated pellets of Example 5 were prepared using the following process:

Process

1. Milling: Pass Stearyl Alcohol flakes through an oscillating mill equipped with a 16 mesh screen to achieve a powder that is easily blendable.

2. Blending: Mix Naltrexone HCl, Eudragit RSPO, milled stearyl alcohol, Stearic Acid, and BHT in a twin shell blender.

3. Extrusion: Continuously feed the blended material from Step 2 into a twin screw extruder (Leistritz ZSE-27) at a rate ranging from 4.0 kg/hr to 4.8 kg/hr. Extrude the blend at a barrel temperature range of 80° C. and 100° C. into strands ranging from 0.8 mm to 1.2 mm in diameter. Collect the extruded strands on a conveyor.

4. Cooling: Allow the strands to cool on the conveyor.

5. Pelletizing: Cut the cooled strands into pellets ranging from 0.8 mm to 1.4 mm in length using a Pelletizer.

6. Screening: Screen the pellets through a vibratory separator using a 16 TBC mesh and a 26 TBC mesh screen. Collect the material retained on the 26 TBC mesh screen as desired product.

The naltrexone HCl pellets prepared in accordance with Example 5 and listed in Table 5A were further coated with a hydrophobic coating. The pellets were coated to a 15% weight gain with a hydrophobic coating (based on Eudragit RS 30D). The coated pellets are listed in the table below.

TABLE 5B

Encapsulated Coated Pellet Formula for 15% Weight Gain

| Ingredient | Amt/unit (mg) | Amt/batch (kg) |
|---|---|---|
| Naltrexone HCl 8 mg Pellets | 121.0 | 10.00 |
| Eudragit RS30D (solids) | 18.2 | 1.50 |
| TriEthyl Citrate | 3.6 | 0.30 |
| Cab-O-Sil | 0.9 | 0.07 |
| Opadry Pink | 6.05 | 0.50 |
| Total | 149.7 | 12.37 |

Process

1. Functional Coating Dispersion: Mix Eudragit RS 30D with triethyl citrate to plasticize for 15 minutes. Disperse Cab-O-Sil in enough water to achieve a total of 20% w/w solids dispersion. Add the Cab-O-Sil dispersion to the Eudragit mixture.
2. Color Coating Dispersion: Mix Opadry with water to get a 10% w/w dispersion.
3. Functional Coating: Spray the Eudragit dispersion onto the Naltrexone pellets prepared above at 9 kg scale using a fluid bed processor (GPCG-15) with the following parameter guidelines:
   Air Flow: 700 to 780 CFM
   Inlet Air Temperature: 35° C.
   Dispersion Spray Rate: 115 to 135 g/min
4. Color Coating: Upon completion of the functional coating, spray Opadry dispersion onto the coated pellets using the following parameter guidelines:
   Air Flow: 750 to 760 CFM
   Inlet Air Temperature: 35-45° C.
   Dispersion Spray Rate: 75 to 95 g/min
5. Screening: Screen the pellets through a vibratory separator using 14 TBC mesh and a 26 TBC mesh screen. Collect the material retained on the 26 TBC mesh screen as desired product.
6. Encapsulation: Fill the screened pellets into hard gelatin capsules at a target weight of 149.7 mg.

In Vitro Dissolution (Intact Pellets)

Formulations coated with the hydrophobic coating in Example 5 in the form of bulk pellets and encapsulated pellets gave the following results listed in Table 5C when subjected to the following in vitro dissolution method.

Dissolution Method:
1. Apparatus-USP Type II (Paddle), 50 rpm at 37° C.
2. Sampling Time: 1, 2, 4, 8, 12, 24, 36 hours
3. Media: 700 ml of SGF for one hour with a switch to 900 ml of SIF thereafter
4. Analytical Method: High Performance Liquid Chromatography Results:

TABLE 5C

| | | Time (hours) | | | | | | |
|---|---|---|---|---|---|---|---|---|
| | | 1 | 2 | 4 | 8 | 12 | 24 | 36 |
| Mean % Dissolved | Bulk Pellets | 0.0 | 0.0 | 0.1 | 0.4 | 0.4 | 0.7 | 0.8 |
| | Encapsulated Pellets | 0.2 | 0.3 | 0.4 | 0.5 | 0.6 | 0.9 | 1.0 |

Simulated Tampering Process and Dissolution (Crushed Pellets)

Formulations prepared in accordance with Example 5 were subjected to a simulated tampering process and then subjected to the following dissolution testing method. In the tampering process, the coated naltrexone pellets were ground with a mortar and pestle (24 strokes) to a powder for this dissolution study.

Dissolution Method:
1. Apparatus-USP Type II (Paddle), 50 rpm at 37° C.
2. Sampling Time: 45 minutes
3. Media: 700 ml of SGF
4. Analytical Method: High Performance Liquid Chromatography Results:

TABLE 5D

| | Time (minute) 45 |
|---|---|
| Mean % Dissolved | 46.4 |

Crush:Intact Ratio

The crush-to-intact ratio is the ratio of the % dissolution of the crushed pellets at 45 minutes to the % dissolution of the intact pellets at 36 hours. The results are listed below.
Crush-to-intact ratio results: 46.4/0.8=58.0

In Vivo Human Pharmacokinetic/Bioavailability-Study

Capsules manufactured using the above process of this example and formula were used in a Clinical Study to determine the pharmacokinetics/bioavailability of the MEMs formulations under different conditions and then compared to the pharmacokinetics/bioavailability of Immediate-Release Naltrexone tablets. Human subjects were administered either intact Naltrexone HCl MEMs capsule (1 capsule or 5 capsules-fasted); crushed Naltrexone HCl MEMs (contents of 1 capsule ground-fasted); an immediate release Naltrexone HCl dosage form-tablet fasted; or 1 MEMs capsule intact in the fed state. The study is an open label, single-dose, 5-way, crossover study in 15 healthy subjects with 14 days washout between treatments. The treatments are designed as follows:
   A. 1×8 mg naltrexone MEM capsule, intact, in fasted state.
   B. 1×8 mg naltrexone MEM capsule, with the contents of the capsule crushed, in fasted state.
   C. 1×8 mg naltrexone MEM capsule, intact, in fed state.
   D. 5×8 mg (40 mg) naltrexone MEM capsules intact, in fasted state.
   E. 2×0.5 mg (1 mg) naltrexone immediate-release tablets, in fasted state.

Figure 2:
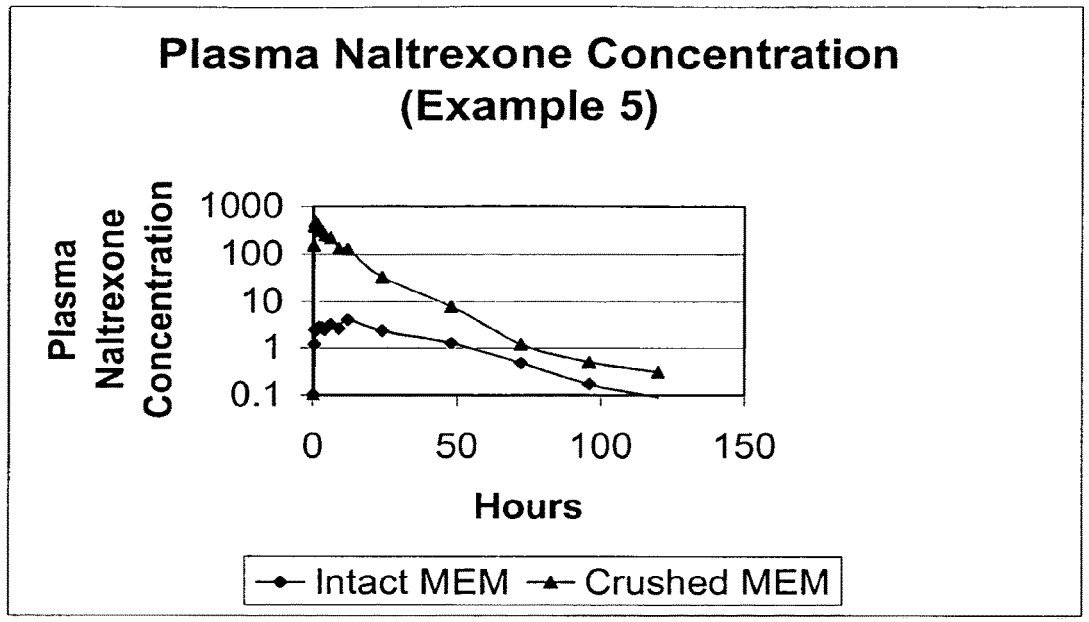
FIG. 2 is a graphical representation of the naltrexone concentration (pg/ml) versus time curve data for Example 5.

Plasma concentrations show that there is very small amount of release of naltrexone when naltrexone MEM pellets were taken intact. Naltrexone concentration (pg/ml) versus time curve data is depicted in FIG. 2. Naltrexone plasma levels were increased substantially when naltrexone pellets were taken orally crushed/ground in the fasted state. The mean Cmax Crushed MEMs (N=14)/Intact MEMs (N=15) capsule ratio is 112.34. Similarly, the mean AUCt crushed MEMs(N=14)/intact MEMs(N=15) capsule ratio is 31.55.

A in-vitro and in-vivo comparison of the uncoated MEMs of Example 1 and the coated MEMs of Example 5 is set forth in Table 5E, and 5F below:

TABLE 5E

| Formulation: | | | EXAMPLE 1<br>2 mg,<br>Uncoated | EXAMPLE 5<br>8 mg w/15%<br>Eudragit |
|---|---|---|---|---|
| In-Vitro | Intact 36 hr Capsule Release | | 0.124 mg | 0.08 mg |
| | Crushed | | 0.670 mg | 3.71 mg |
| | Crushed:Intact Ratio | | 5.4 | 46.4 |
| In-Vivo | AUC (pg/mL * hr) | Intact | 84.7 | 132.38* |
| | | Crushed | 373.4 | 4177.3* |
| | Cmax (pg/ML) | Intact | 5.3 | 4.44* |
| | | Crushed | 43.1 | 498.8* |

*normalized from 5 * 8 mg data

TABLE 5F

| | Intact Cap 8 mg Fast N = 15 | Crushed Cap 8 mg Fast 14 | Intact Cap 8 mg Fed 14 | Intact Cap 5 × 8 mg Fast 15 | IR Tablet 2 × 0.5 mg Fast 6 |
|---|---|---|---|---|---|
| Cmax (pg/mL) | 3.6 | 498.8 | 7.2 | 22.2 | 140.5 |
| AUCt (pg · hr/mL) | 51.9 | 4177.3 | 123.8 | 661.9 | 424.5 |

Example 6

Methacrylic Copolymer Coated 2 mg Naltrexone HCl MEM's

The uncoated naltrexone HCl formulation of Example 6 is listed in Table 6A below:

TABLE 6A

Pellet Formula

| Ingredient | Amt/unit (mg) | Amt/batch (kg) |
|---|---|---|
| Naltrexone HCl | 2.0 | 0.10 |
| Eudragit RSPO | 88.0 | 4.40 |
| Stearyl Alcohol | 15.0 | 0.75 |
| Stearic Acid | 15.0 | 0.75 |
| Butylated Hydroxytoluene (BHT) | 1.0 | 0.05 |
| Total | 121.0 | 6.05 |

The naltrexone HCl formulation of Example 6 was prepared using the following process:

Process

1. Milling: Pass the stearyl alcohol flakes through an oscillating mill equipped with a 16 mesh screen to achieve a powder that is easily blendable.
2. Blending: Mix Naltrexone HCl, Eudragit RSPO, milled Stearyl Alcohol, Stearic Acid and BHT in a twin shell blender.
3. Extrusion: Continuously feed the blended material from Step 2 into a twin screw extruder (Leistritz ZSE-27) at a rate ranging from 2.9 kg/hr to 4.8 kg/hr. Extrude the blend at a barrel temperature range of 95° C. and 105° C. into strands approximately 1 mm in diameter. Collect the extruded strands on a conveyor.
4. Cooling: Allow the strands to cool on the conveyor.
5. Pelletizing: Cut the cooled strands into pellets approximately 1 mm in length using a Pelletizer.
6. Screening: Screen the pellets through a vibratory separator using a 16 TBC mesh and a 26 TBC mesh screen. Collect the material retained on the 26 TBC mesh screen as desired product.

In Vitro Dissolution (Intact Pellets)

Formulations prepared in accordance with Example 6 gave the following dissolution results listed in Table 6B when subject to the following in vitro dissolution testing method.

Method:
1. Apparatus-USP Type II (Paddle), 50 rpm at 37° C.
2. Sampling Time: 1, 2, 4, 8, 12, 18, 24, 36 hours
3. Media: 700 ml SGF for one hour/900 ml SIF thereafter
4. Analytical Method: High Performance Liquid Chromatography Results:

TABLE 6B

| | Time (hours) | | | | | | | |
|---|---|---|---|---|---|---|---|---|
| | 1 | 2 | 4 | 8 | 12 | 18 | 24 | 36 |
| Mean % Dissolved | 2.1 | 2.6 | 2.9 | 3.2 | 3.8 | 4.2 | 4.7 | 5.3 |

Simulated Tampering and Dissolution Process (Crushed Pellets)

Formulations prepared in accordance with Example 6 were subject to a simulated tampering process and the subject to the following in vitro dissolution testing method. The dissolution results for 1 hour are listed in Table 6C. In the tampering process, naltrexone pellets were ground with a mortar and pestle (24 strokes) to a powder for this dissolution study.

Dissolution Method:
1. Apparatus-USP Type II (Paddle), 50 rpm at 37° C.
2. Sampling Time: 45 minutes
3. Media: 700 ml of SGF
4. Analytical Method: High Performance Liquid Chromatography Results:

TABLE 6C

| | Time (minute)<br>45 |
|---|---|
| Mean % Dissolved | 31 |

Crush:Intact Ratio

The crush-to-intact ratio is the ratio of the % dissolution of the crushed pellets at 45 minutes to the % dissolution of the intact pellets at 36 hours.

Crush-to-intact ratio: 31%/5.3%=5.8:1

Naltrexone HCl pellets prepared in accordance with Example 6 and listed in table 6A were further coated with a hydrophobic coating. The pellets were coated to a 15% weight gain with a hydrophobic coating (based on Eudragit RS 30D). The formulation having a 15% weight gain is listed in the following table:

TABLE 6D

Coated Pellet Formula for 15% Weight Gain

| Ingredient | Amt/unit (mg) | Amt/batch (kg) |
|---|---|---|
| Naltrexone HCl 2 mg Pellets | 121.0 | 0.500 |
| Eudragit RS30D (solids) | 18.2 | 0.075 |
| TriEthyl Citrate | 3.6 | 0.015 |
| Cab-O-Sil | 0.9 | 0.004 |
| Total | 143.7 | 0.594 |

The coated naltrexone HCl formulations of Example 6 were prepared using the following process:

Process

1. Functional Coating Dispersion: Mix Eudragit RS 30D with triethyl citrate to plasticize for 15 minutes. Disperse Cab-O-Sil in enough water to achieve a total of 20% w/w solids dispersion. Add the Cab-O-Sil dispersion to the Eudragit mixture.
2. Functional Coating: Spray the Eudragit dispersion onto the Naltrexone pellets prepared above at 700 g scale using a fluid bed processor (GPCG-1) with the following parameter guidelines:
    Air Speed: 9.0 m/s
    Inlet Air Temperature: 35° C.
    Dispersion Spray Rate: 8.8 g/min
3. Screening: Screen the pellets through a 14 US mesh screen and a 20 US mesh screen. Collect the material retained on the 20 US mesh screen as desired product.

In Vitro Dissolution (Intact Pellets)

Formulations coated with hydrophobic coating prepared in accordance Example 6 gave the following results listed in table 6E when subject to the following in vitro dissolution testing method.

Method:
1. Apparatus-USP Type II (Paddle), 50 rpm at 37° C.
2. Sampling Time: 1, 2, 4, 8, 12, 24, 36 hours
3. Media: 700 ml of SGF for one hour with a switch to 900 ml SIF thereafter
4. Analytical Method: High Performance Liquid Chromatography Results:

TABLE 6E

| | Time (hours) | | | | | | |
|---|---|---|---|---|---|---|---|
| | 1 | 2 | 4 | 8 | 12 | 24 | 36 |
| Mean % Dissolved | <0.6* | <0.6 | <0.6 | <0.6 | <0.6 | <0.6 | <0.6 |

The limit of detection is 0.6%

Simulated Tampering and Dissolution Process (Crushed Pellets)

Coated formulations prepared in accordance with Example 6 were subject to a simulated tampering process and then subject to the following dissolution method. The dissolution results for 1 hour is listed in Table 6F. In the tampering process the naltrexone pellets were ground with a mortar and pestle (24 strokes) to a powder for this dissolution study.

Dissolution Method: Same as above
Results:

TABLE 6F

| | Time (hour) |
|---|---|
| | 1 |
| Mean % Dissolved | 7 |

Crush:Intact Ratio

The crush-to-intact ratio is the ratio of the % dissolution of the crushed pellets at 1 hour to the % dissolution of the intact pellets at 36 hours.

Crush-to-intact ratio: 7%/0.6%=12 (note: since no detectable naltrexone was observed from the intact pellets, the Crush/Intact ratio could be much more than 12) I do not understand.

Example 7

Methacrylic Copolymer then Surelease Coated 8 mg Naltrexone HCl MEM's

In Example 7, a two-stage sequential coating of the MEMs first with Eudragit RS 30D to a weight gain of 15%, then followed by Surelease to an additional 10% weight gain (based on the uncoated extruded pellets) was prepared. Pellets containing 8 mg of Naltrexone were prepared as in Example 5 were coated with a methacrylic copolymer (Eudragit RS 30D) to a 15% weight gain, followed by ethylcellulose (Surelease) to a 10% weight gain. This product shows significant decrease in the release of Naltrexone from intact pellets while enhancing the higher release from crushed pellets. The uncoated naltrexone HCl formulation of Example 7 is listed in table 7A below.

TABLE 7A

Pellet Formula

| Ingredient | Amt/unit (mg) | Amt/batch (kg) |
|---|---|---|
| Naltrexone HCl | 8.0 | 2.40 |
| Eudragit RSPO | 84.0 | 25.20 |
| Stearyl Alcohol | 14.0 | 4.20 |
| Stearic Acid | 14.0 | 4.20 |
| Butylated Hydroxytoluene (BHT) | 1.0 | 0.30 |
| Total | 121.0 | 36.30 |

The uncoated naltrexone HCl formulation of Example 7 was prepared using the following process:

Process

1. Milling: Pass the stearyl alcohol flakes through an oscillating mill equipped with a 16 mesh screen to achieve a powder that is easily blendable.
2. Blending: Mix Naltrexone HCl, Eudragit RSPO, milled Stearyl Alcohol, Stearic Acid and BHT in a twin shell blender.
3. Extrusion: Continuously feed the blended material from Step 2 into a twin screw extruder (Leistritz ZSE-27) at a rate ranging from 4.0 kg/hr to 4.8 kg/hr. Extrude the blend at a barrel temperature range of 85° C. and 90° C. into strands ranging from 0.8 mm to 1.2 mm in diameter. Collect the extruded strands on a conveyor.
4. Cooling: Allow the strands to cool on the conveyor.
5. Pelletizing: Cut the cooled strands into pellets ranging from 0.8 mm to 1.4 mm in length using a Pelletizer.
6. Screening: Screen the pellets through a vibratory separator using a 16 TBC mesh and a 26 TBC mesh screen. Collect the material retained on the 26 TBC mesh screen as desired product.

The naltrexone HCl pellets prepared in accordance with Example 7 and listed in table 7A were further coated with the hydrophobic coating. The pellets were coated to a 15% weight gain with a methacrylic copolymer followed by a 10% weight gain (based on the uncoated pellet) with ethylcellulose. The coated pellets are listed in the table below.

TABLE 7B

Coated Pellet Formula for 15% Weight Gain
Methacrylic Copolymer followed by 10%
Weight Gain Ethylcellulose

| Ingredient | Amt/unit (mg) | Amt/batch (kg) |
| --- | --- | --- |
| Naltrexone HCl 8 mg Pellets (lot # 955-25) | 121.0 | 0.500 |
| Eudragit RS30D (solids) | 18.2 | 0.075 |
| TriEthyl Citrate | 3.6 | 0.015 |
| Cab-O-Sil | 0.9 | 0.004 |
| Surelease | 12.1 | 0.050 |
| Opadry Pink | 6.05 | 0.025 |
| Total | 161.85 | 0.669 |

The coated naltrexone HCl formulation was prepared using the following process:

Process

1. Methacrylic Coating Dispersion: Mix Eudragit RS 30D with triethyl citrate to plasticize for 15 minutes. Disperse Cab-O-Sil in enough water to achieve a total of 20% w/w solids dispersion. Add the Cab-O-Sil dispersion to the Eudragit mixture.
2. Ethylcellulose Coating Dispersion: Mix Surelease with enough water to achieve a total of 15% w/w solids dispersion.
3. Color Coating Dispersion: Mix Opadry with water to achieve a 10% w/w dispersion.
4. Methacrylic Coating: Spray the Eudragit dispersion onto the Naltrexone pellets prepared above at 700 g scale using a fluid bed processor (GPCG-1) with the following parameter guidelines:
   Air Speed: 8.8 to 9.0 m/s
   Inlet Air Temperature: 35° C.
   Dispersion Spray Rate: 9.6 g/min
5. Ethylcellulose Coating: Upon completion of the Eudragit coating, spray the Surelease dispersion onto the coated pellets using the following parameter guidelines:
   Air Speed: 9.0 m/s
   Inlet Air Temperature: 40° C. to 45° C.
   Dispersion Spray Rate: 9.2 to 9.6 g/min
6. Color Coating: Upon completion of the functional coating, spray Opadry dispersion onto the coated pellets using the following parameter guidelines:
   Air Flow: 8.8 to 9.0 m/s
   Inlet Air Temperature: 50° C.
   Dispersion Spray Rate: 9.3 g/min
7. Screening: Screen the pellets through a 14 US mesh screen and a 20 US mesh screen. Collect the material retained on the 20 US mesh screen as desired product.

In Vitro Dissolution (Intact Pellets)

Formulations coated with hydrophobic coating (methacrylic copolymer coating and ethylcellulose coating) prepared in accordance with Example 7 gave the following results listed in table 7C when subjected to the following in vitro dissolution method.

Method:
1. Apparatus-USP Type II (Paddle), 50 rpm at 37° C.
2. Sampling Time: 1, 2, 4, 8, 12, 24, 36 hours
3. Media: 700 ml of SGF for one hour with a switch to 900 ml of SIF thereafter
4. Analytical Method: High Performance Liquid Chromatography Results:

TABLE 7C

| | Time (hours) | | | | | | |
| --- | --- | --- | --- | --- | --- | --- | --- |
| | 1 | 2 | 4 | 8 | 12 | 24 | 36 |
| Mean % Dissolved | <0.15* | <0.15 | <0.15 | <0.15 | <.15 | 0.2 | 0.4 |

*below limit of detection (0.15%)

Simulated Tampering Process and Dissolution (Crushed Pellets)

Formulations prepared in accordance with Example 7 were subject to a simulated tampering process and then subject to the following dissolution testing method. In the tampering process, the coated naltrexone pellets were ground with a mortar and pestle (24 strokes) to a powder for this dissolution study. The dissolution results are listed in table 7D.

Dissolution Method:
1. Apparatus-USP Type II (Paddle), 50 rpm at 37° C.
2. Sampling Time: 45 minutes
3. Media: 700 ml of SGF
4. Analytical Method: High Performance Liquid Chromatography Results:

TABLE 7D

| | Time (minute) 45 |
| --- | --- |
| Mean % Dissolved | 37 |

Crush:Intact Ratio

The crush-to-intact ratio is the ratio of the % dissolution of the crushed pellets at 45 minutes to the % dissolution of the intact pellets at 36 hours.

Crush-to-intact ratio: 92.5

Example 8

Surelease then Methacrylic Copolymer Coated 8 mg Naltrexone HCl MEM's

Pellets containing 8 mg of Naltrexone were prepared as in Example 5 and coated with ethylcellulose (Surelease) to a 10% weight gain, followed by methacrylic copolymer (Eudragit RS 30D) to a 15% weight gain (based on the uncoated pellets). This product shows significant decrease in the release of Naltrexone from intact pellets while enhancing the higher release from crushed pellets.

The uncoated naltrexone HCl formulation of Example 8 is listed in Table 8A below.

TABLE 8A

Pellet Formula

| Ingredient | Amt/unit (mg) | Amt/batch (kg) |
| --- | --- | --- |
| Naltrexone HCl | 8.0 | 2.40 |
| Eudragit RSPO | 84.0 | 25.20 |
| Stearyl Alcohol | 14.0 | 4.20 |
| Stearic Acid | 14.0 | 4.20 |
| Butylated Hydroxytoluene (BHT) | 1.0 | 0.30 |
| Total | 121.0 | 36.30 |

The uncoated naltrexone HCl formulation of Example 8 was prepared using the following process:

Process

1. Milling: Pass the stearyl alcohol flakes through an oscillating mill equipped with a 16 mesh screen to achieve a powder that is easily blendable.
2. Blending: Mix Naltrexone HCl, Eudragit RSPO, milled Stearyl Alcohol, Stearic Acid and BHT in a twin shell blender.
3. Extrusion: Continuously feed the blended material from Step 2 into a twin screw extruder (Leistritz ZSE-27) at a rate ranging from 4.0 kg/hr to 4.8 kg/hr. Extrude the blend at a barrel temperature range of 85° C. and 90° C. into strands ranging from 0.8 mm to 1.2 mm in diameter. Collect the extruded strands on a conveyor.
4. Cooling: Allow the strands to cool on the conveyor.
5. Pelletizing: Cut the cooled strands into pellets ranging from 0.8 mm to 1.4 mm in length using a Pelletizer.
6. Screening: Screen the pellets through a vibratory separator using a 16 TBC mesh and a 26 TBC mesh screen. Collect the material retained on the 26 TBC mesh screen as desired product.

The naltrexone HCl pellets prepared in accordance with Example 8 and listed in table 8A were further coated with the hydrophobic coating. The pellets were coated to a 10% weight gain with ethylcellulose followed by a 15% weight gain with methacrylic copolymer (based on the uncoated pellets). The coated pellets are listed in the table below.

TABLE 8B

Coated Pellet Formula for 10% Weight Gain Ethylcellulose followed by 15% Weight Gain Methacrylic Copolymer

| Ingredient | Amt/unit (mg) | Amt/batch (kg) |
| --- | --- | --- |
| Naltrexone HCl 8 mg Pellets | 121.0 | 0.500 |
| Surelease | 12.1 | 0.050 |
| Eudragit RS30D (solids) | 18.2 | 0.075 |
| TriEthyl Citrate | 3.6 | 0.015 |
| Cab-O-Sil | 0.9 | 0.004 |
| Opadry Pink | 6.05 | 0.025 |
| Total | 161.85 | 0.669 |

The coated naltrexone HCl formulation of Example 8 was prepared using the following process:

Process

1. Ethylcellulose Coating Dispersion: Mix Surelease with enough water to achieve a total of 15% w/w solids dispersion.
2. Methacrylic Coating Dispersion: Mix Eudragit RS 30D with triethyl citrate to plasticize for 15 minutes. Disperse Cab-O-Sil in enough water to achieve a total of 20% w/w solids dispersion. Add the Cab-O-Sil dispersion to the Eudragit mixture.
3. Color Coating Dispersion: Mix Opadry with water to achieve a 10% w/w dispersion.
4. Ethylcellulose Coating: Spray the Surelease dispersion onto the coated pellets at 700 g scale using a fluid bed processor (GPCG-1) with the following parameter guidelines:
   Air Speed: 9.0 to 9.2 m/s
   Inlet Air Temperature: 50° C.
   Dispersion Spray Rate: 10 g/min
5. Methacrylic Coating: Upon completion of the Surelease coating, spray the Eudragit dispersion onto the Naltrexone pellets prepared above using a fluid bed processor using the following parameter guidelines:
   Air Speed: 9.0 m/s
   Inlet Air Temperature: 35° C.
   Dispersion Spray Rate: 10.7 g/min
6. Color Coating: Upon completion of the functional coating, spray Opadry dispersion onto the coated pellets using the following parameter guidelines:
   Air Speed: 750 to 760 CFM
   Inlet Air Temperature: 50° C.
   Dispersion Spray Rate: 9.2 g/min
7. Screening: Screen the pellets through a 14 US mesh screen and a 20 US mesh screen. Collect the material retained on the 20 US mesh screen as desired product.
8. Curing: Place the screened pellets in an oven at 45° C., remove a portion at 24 hours and the remaining material at 48 hours.

In Vitro Dissolution (Intact Pellets)

The formulations coated with hydrophobic coating (ethylcellulose and methacrylic copolymer coatings) prepared in accordance with Example 8 gave the following dissolution results listed in table 8C when subject to the following dissolution method.

Method:
1. Apparatus-USP Type II (Paddle), 50 rpm at 37° C.
2. Sampling Time: 1, 2, 4, 8, 12, 24, 36 hours 3. Media: 700 ml of SGF for one hour with a switch to 900 ml of SIF thereafter
4. Analytical Method: High Performance Liquid Chromatography Results:

TABLE 8C

| | Time (hours) | | | | | | |
|---|---|---|---|---|---|---|---|
| | 1 | 2 | 4 | 8 | 12 | 24 | 36 |
| Mean % Dissolved | 0.1 | 0.1 | 0.2 | 0.3 | 0.3 | 0.5 | 0.7 |

Simulated Tampering Process and Dissolution (Crushed Pellets)

Formulations prepared in accordance with Example 8 were subjected to a simulated tampering process and then subject to the following dissolution testing method. In the tampering process, the coated naltrexone pellets were ground with a mortar and pestle (24 strokes) to a powder for this dissolution study. The dissolution results are listed in Table 8D.

Dissolution Method:
1. Apparatus-USP Type II (Paddle), 50 rpm at 37° C.
2. Sampling Time: 45 minutes
3. Media: 700 ml of SGF
4. Analytical Method: High Performance Liquid Chromatography Results:

TABLE 8D

| | Time (minute) 45 |
|---|---|
| Mean % Dissolved | 30 |

Crush:Intact Ratio

The crush-to-intact ratio is the ratio of the % dissolution of the crushed pellets at 45 minutes to the % dissolution of the intact pellets at 36 hours. The results are listed below.
Crush-to-intact ratio: 42.9

Comparison of the Three 25% Coated Pellets

In Examples 4, 7, and 8, naltrexone MEM pellets were coated with a total of 25% coating with different coating materials or sequence. The crushed-to-intact ratio are compared as follows:

TABLE 8F

| | 25% Eudragit RS | 15% Eudragit RS then 10% Surelease | 10% Surelease then 15% Eudragit RS |
|---|---|---|---|
| % Dissolved Crushed | 47 | 37 | 43 |
| % Dissolved Intact | 0.3 | 0.3 | 0.7 |
| Crush/Intact Ratio | 157 | 93 | 43 |

Based on in-vitro dissolution data of crushed and intact MEM pellets, 25% Eudragit RS coating appears to be slightly better than the combination coatings.

Example 9

Controlled Release Oxycodone Hydrochloride 10 mg Tablets can be prepared in this prophetic example as follows. Organic Manufacture Oxycodone hydrochloride (10 mg/tablet) and spray dried lactose (71.25 mg/tablet) are transferred into an appropriate sized mixer and mixed for approximately 6 minutes. Eudragit® RS PM powder (6 mg/tablet) is dispersed in ethanol. While the powders are mixing, the powders are granulated with the dispersion and the mixing continued until a moist granular mass is formed. Additional ethanol is added if needed to reach granulation end point. The granulation is transferred to a fluid bed dryer and dried at 30° C., and then passed through a 12-mesh screen. The remaining Eudragit® RS PM (9 mg/tablet) is dispersed in a solvent of 90 parts ethanol and 10 parts purified water; and sprayed onto the granules in the fluid bed granulator/dryer at 30° C. Next, the granulate is passed through a 12-mesh screen. Stearyl alcohol (25 mg/tablet) is melted at approximately 60-70° C. The warm granules are returned to the mixer. While mixing, the melted stearyl alcohol is added. The coated granules are removed from the mixer and allowed to cool. Thereafter, they are passed through a 12-mesh screen. Next, the granulate is mixed with naltrexone particles of Example 5 and pharmaceutically desirable tableting excipients, e.g., talc and magnesium stearate, in a suitable blender and compressed into tablets.

Example 10

Method of Treating Pain

The oral dosage form according to the present invention can be administered to a patient to provide pain relief. The oral dosage form may comprise an orally effective amount of an opioid agonist and an opioid antagonist that is rendered substantially non-releasable. The coating of the antagonist-containing particles serves to beneficially reduce the leakage of antagonist from intact antagonist-containing particles.

When the oral dosage form is administered orally and delivered to the GI tract of a patient in need of pain therapy, the opioid agonist is released from the dosage form during normal digestion, providing analgesia to the patient. But the opioid antagonist, because it has been rendered substantially non-releasable, is substantially not released during its transit through the GI tract. Preferably, the substantially non-releasable form of the antagonist is resistant to laxatives (mineral oil) used to manage delayed colonic transit, or achlorhydria states. Patients who take the oral dosage form as directed, without tampering with it (e.g. by mechanical agitation, heating, or dissolution in a solvent), will not have the opioid antagonist absorbed in sufficient amount during any time interval during the dosing of the formulation that would result in reduction of the analgesic effectiveness of the opioid agonist. In other words, the amount of opioid antagonist released from the intact dosage form (when orally administered) and absorbed from the GI tract and accumulated in the patient's body, would not rise to a level which significantly impacts or changes the analgesic efficacy of the dose of opioid agonist included in the dosage form.

Example 11

Method of Preventing Abuse of an Opioid Agonist

The oral dosage form according to the present invention may be used to prevent the abuse potential of an opioid agonist contained therein. The oral dosage form comprises an opioid agonist in combination with an opioid antagonist. The opioid antagonist is present in a form that is substantially non-releasable during digestion. Thus, when the oral dosage form is delivered to the GI tract orally as intended, without having been tampered with, the antagonist is substantially prevented from being released into the GI system. But if the oral dosage form is tampered with, e.g., by mechanical agitation (e.g., crushing, shearing, grinding), heat (e.g., temperatures of greater than 45° C., preferably between 45° to 50° C.), or dissolution of the dosage form in a solvent (with or without heating), the opioid antagonist becomes available to blunt the opioid effects. Thus, when the dosage form is tampered with, and then administered orally, intranasally, parenterally or sublingually, the effect of the opioid agonist is at least partially blocked by the opioid antagonist.

Example 12

Hydromorphone HCl Controlled Release Capsules with naltrexone HCl Pellets can be prepared in this prophetic example as follows. The formulation is listed in Table 12A below:

TABLE 12A

| Ingredient | Amt/unit (mg) |
| --- | --- |
| Hydromorphone HCl | 12.0 |
| Eudragit RSPO | 76.5 |
| Ethylcellulose | 4.5 |
| Stearyl Alcohol | 27.0 |
| Opadry Pink | 6.0 |
| Naltrexone HCl Pellets (Example 5) | 149.7 |
| Total | 275.7 |
| Hard Gelatin Capsules | √ |

The capsules of Example 5 are prepared using the following process:

Process

| 1. | Milling | Pass Stearyl Alcohol flakes through an impact mill. |
| --- | --- | --- |
| 2. | Blending | Mix Hydromorphone HCl, Eudragit, Ethycellulose and milled Stearyl Alcohol in a twin shell blender. |
| 3. | Extruding | Continuously feed the blended material into a twin screw extruder and collect the resultant strands on a conveyor. |
| 4. | Cooling | Allow the strands to cool on the conveyor. |
| 5. | Pelletizing | Cut the cooled strands into pellets using a Pelletizer. |
| 6. | Screening | Screen the pellets and collect desired sieve portion. |
| 7. | Filmcoating | Spray a water dispersion of Opadry Pink onto the opioid pellets in a fluid bed. |
| 8. | Encapsulating | Fill the coated extruded Hydromorphone HCl pellets at 126 mg and Naltrexone HCl pellets (from Example 5) at 149.7 mg into hard gelatin capsules. |

Variations of the present invention will be apparent to those skilled in the art and are meant to be within the scope of the claims appended hereto.

Example 13

Example 13a

In Example 13a, the naltrexone HCl pellets prepared in accordance with Example 5 and listed in Table 5A were further coated with a hydrophobic coating. The pellets were coated to a 25% weight gain with a hydrophobic coating (based on Eudragit RS 30D). The coated pellets are listed in the table below.

TABLE 13A

Encapsulated Coated Pellet Formula for 25% Weight Gain

| Ingredient | Amt/unit (mg) | Amt/batch (kg) |
| --- | --- | --- |
| Naltrexone HCl 8 mg Pellets | 121.0 | 7.00 |
| Eudragit RS30D (solids) | 30.25 | 1.75 |
| TriEthyl Citrate | 6.05 | 0.35 |
| Cab-O-Sil | 1.51 | 0.09 |
| Opadry White Y-5-18024A | 6.05 | 0.35 |
| Total | 164.86 | 9.54 |

The process utilized in preparing the pellets of Example 13A follows:

Process

1. Functional Coating Dispersion: Mix Eudragit RS 30D with triethyl citrate to plasticize for 15 minutes. Disperse Cab-O-Sil in enough water to achieve a total of 20% w/w solids dispersion. Add the Cab-O-Sil dispersion to the Eudragit mixture.
2. Color Coating Dispersion: Mix Opadry with water to get a 10% w/w dispersion.
3. Functional Coating: Spray the Eudragit dispersion onto the Naltrexone pellets prepared above at 9 kg scale using a fluid bed processor (GPCG-15) with the following parameter guidelines:
   Air Flow: 400 to 450 CFM
   Inlet Air Temperature: 40° C.
   Dispersion Spray Rate: 75 to 90 g/min
4. Color Coating: Upon completion of the functional coating, spray Opadry dispersion onto the coated pellets using the following parameter guidelines:
   Air Flow: 400 to 450 CFM
   Inlet Air Temperature: 50-55° C.
   Dispersion Spray Rate: 60 to 70 g/min
5. Screening: Screen the pellets through a vibratory separator using 14 TBC mesh and a 26 TBC mesh screen. Collect the material retained on the 26 TBC mesh screen as desired product.
6. Encapsulation: Fill the screened pellets into hard gelatin capsules at a target weight of 164.86 mg.

In Vitro Dissolution (Intact Pellets)

Formulations coated with the hydrophobic coating in Example 13a in the form of bulk pellets and encapsulated pellets gave the following results listed in Table 13B when subjected to the following in vitro dissolution method.

Dissolution Method:
1. Apparatus-USP Type II (Paddle), 50 rpm at 37° C.
2. Sampling Time: 1, 2, 4, 8, 12, 24, 36 hours
3. Media: 700 ml of SGF for one hour with a switch to 900 ml of SIF thereafter
4. Analytical Method: High Performance Liquid Chromatography Results:

TABLE 13B

| | | Time (hours) | | | | | | |
|---|---|---|---|---|---|---|---|---|
| | | 1 | 2 | 4 | 8 | 12 | 24 | 36 |
| Mean % Dissolved | Bulk Pellets | 0.0 | 0.0 | 0.1 | 0.2 | 0.3 | 0.3 | 0.3 |
| | Encapsulated Pellets | 0.0 | 0.0 | 0.1 | 0.2 | 0.4 | 0.4 | 0.5 |

Simulated Tampering Process and Dissolution (Crushed Pellets)

Formulations prepared in accordance with Example 13a were subjected to a simulated tampering process and then subjected to the following dissolution testing method. In the tampering process, the coated naltrexone pellets were ground with a mortar and pestle (24 strokes) to a powder for this dissolution study.

Dissolution Method:
1. Apparatus-USP Type II (Paddle), 50 rpm at 37° C.
2. Sampling Time: 45 minutes
3. Media: 700 ml of SGF
4. Analytical Method: High Performance Liquid Chromatography Results:

TABLE 13C

| | Time (minute) 45 |
|---|---|
| Mean % Dissolved | 27 |

Crush:Intact Ratio

The crush-to-intact ratio is the ratio of the % dissolution of the crushed pellets at 45 minutes to the % dissolution of the intact pellets at 36 hours. The results are listed below.

Crush-to-intact ratio results: 27.0/0.5=54

Example 13b

In Example 13b, the naltrexone HCl pellets prepared in accordance with Example 5 and listed in Table 5A were further coated with a hydrophobic coating. The pellets were coated to a 30% weight gain with a hydrophobic coating (based on Surelease E-7-10901).

The coated pellets are listed in the table below.

TABLE 13D

Encapsulated Coated Pellet Formula for 30% Weight Gain

| Ingredient | Amt/unit (mg) | Amt/batch (kg) |
|---|---|---|
| Naltrexone HCl 8 mg Pellets | 121.0 | 7.00 |
| Surelease (solids) | 36.3 | 2.10 |
| Opadry White Y-5-18024A | 6.05 | 0.35 |
| Total | 163.35 | 9.45 |

The process utilized in preparing the pellets of Example 13A follows:

Process

1. Functional Coating Dispersion: Mix Eudragit RS 30D with triethyl citrate to plasticize for 15 minutes. Disperse Cab-O-Sil in enough water to achieve a total of 20% w/w solids dispersion. Add the Cab-O-Sil dispersion to the Eudragit mixture.
2. Color Coating Dispersion: Mix Opadry with water to get a 10% w/w dispersion.
3. Functional Coating: Spray the Eudragit dispersion onto the Naltrexone pellets prepared above at 9 kg scale using a fluid bed processor (GPCG-15) with the following parameter guidelines:
   Air Flow: 400 to 450 CFM
   Inlet Air Temperature: 40° C.
   Dispersion Spray Rate: 75 to 90 g/min
4. Color Coating: Upon completion of the functional coating, spray Opadry dispersion onto the coated pellets using the following parameter guidelines:
   Air Flow: 400 to 450 CFM
   Inlet Air Temperature: 50-55° C.
   Dispersion Spray Rate: 60 to 70 g/min
5. Screening: Screen the pellets through a vibratory separator using 14 TBC mesh and a 26 TBC mesh screen. Collect the material retained on the 26 TBC mesh screen as desired product.
6. Encapsulation: Fill the screened pellets into hard gelatin capsules at a target weight of 164.86 mg.

In Vitro Dissolution (Intact Pellets)

Formulations coated with the hydrophobic coating in Example 13b in the form of bulk pellets and encapsulated pellets gave the following results listed in Table 13E when subjected to the following in vitro dissolution method.

Dissolution Method:
1. Apparatus-USP Type II (Paddle), 50 rpm at 37° C.
2. Sampling Time: 1, 2, 4, 8, 12, 24, 36 hours
3. Media: 700 ml of SGF for one hour with a switch to 900 ml of SIF thereafter
4. Analytical Method: High Performance Liquid Chromatography Results:

TABLE 13E

| | | Time (hours) | | | | | | |
|---|---|---|---|---|---|---|---|---|
| | | 1 | 2 | 4 | 8 | 12 | 24 | 36 |
| Mean % Dissolved | Bulk Pellets | 0.3 | 0.3 | 0.4 | 0.7 | 0.9 | 1.4 | 1.7 |
| | Encapsulated Pellets | 0.4 | 0.5 | 0.6 | 0.7 | 0.9 | 1.3 | 1.6 |

Simulated Tampering Process and Dissolution
(Crushed Pellets)

Formulations prepared in accordance with Example 13b were subjected to a simulated tampering process and then subjected to the following dissolution testing method. In the tampering process, the coated naltrexone pellets were ground with a mortar and pestle (24 strokes) to a powder for this dissolution study.

Dissolution Method:
5. Apparatus-USP Type II (Paddle), 50 rpm at 37° C.
6. Sampling Time: 45 minutes
7. Media: 700 ml of SGF
8. Analytical Method: High Performance Liquid Chromatography Results:

TABLE 13F

|  | Time (minute) 45 |
|---|---|
| Mean % Dissolved | 26 |

Crush:Intact Ratio

The crush-to-intact ratio is the ratio of the % dissolution of the crushed pellets at 45 minutes to the % dissolution of the intact pellets at 36 hours. The results are listed below.
Crush-to-intact ratio results: 26.0/1.6=16.3

In Vivo Human
Pharmacokinetic/Bioavailability-Study

Capsules manufactured using the above process of Examples 13a and b were used in two separate clinical studies to determine the pharmacokinetics/bioavailability of the MEMs formulations under different conditions and then compared to the pharmacokinetics/bioavailability of Immediate-Release Naltrexone tablets. Human subjects were administered either intact Naltrexone HCl MEMs capsule (1 capsule-fasted or 5 capsules-fasted); crushed Naltrexone HCl MEMs (contents of 1 capsule ground-fasted); an immediate release Naltrexone HCl dosage form-tablet fasted; or 1 MEMs capsule intact in the fed state. These studies were open label, single-dose, 5-way, crossover study in healthy subjects. The treatments are designed as follows:
A. 1×8 mg naltrexone MEM capsule, intact, in fasted state.
B. 1×8 mg naltrexone MEM capsule, with the contents of the capsule crushed, in fasted state.
C. 1×8 mg naltrexone MEM capsule, intact, in fed state.
D. 5×8 mg (40 mg) naltrexone MEM capsules intact, in fasted state.
E. 1×1 mg naltrexone immediate-release tablets, in fasted state.

Figure 3:
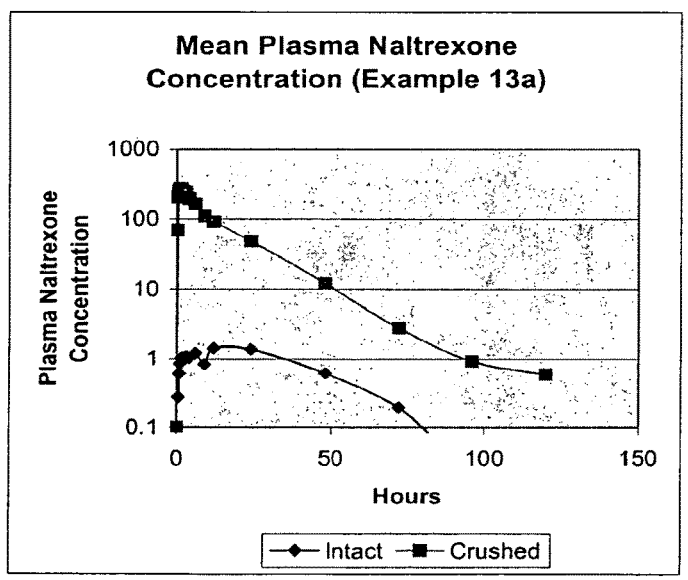
FIG. 3 is a graphical representation of the naltrexone concentration (pg/ml) versus time curve data for Example 13A.
Figure 4:
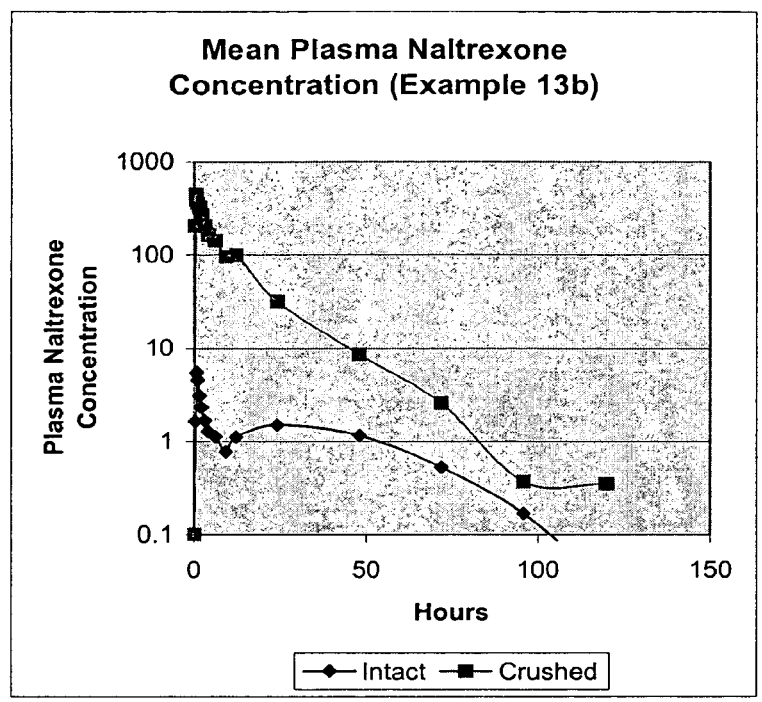
FIG. 4 is a graphical representation of the naltrexone concentration (pg/ml) versus time curve data for Example 13B.

Preliminary plasma concentrations obtained show that there is negligible amount of release of naltrexone when naltrexone MEM pellets were taken intact. Naltrexone concentration (pg/ml) versus time curve data is depicted in FIGS. 3 and 4. Naltrexone plasma levels were increased substantially when naltrexone pellets were taken orally crushed/ground in the fasted state. The mean Cmax Crushed MEMs/Intact MEMs capsule ratio for the 25% Eudragit coat and 30% Surelease coat is 187.91 and 71.98, respectively. Similarly, the mean AUCt crushed MEMs/intact MEMs capsule ratio for the 25% Eudragit coat and 30% Surelease coat is 66.07 and 39.27, respectively.

An in-vitro and in-vivo comparison of the coated MEMs of Examples 13a and 13b is set forth in Table 13G below:

TABLE 13G

| Formulation: | | EXAMPLE 13a 8 mg w/25% Eudragit | EXAMPLE 13b 8 mg w/30% Surelease |
|---|---|---|---|
| In-Vitro | Intact 36 hr Capsule Release | 0.5% | 1.6% |
|  | Crushed | 27% | 26% |
|  | Crushed:Intact Ratio | 54 | 16.3 |
| In-Vivo | AUC Intact* | 55.78 | 85.15 |
|  | (pg/mL * hr) Crushed | 3685.37 | 3344.09 |
|  | Cmax Intact* | 1.73 | 6.74 |
|  | (pg/ML) Crushed | 325.1 | 485.15 |

*normalized from 5 * 8 mg data

TABLE 13H

|  | Intact Cap 8 mg Fast N = 20 | Crushed Cap 8 mg Fast 20 | Intact Cap 8 mg Fed 19 | Intact Cap 5 × 8 mg Fast 19 | IR Tablet 1 × 1 mg Fast 20 |
|---|---|---|---|---|---|
| Cmax (pg/mL) Example 13a | 1.52 | 325.10 | 1.74 | 8.63 | 218.03 |
| AUCt (pg · hr/mL) Example 13a | 27.61 | 3685.37 | 21.41 | 278.9 | 578.92 |
| Cmax (pg/mL) Example 13b | 7.28 | 485.15 | 8.48 | 33.68 | 292.23 |
| AUCt (pg · hr/mL) Example 13b | 22.11 | 3344.09 | 65.56 | 425.76 | 543.59 |

While the invention herein disclosed as been described by means of specific embodiments and applications thereof, numerous modifications and variations could be made thereto by those skilled in the art without departing from the spirit and scope of the present invention. Such modifications are understood to be within the scope of the appended claims.

What is claimed is:
1. A method of preparing a pharmaceutical product comprising: forming pharmaceutically acceptable matrices by dispersing an opioid antagonist in a first hydrophobic material and disposing a layer comprising a second hydrophobic material over each of the matrices such that the ratio of the amount of antagonist released from the matrices after tampering to the amount of the antagonist released from intact matrices, based on the dissolution at 1 hour of the pharmaceutical product in 700 ml of simulated gastric fluid (SGF) using a USP Type II (paddle) apparatus at 50 rpm at 37 degrees C., is about 20:1 or greater, wherein the first hydrophobic material and the second hydrophobic material are each independently selected from the group consisting of ethylcellulose, a copolymer of acrylic and methacrylic esters with a molar ratio of ammonium groups to neutral (meth) acrylic esters of 1:40, and mixtures of any of the foregoing,
wherein the pharmaceutical product is devoid of gelatin, and
the layer comprises an effective amount of the second hydrophobic material to reduce a leak of the antagonist from the intact pharmaceutical product upon exposure to an environmental fluid, as compared to the pharmaceutical product without the layer.

2. A method of treating pain comprising orally administering to a patient in need thereof a dosage form comprising
   a) a plurality of extruded particles comprising an opioid antagonist dispersed in a first hydrophobic material and a layer comprising a second hydrophobic material, the layer disposed about each of the extruded particles,
   b) a plurality of particles comprising an opioid agonist dispersed in a third hydrophobic material,
   the first hydrophobic material and the layer sequestering the opioid antagonist in the extruded particles such that the ratio of the amount of antagonist released from the extruded particles after tampering to the amount of the antagonist released from the intact extruded particles, based on the dissolution at 1 hour of the pharmaceutical product in 700 ml of simulated gastric fluid (SGF) using a USP Type II (paddle) apparatus at 50 rpm, at 37 degrees C. is about 20:1 or greater, wherein the first hydrophobic material and the second hydrophobic material are each independently selected from the group consisting of ethylcellulose, a copolymer of acrylic and methacrylic esters with a molar ratio of ammonium groups to neutral (meth)acrylic esters of 1:40, and mixtures of any of the foregoing; wherein the third hydrophobic material is selected from the group consisting of ethylcellulose, acrylic polymers and copolymers, methacrylic acid polymers and copolymers, shellac, zein, hydrogenated castor oil, hydrogenated vegetable oil, and mixtures of any of the foregoing; and,
   wherein the dosage form is devoid of gelatin.

3. The method of claim 2, wherein the opioid antagonist is naltrexone or a pharmaceutically acceptable salt thereof.

4. The method of claim 2, wherein the opioid agonist is selected from the group consisting of hydrocodone, morphine, hydromorphone, oxycodone, codeine, levorphanol, meperidine, methadone, oxymorphone, buprenorphine, fentanyl, pharmaceutically acceptable salts thereof, and mixtures of any of the foregoing.

5. The method of claim 4, wherein the opioid agonist is oxycodone or a pharmaceutically acceptable salt thereof.

6. The method of claim 4, wherein the opioid agonist is hydrocodone or a pharmaceutically acceptable salt thereof.

7. The method of claim 4, wherein the opioid agonist is hydromorphone or a pharmaceutically acceptable salt thereof.

8. The method of claim 1, wherein the opioid antagonist is naltrexone or a pharmaceutically acceptable salt thereof.

9. The method of claim 1, wherein the opioid agonist is selected from the group consisting of hydrocodone, morphine, hydromorphone, oxycodone, codeine, levorphanol, meperidine, methadone, oxymorphone, buprenorphine, fentanyl, pharmaceutically acceptable salts thereof, and mixtures of any of the foregoing.

10. The method of claim 9, wherein the opioid agonist is oxycodone or a pharmaceutically acceptable salt thereof.

11. The method of claim 9, wherein the opioid agonist is hydrocodone or a pharmaceutically acceptable salt thereof.

12. The method of claim 9, wherein the opioid agonist is hydromorphone or a pharmaceutically acceptable salt thereof.

13. An oral dosage form comprising:
    an opioid agonist particle and
    a sequestered opioid antagonist particle, wherein
    the sequestered opioid antagonist particle comprises a matrix comprising a first hydrophobic material and an opioid antagonist and is coated with a layer comprising a second hydrophobic material, the matrix and the layer sequestering the opioid antagonist, wherein the first hydrophobic material and the second hydrophobic material are present in amounts such that the ratio of the amount of antagonist released from the sequestered antagonist particle after tampering to the amount of the antagonist released from the intact sequestered antagonist particle, based on the dissolution at 1 hour of the pharmaceutical product in 700 ml of simulated gastric fluid (SGF) using a USP Type II (paddle) apparatus at 50 rpm at 37 degrees C., is about 20:1 or greater, wherein the first hydrophobic material and the second hydrophobic material are each independently selected from the group consisting of ethylcellulose, a copolymer of acrylic and methacrylic esters with a molar ratio of ammonium groups to neutral (meth)acrylic esters of 1:40, and mixtures of any of the foregoing,
    wherein the dosage form is devoid of gelatin.

14. The dosage form of claim 13, which is a tablet.

15. The dosage form claim 13, which is a capsule.

16. The dosage form of claim 13, wherein the opioid antagonist is naltrexone or a pharmaceutically acceptable salt thereof.

17. The dosage form of claim 16, wherein the opioid agonist is selected from the group consisting of hydrocodone, morphine, hydromorphone, oxycodone, codeine, levorphanol, meperidine, methadone, oxymorphone, buprenorphine, fentanyl, pharmaceutically acceptable salts thereof, and mixtures of any of the foregoing.

18. The dosage form of claim 17, wherein the opioid agonist is oxycodone or a pharmaceutically acceptable salt thereof.

19. The dosage form of claim 17, wherein the opioid agonist is hydrocodone or a pharmaceutically acceptable salt thereof.

20. The dosage form of claim 17, wherein the opioid agonist is hydromorphone or a pharmaceutically acceptable salt thereof.

* * * * *